US009115389B2

(12) United States Patent
Gilad et al.

(10) Patent No.: US 9,115,389 B2
(45) Date of Patent: Aug. 25, 2015

(54) METHOD FOR DETECTING A TARGET NUCLEIC ACID COMPRISING TWO PORTIONS USING PROBES HAVING A FIRST PORTION COMPLEMENTARY TO THE FIRST PORTION OF THE TARGET NUCLEIC ACID AND A SECOND PORTION SUBSTANTIALLY COMPLEMENTARY TO THE SECOND PORTION OF THE TARGET NUCLEIC ACID

(75) Inventors: Shlomit Gilad, Ganei Hadar (IL); Esther Meiri, Shoham (IL)

(73) Assignee: Rosetta Genomics Ltd., Rehovot (IL)

( * ) Notice: Subject to any disclaimer, the term of this patent is extended or adjusted under 35 U.S.C. 154(b) by 1003 days.

(21) Appl. No.: 12/308,954

(22) PCT Filed: Jun. 29, 2007

(86) PCT No.: PCT/IB2007/003732
§ 371 (c)(1),
(2), (4) Date: Apr. 2, 2009

(87) PCT Pub. No.: WO2008/029295
PCT Pub. Date: Mar. 13, 2008

(65) Prior Publication Data
US 2010/0047784 A1 Feb. 25, 2010

Related U.S. Application Data

(60) Provisional application No. 60/806,404, filed on Jun. 30, 2006, provisional application No. 60/822,371, filed on Aug. 14, 2006, provisional application No. 60/850,455, filed on Oct. 10, 2006, provisional application No. 60/871,095, filed on Dec. 20, 2006.

(51) Int. Cl.
*C12P 19/34* (2006.01)
*C12Q 1/68* (2006.01)

(52) U.S. Cl.
CPC ............ *C12Q 1/6816* (2013.01); *C12Q 1/6832* (2013.01); *C12Q 1/6853* (2013.01); *C12Q 1/6886* (2013.01); *C12Q 2600/136* (2013.01); *C12Q 2600/178* (2013.01)

(58) Field of Classification Search
CPC ................ C12Q 1/6853; C12Q 1/686; C12Q 2525/207; C12Q 2600/178
USPC ..................................................... 435/91.21
See application file for complete search history.

(56) References Cited

U.S. PATENT DOCUMENTS

| | | | |
|---|---|---|---|
| 5,034,506 A | 7/1991 | Summerton et al. | |
| 5,124,246 A | 6/1992 | Urdea et al. | |
| 5,235,033 A | 8/1993 | Summerton et al. | |
| 5,359,100 A | 10/1994 | Urdea et al. | |
| 5,545,730 A | 8/1996 | Urdea et al. | |
| 5,571,670 A | 11/1996 | Urdea et al. | |
| 5,580,731 A | 12/1996 | Chang et al. | |
| 5,591,584 A | 1/1997 | Chang et al. | |
| 5,594,117 A | 1/1997 | Urdea et al. | |
| 5,594,118 A | 1/1997 | Urdea et al. | |
| 5,597,909 A | 1/1997 | Urdea et al. | |
| 5,635,352 A | 6/1997 | Urdea et al. | |
| 5,681,697 A | 10/1997 | Urdea et al. | |
| 5,681,702 A | 10/1997 | Collins et al. | |
| 5,780,233 A | 7/1998 | Guo et al. | |
| 6,653,081 B2 | 11/2003 | Whitcomb | |
| 6,730,479 B2 | 5/2004 | Schultz et al. | |
| 6,797,464 B2 | 9/2004 | Stevenson et al. | |
| 6,913,753 B2 | 7/2005 | Ramachandran et al. | |
| 7,642,348 B2 | 1/2010 | Bentwich et al. | |
| 8,192,937 B2 | 6/2012 | Jacobsen et al. | |
| 2002/0102557 A1* | 8/2002 | Gentile-Davey et al. | 435/6 |
| 2002/0115080 A1 | 8/2002 | Skouv et al. | |
| 2003/0108913 A1 | 6/2003 | Schouten et al. | |
| 2003/0194699 A1 | 10/2003 | Lewis et al. | |
| 2005/0059048 A1 | 3/2005 | Gunderson et al. | |
| 2005/0064457 A1 | 3/2005 | Lee | |
| 2005/0107325 A1 | 5/2005 | Manoharan et al. | |
| 2005/0112554 A1 | 5/2005 | Zhao et al. | |
| 2005/0123959 A1 | 6/2005 | Williams et al. | |
| 2005/0143795 A1 | 6/2005 | Habib et al. | |
| 2005/0182005 A1 | 8/2005 | Tuschl et al. | |
| 2005/0214753 A1 | 9/2005 | Schultz et al. | |
| 2007/0042380 A1 | 2/2007 | Bentwich et al. | |
| 2008/0182237 A1 | 7/2008 | Bentwich et al. | |

FOREIGN PATENT DOCUMENTS

| | | |
|---|---|---|
| CA | 1296242 C | 2/1992 |
| EP | 0167238 B1 | 1/1986 |
| EP | 1 130 119 A1 | 9/2001 |
| EP | 1 683 872 A1 | 7/2006 |
| EP | 1 889 924 A1 | 2/2008 |
| WO | WO 03/012135 A2 | 2/2003 |

(Continued)

OTHER PUBLICATIONS

Hurtle et al., Detection of the *Bacillus anthracis* gyrA gene by using a minor groove binder probe, J Clin Microbiol. Jan. 2004;42(1):179-85.*

Schena et al., Real-time quantitative PCR: a new technology to detect and study phytopathogenic and antagonistic fungi, European Journal of Plant Pathology 110: 893-908, 2004.*

Afonina et al., Minor Groove Binder-Conjugated DNA Probes for Quantitative DNA Detection by Hybridization-Triggered Fluorescence, BioTechniques 32:940-949 (Apr. 2002).*

(Continued)

*Primary Examiner* — Cynthia B Wilder
(74) *Attorney, Agent, or Firm* — Ron Galant; Polsinelli PC

(57) ABSTRACT

Described herein are methods and compositions for detecting, amplifying and labeling targeted nucleic acids, including microRNAs.

10 Claims, 15 Drawing Sheets

(56) References Cited

FOREIGN PATENT DOCUMENTS

| WO | WO 03/044228 A1 | 5/2003 |
| WO | WO 2005/116250 A2 | 12/2005 |
| WO | WO 2006/126040 A1 | 11/2006 |
| WO | WO 2007/090345 A1 | 8/2007 |

OTHER PUBLICATIONS

Kutyavin et. al., Nucleic Acids Research, vol. 28, No. 2., pp. 655-661, 2000.*

U.S. Appl. No. 10/709,577, filed May 14, 2004, Bentwich, et al.

U.S. Appl. No. 11/384,049.

Soutschek et al., "Therapeutic silencing of an endogenous gene by systemic administration of modified siRNAs" *Nature*, 2004, 432:173-178.

Siepel et al, "Combining Phylogenetic and Hidden Markov Models in Biosequence Analysis," *Journal of Computational Biology*, 2004, 11:413-428.

Schwartz et al., "Human-Mouse Alignments with BLASTZ," *Genome Research*, 2003, 13:103-107.

Berezikov et al., "Phylogenetic Shadowing and Computational Identification of Human microRNA Genes," *Cell*, 2005, 120:21-24.

Pruitt et al., "NCBI Reference Sequence (RefSeq): a curated non-redundant sequence database of genomes, transcripts and proteins," *Nucleic Acids Research*, 2005, 33:D501-D504.

Pruitt et al., "Introducing RefSeq and LocusLink: curated human genome resources at the NCBI," *Trends Genet.*, 2000, 16:44-47.

Tatusova et. al., "Complete genomes in WWW Entrez: data representation and anal ysis," *Bioinformatics*, 1999, 15:536-543.

Lewis et al., "Conserved Seed Pairing, Often Flanked by Adenosines, Indicates that Thousands of Human Genes are MicroRNA Targets," *Cell*, 2005, 120:15-20.

Lim et al., "Microarray analysis shoes that some microRNAs downreglate large numbers of target mRNAs," *Nature*, 2005, 433:769-773.

Baskerville et al., "Microarray profiling of microRNAs reveals frequent coexpression with neighboring miRNAs and host genes," *RNA*, 2005, 11:241-247.

Rodriguez et al., "Identification of Mammalian microRNA Host Genes and Transcript Units," *Genome Research*, 2004, 14:1902-1910.

Chen et al., "Real-time quantification of microRNAs by stem-loop RT-PCR," *Nucleic Acids Research*, 2005, 33:e179.

Fu et al., "A Novel Method to Monitor the Expression of microRNAs," *Molecular Biotechnology*, 2006, 32:197-204.

Shi et al., "Facile means for quantifying microRNA expression by real-time PCR," *BioTechniques*, 2005, 39:519-525.

Tang et al., "MicroRNA expression profiling of single whole embryonic stem cells," *Nucleic Acids Research*, 2006, 34:e9.

Schouten et al., *Relative Quantification of 40 Nucleic Acid Sequences by Multiplex Ligation-Dependent Probe Amplification*, Nucleic Acids Res. 2002, vol. 30, No. 12e57.

International Search Report dated Feb. 22, 2011, in corresponding PCT Application No. PCT/IB07/03732, 6 pages.

Jiang Jinmai et al.: "Real-time expression profiling of microRNA precursors in human cancer cell lines":, Nucleatic Acids Research, Oxford University Press, GB, vol. 33, No. 17, Jan. 1, 2005, pp. 5394-5403, XP002489966, ISSN:1362-4962.

Allawi Hatim T et al: "Quantitation of microRNAs using a modified Invader assay", RNA, Cold Spring Harbor Laboratory Press, US, vol. 10, No. 7, pp. 1153-1161 ISSN: 1355-8382; Jul. 1, 2004, XP002384569.

Schuetz E et al: "Spreadsheet Software for Thermodynamic Melting Point Prediction of Oligonucleotide Hybridization With and Without Mismatches", Biotechniques, Informa Healthcare, US, vol. 27, No. 6, Dec. 1, 1999, pp. 1218-1224, XP002948493, ISSN: 0736-6205.

European Search Report dated Apr. 18, 2012.

Guo Z et al: "Enhanced Discrimination of Single Nucleotide Polymorhisms by Artificial Mismatch Hybridization" Nature Biotechnology, vol. 15, Apr. 1, 1997, (pp. 331-335, XP000867755, ISSN: 1087-0156, DOI: 10.1038/NBT0497-331.

Conner B J et al.: "Detection of Sickle Cell Betas-Globin Allele by Hybridization with Synthetic Oligonucleotides", Proceedings of the National Academy of Sciences, vol. 80, Jan. 1, 1983, pp. 278-282, XP009009982, ISSN:0027-8424.

* cited by examiner

Fig. 2A
1) hsa-let-7a:
5'-UGAGGUAGUAGGUUGUAUAGUU -3'
(SEQ ID NO:20840)

Fig. 2B
2) Polyadenylation:
5'-UGAGGUAGUAGGUUGUAUAGUUAAAAAAAAAAAAAAAA-3'
(SEQ ID NO:21064)

Fig. 2C
3) Reverse Transcription:
5'-UGAGGUAGUAGGUUGUAUAGUUAAAAAAAAAAAAAAAA-3' (SEQ ID NO:21064)
                                                              (adaptor)
       3'-NVTTTTTTTTTTT GGATATCACTCAGCATAATTAAGACACGAGCG-5'
                        (SEQ ID NO:20857)

5'-UGAGGUAGUAGGUUGUAUAGUUAAAAAAAAAAAAAAAA-3' (SEQ ID NO:21064)
3'-ACTCCATCATCCAACATATCAATTTTTTTTTTTTTTTTGGATATCACTCAGCATAATTAAGACACGAGCG-5'
(SEQ ID NO:21072)

Fig. 2D
4) Real Time PCR
5'-TGAGGTAGTAGGTTGTATAGTTAAAAAAAAAAAAAAAACCTATAGTGAGTCGTATTAATTCTGTGCTCGC-3' (SEQ ID NO:21073)
3'-ACTCCATCATCCAACATATCAATTTTTTTTTTTTTTTTGGATATCACTCAGCATAATTAAGACACGAGCG-5' (SEQ ID NO:21072)

5'-TGAGGTAGTAGGTTGTATAGTTAAAAAAAAAAAAAAAACCTATAGTGAGTCGTATTAATTCTGTGCTCGC-3' (SEQ ID NO:21073)
                                                 (Rev primer) 3'-CAGCATAATTAAGACACGAGCG-5' (SEQ ID NO:20859)

5'-TGAGGTAGTAGGTTGTATAGTT-3' (Fwd primer) (SEQ ID NO:20840)
3'-ACTCCATCATCCAACATATCAATTTTTTTTTTTTTTTTGGATATCACTCAGCATAATTAAGACACGAGCG-5' (SEQ ID NO:21072)

Fig. 3A
1) hsa-let-7a:
5'-UGAGGUAGUAGGUUGUAUAGUU -3' (SEQ ID NO:20840)

Fig. 3B
2) Polyadenylation:
5'-UGAGGUAGUAGGUUGUAUAGUUAAAAAAAAAAAAAAAAAAAAA-3' (SEQ ID NO:21064)

Fig. 3C
3) Reverse Transcription:
5'-UGAGGUAGUAGGUUGUAUAGUUAAAAAAAAAAAAAAAAAAAAA-3' (SEQ ID NO:21064)
              3'-NVTTTTTTTTTTT GCCCATCACTCAGCATAATTAAGACACGAGCG-5' (adaptor)
              (SEQ ID NO:20836)

5'-UGAGGUAGUAGGUUGUAUAGUUAAAAAAAAAAAAAAAAAAAAA-3' (SEQ ID NO:21064)
3'-ACTCCATCATCCAACATATCAATTTTTTTTTTTTTTTTTTTTTGCCCATCACTCAGCATAATTAAGACACGAGCG-5'
              (SEQ ID NO:21068)

Fig. 3D
4) Real Time PCR
5'-TGAGGTAGTAGGTTGTATAGTTAAAAAAAAAAAAAAAAAAAAACGGGTAGTGAGTCGTATTAATTCTGTGCTCGC-3' (SEQ ID NO:21069)
3'-ACTCCATCATCCAACATATCAATTTTTTTTTTTTTTTTTTTTTGCCCATCACTCAGCATAATTAAGACACGAGCG-5' (SEQ ID NO:21070)

5'-TGAGGTAGTAGGTTGTATAGTTAAAAAAAAAAAAAAAAAAAAACGGGTAGTGAGTCGTATTAATTCTGTGCTCGC-3' (SEQ ID NO:21069)
                                              CAGCATAATTAAGACACGAGCG-5' (SEQ ID NO:20859)
                                              (Reverse primer)

5'-TGAGGTAGTAGGTTGTATAGTT-3' Fwd primer with 5' over-hanged tail (SEQ ID NO:21071)
3'-BQ- CATATCAATTTTTTTTTTTTTTGCC -FAM-5' (Taqman probe) SEQ ID NO:8592
5'-CAGTCATTTGGG TGAGGTAGTAGGTTGTATAGTT-3'
3'-ACTCCATCATCCAACATATCAATTTTTTTTTTTTTTTTTTTTTGCCCATCACTCAGCATAATTAAGACACGAGCG-5'
              (SEQ ID NO:21070)

Fig. 4A
1) hsa-let-7a:
5'-UGAGGUAGUAGGUUGUAUAGUU-3' (SEQ ID NO:20840)

2) Polyadenylation:
5'-UGAGGUAGUAGGUUGUAUAGUUAAAAAAAAAAAAAAAAAA-3' (SEQ ID NO:21064)

3) Reverse Transcription:
5'-UGAGGUAGUAGGUUGUAUAGUUAAAAAAAAAAAAAAAAAA-3' (SEQ ID NO:21064)     Fig. 4C
3'-NVTTTTTTTTTTT GCGCATCACTCAGCATAATTAAGACACGAGCG-5'
                                    (adaptor)
                               (SEQ ID NO:21067)

Fig. 4B

5'-UGAGGUAGUAGGUUGUAUAGUUAAAAAAAAAAAAAAAAAA-3' (SEQ ID NO:21064)
3'-ACTCCATCATCCAACATATCAATTTTTTTTTTTTTTTTTTTGCGCATCACTCAGCATAATTAAGACACGAGCG-5'
                                                                    (SEQ ID NO:21065)

Fig. 4D
4) Real Time PCR
5'-TGAGGTAGTAGGTTGTATAGTTAAAAAAAAAAAAAAAAAACGCGTAGTGAGTCGTATTAATTCTGTGCTCGC-3' (SEQ ID NO:21066)
3'-ACTCCATCATCCAACATATCAATTTTTTTTTTTTTTTTTTTGCGCATCACTCAGCATAATTAAGACACGAGCG-5' (SEQ ID NO:21065)

3'-BQ- CATATCAATTTTTTTTTTTGCC -FAM-5'
                                    (Taqman probe) SEQ ID NO:20846

5'-TGAGGTAGTAGGTTGTATAGTTAAAAAAAAAAAAAAAAAACGCGTAGTGAGTCGTATTAATTCTGTGCTCGC-3' (SEQ ID NO:21066)
                                          CAGCATAATTAAGACACGAGCG-5' (SEQ ID NO:20859)
                                              (Reverse primer)

5'-TGAGGTAGTAGGTTGTGTATAGTTAAAAAAAAAAAAAAAAACGCGTAGTGAGTCGTATTAATTCTGTGCTCGC-3' (SEQ ID NO:21066)
5'-CAGTCATTTGGGTGAGTCGTAGTAGGTTGT-3' (Fwd primer with 5' over-hanged tail) (SEQ ID NO:8082)
3'-ACTCCATCATCCAACATATCAATTTTTTTTTTTTTTTTTTTGCGCATCACTCAGCATAATTAAGACACGAGCG-5'
                                                                    (SEQ ID NO:21065)

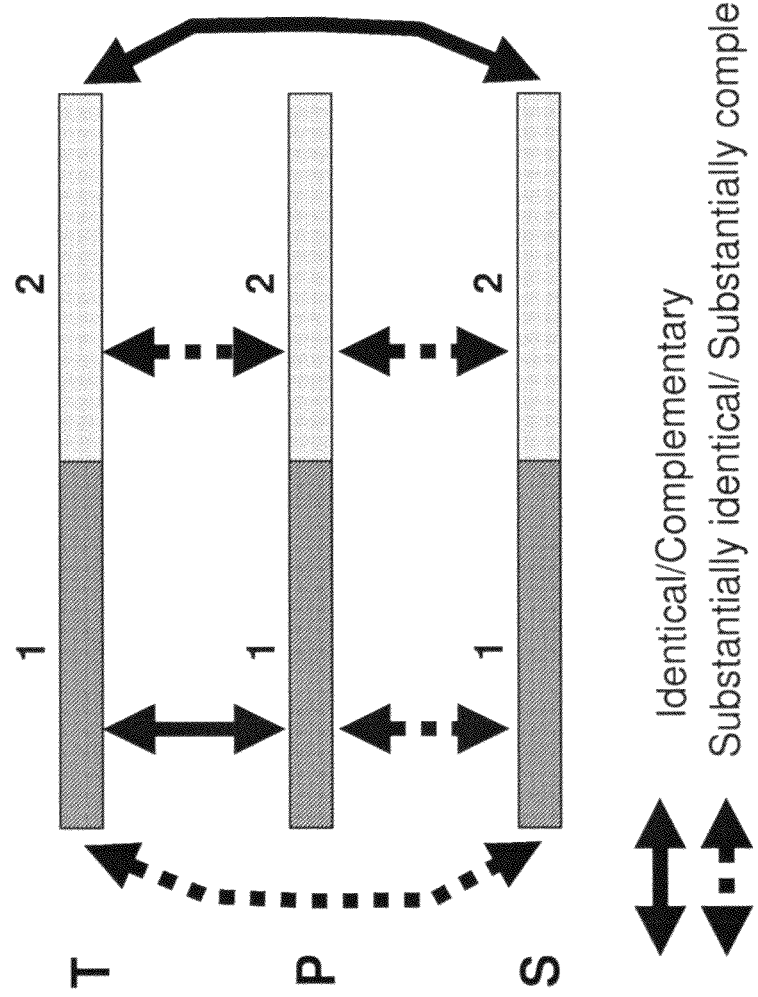

METHOD FOR DETECTING A TARGET NUCLEIC ACID COMPRISING TWO PORTIONS USING PROBES HAVING A FIRST PORTION COMPLEMENTARY TO THE FIRST PORTION OF THE TARGET NUCLEIC ACID AND A SECOND PORTION SUBSTANTIALLY COMPLEMENTARY TO THE SECOND PORTION OF THE TARGET NUCLEIC ACID

FIELD OF THE INVENTION

The invention relates in general to methods and compositions for detecting, amplifying and labeling nucleic acid molecules, including microRNAs.

BACKGROUND OF THE INVENTION

The identification and quantification of specific nucleic acid sequences has been an area of great interest in molecular biology over the past two decades. Expression profiles within the area of identification and quantification of specific nucleic acids is currently being intensely studied. The ability to identify and quantify certain nucleic acids and their products has advanced a broad range of disciplines, such as individualized medicine, and evaluation of drug resistance.

While much has been learned about various methods for identifying and quantifying specific nucleic acid sequences, these methods lack accuracy and precision for identifying small variations in nucleic acid sequences, resulting in a high level of false positives and an inability to broadly apply these methods. Methods for identifying target nucleic acids with specific single base polymorphisms have proven to be ineffective when these nucleic acids are present in a high background of other nucleic acids including nucleic acids with sequences similar to the target nucleic acids. Probe design has limited the number of different variable nucleic acids that can be identified at a time, and require controlled backgrounds of known nucleic acids. Probes associated with methods such as Real Time PCR for detecting particular nucleic acid variants including microRNAs (miRNAs) have also been problematic because of non-specific binding to RT primers and lack of sufficient sensitivity to the target sequences.

miRNAs are short RNA oligonucleotides of approximately 22 nucleotides that are involved in gene regulation. miRNAs regulate gene expression by targeting mRNAs for cleavage or translational repression. The role of miRNAs in the development and progression of disease has only recently become appreciated. Deregulated miRNA expression is implicated in onset and progression of different diseases including, but not limited to embryonic malformations and cancers.

As a result of their small size, miRNAs have been difficult to identify using standard methodologies. A limited number of miRNAs have been identified by extracting large quantities of RNA. miRNAs have also been identified that contribute to the presentation of visibly discernable phenotypes. Expression array data shows that miRNAs are expressed in different developmental stages or in different tissues.

Moreover, because of their potential broad use in treating and diagnosing different diseases, there is a need in the art (yet unmet) to develop methods of identification, isolation and also quatitation of miRNAs. The present invention addresses the need by disclosing efficient and sensitive methods and compositions for isolating and quantitating miRNAs from different samples, including those wherein there is only minimum amount of a starting material available.

SUMMARY OF THE INVENTION

A method of detecting a target nucleic acid is provided. The method may comprise providing a sample comprising a target nucleic acid, wherein the target nucleic acid comprises a first portion and a second portion, and contacting the target nucleic acid with a probe. The probe may comprise a first portion complementary to the first portion of the target nucleic acid, and a second portion that is substantially complementary to the second portion of the target nucleic acid. The level of probe binding to the target nucleic acid may be compared to a control and may be indicative of the level of target nucleic acid present in the sample.

A method of detecting a target nucleic acid amongst one or more other nucleic acids is also provided. The method may comprise providing a sample comprising a target nucleic acid and a sibling nucleic acid, wherein the target nucleic acid comprises a first portion and a second portion, and the sibling nucleic acid comprises a first portion and a second portion. The method may further comprise contacting the target nucleic acid with a probe. The first portion of the target nucleic acid and first portion of the sibling nucleic acid are substantially identical. The first portion of the sibling nucleic acid is substantially complementary to the first portion of the probe. The second portion of the sibling nucleic acid is substantially complementary to the second portion of the probe. The level of probe binding to the target nucleic acid may be compared to a control and may be indicative of the level of target nucleic acid present in the sample.

A method of detecting a plurality of target nucleic acids in a sample is also provided. Each target nucleic acid may comprise a first portion and a second portion. The method may comprise providing a sample containing a plurality of target nucleic acids and contacting the target nucleic acids with a plurality of probes. The sample may also comprise a plurality of sibling nucleic acids. Each probe may be capable of distinguishing a target nucleic acid from a sibling nucleic acid in the sample. Each sibling nucleic acid comprises a first portion and a second portion. The first portion of the sibling nucleic acid is substantially complementary to the first portion of the sibling nucleic acid. Each probe of the method may comprise a first portion complementary to the first portion of one of the target nucleic acids and a second portion substantially complementary to the second portion of one of the target nucleic acids. The level of each probe binding to each target nucleic acid may be compared to a control is indicative of the level of each target nucleic acid present in the sample.

A method of detecting a target nucleic acid amongst one or more other sibling nucleic acids is also provided. The method may comprise providing a sample comprising a target nucleic acid comprise a first portion and second portion, and contacting the sample with a probe comprising a first portion and a second portion. The first portion of the target nucleic acid may comprise a variant site. The sibling nucleic acid may also comprise a first portion and second portion. The first portion of the sibling nucleic acid may also comprise a variant site. The variant site of the target nucleic acid may differ from the variant site of the sibling nucleic acid by as few as one nucleotide. The first portion of the probe may comprise a detection site that is complementary to the variant site of the target nucleic acid but is noncomplementary to the variant site of the sibling nucleic acid. The probe may also comprise a sensitizing site in the second portion that is substantially complementary to the second portion of both the target nucleic acid and the sibling nucleic acid. The probe may allow specific detection of the target nucleic acid in a diverse background of other substantially identical sibling nucleic acids ranging in concentration from low to high.

The target nucleic acid of the method may be mRNA, miRNA, pri-mRNA, pre-mRNA, siRNA, anti-miRNA, DNA, or cDNA. The target nucleic acid may be isolated from bacteria, viruses, animals, or humans. The target nucleic acid may be amplified. The amplification of the target nucleic acid may be by polymerase chain reaction using forward and reverse primers wherein the forward primer may comprise a sequence selected from the group consisting of any one of SEQ ID NOS: 4168-8334. The probe of the method may comprise a label, which may be fluorophore. The label may further comprise a quencher molecule. The fluorophore may be distal to the quencher molecule. The probe may comprise a sequence selected from the group consisting of any one of SEQ ID NOS: 8335-20835. The sample of the method may be a biological sample. The biological sample may be selected from the group consisting of blood, a blood fraction, amniotic fluid, urine, ascetic fluid, saliva, cerebrospinal fluid, cervical secretions, vaginal secretions, endometrial secretions, gastrointestinal secretions, bronchial secretions, sputum, pleural effusion, secretions from the breast, secretions from ovarian cyst, sperm, cell line and tissue sample.

A method for detecting a disease or condition is also provided. The method may comprise providing a sample wherein the sample has a target nucleic acid and a sibling nucleic acid. The method may further comprise contacting the target nucleic acid with a probe. The method may also comprise measuring a difference in the level of a target nucleic acid to a control, which is indicative of the disease or condition or the presence of a viral or bacterial infection. The disease or condition may be cancer, HIV, Hepatitis B or human papilloma virus infection.

A method for genotyping an individual is also provided. The method may comprise providing a sample where the sample has a target nucleic acid and a sibling nucleic acid. The method may further comprise contacting the target nucleic acid with a probe. The method may also comprise measuring the difference in the level of a target nucleic acid to a control, which is indicative of the genotype of the individual.

A method for identifying microRNA expression in a body-fluid sample obtained from a subject is also provided. The method may comprise providing RNA from said sample, wherein said RNA comprises a microRNA. The method may further comprise generating a reverse transcript of the polyadenylated RNA and amplifying the reverse transcript by polymerase chain reaction comprising a forward primer, a reverse primer, and a probe. The body-fluid sample is selected from the group consisting of: blood, serum, urine, amniotic fluid, ascitic fluid, saliva, cervical secretions, vaginal secretions, endometrial secretions, gastrointestinal secretions, bronchial secretions, sputum, pleural effusion, secretions from the breast, secretions from ovarian cyst, and sperm.

The forward primer may comprise a sequence selected from the group consisting of any one of SEQ ID NOS: 4168-8334. The probe may comprise a sequence selected from the group consisting of any one of SEQ ID NOS: 8335-20835.

A biochip is also provided. The biochip may comprise a plurality of probes. The probes may comprise negative probes, positive probes, spike probes, and test probes. A negative probe may comprise a nucleic acid substantially complementary to a miRNA*. The sequence of the nucleic acid may be selected from the group consisting of any one of SEQ ID NOS: 20863-20925. A positive probe may comprise a nucleic acid substantially complementary to a small RNA. The sequence of the nucleic acid may be selected from the group consisting of any one of SEQ ID NOS: 20926-20937. A spike probe may comprise a nucleic acid with a sequence that is not complementary to any sequence of 60 nucleotides in a genome which may be human, rat, virus or mouse. The sequence of the nucleic acid may be selected from the group consisting of any one of SEQ ID NOS: 20938-20951.

A test probe may comprise 40 to 60 nucleotides. A test probe may comprise a nucleic acid that is substantially complementary to a miRNA. The nucleic acid may comprise 16 to 29 nucleotides. The sequence of the nucleic acid may be selected from the group consisting of any one of SEQ ID NOS: 1-4167. The test probe may also comprise a linker. The linker may comprise a nucleic acid, wherein the sequence of the nucleic acid may be selected from the group consisting of any one of SEQ ID NOS: 20952-21063. Also provided is a method of detecting a nucleic acid. A biological sample may be provided. The biochip may be contacted with the biological sample. The level of a nucleic acid may be measured. A difference in the level of the nucleic acid compared to a control may be indicative the nucleic acid being detected in the biological sample. The nucleic acid may be a pri-miRNA, a pre-miRNA, or a miRNA. The nucleic acid may be labeled with a fluorophore.

A direct and robust way to label microRNAs (miRNAs) is also provided. Also provided are a methods for detecting and measuring relative levels of miRNAs using LUMINEX® technology, and methods of calibrating the detection method. LUMINEX® provides a "solution based biochip" method. The methods describer herein may be applied to other similar platforms.

BRIEF DESCRIPTION OF THE DRAWINGS

FIGS. 2A-D are a schematic of the method of Shi and Chiang (2005). Following total RNA extraction (FIG. 2A), a polyadenylation reaction is performed (FIG. 2B). Next, the products are reverse transcribed using a poly(T) adapter linked to a specific tail, creating cDNA (FIG. 2C). Following this stage, a real time PCR reaction is performed using SYBR Green as a fluorophore, enabling the quantification of product accumulation (FIG. 2D).

FIGS. 3A-D are a schematic representation of a method of detection provided by the present invention. The target miRNA in this example is from the human let-7a family.

FIGS. 4A-D are another schematic representation of a method of detection provided by the present invention, in which there is a base mismatch between the sequence introduced by the adaptor during reverse transcription of polyadenylated target nucleic acid and the probe (FIG. 4D). The target miRNA in this example is from the human let-7a family.

FIG. 5 is a schematic representation of the method for detecting a target nucleic acid. Three nucleic acids are represented, each comprising a first portion (marked by a "1") and a second portion (marked by a "2"). A target nucleic acid is indicated by the letter T, a probe is indicated by the letter P, and a sibling nucleic acid is indicated by the letter S. A straight arrow drawn between two nucleic acid portions indicates that the sequences of the two portions are either identical or complementary. A dashed arrow drawn between two portions indicates that the sequences of the two portions are either substantially identical or substantially complementary. The first portions of the target nucleic acid and sibling nucleic acid are substantially identical, while the second portions of the target nucleic acid and sibling nucleic acid are identical. The second portions of the probe and the target nucleic acid are substantially complementary, as are the second portions of the probe and the sibling nucleic acid. This substantial complementarity allows the probe to distinguish the target nucleic acid from its sibling nucleic acid, because the first portion of the probe is identical to the first portion of the target nucleic acid, but only substantially complementary to the sibling nucleic acid.

DETAILED DESCRIPTION

Figure 1:
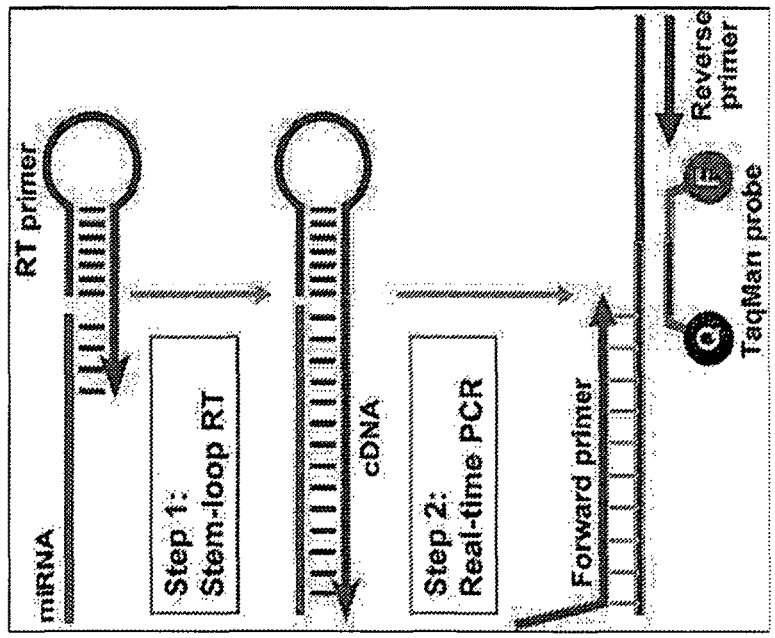
FIG. 1 is a schematic description of TaqMan miRNA assays. TaqMan-based real time quantification of miRNAs includes two steps, stem-loop reverse transcription (RT) and real time PCR. Stem-loop RT primers bind to the 3' portion of miRNA molecules and are reverse transcribed with reverse transcriptase. Then, the RT product is quantified using conventional TaqMan PCR that includes miRNA-specific forward primer, reverse primer and a dye-labeled TaqMan probe. The purpose of tailed forward primer at 5' is to increase its melting temperature (Tm) depending on the sequence composition of miRNA molecules.

Provided herein are methods for detecting a target nucleic acid. The method comprising contacting the target nucleic acid with a probe that has at least one mismatch to the target nucleic acid. The mismatch may allow the probe to distinguish the target nucleic acid from other nucleic acids that are substantially identical to the target nucleic acid and that differ from the target nucleic acid by as few as one nucleotide. The ability of the probe to distinguish the target nucleic acid over other substantially identical nucleic acids may be due to the presence of at least one additional mismatch between the probe and the other substantially identical nucleic acids. The method may allow specific detection of a target nucleic acid in a diverse background of other substantially identical nucleic acids ranging in concentration from low to high.

Also provided are methods and compositions that may be useful, among other things, for diagnostic and prognostic purposes.

Other aspects of the invention will become apparent to the skilled artisan by the following description of the invention.

1. Definitions

Before the present materials and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise. For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

a. Animal

"Animal" as used herein may mean fish, amphibians, reptiles, birds, and mammals, such as mice, rats, rabbits, goats, cats, dogs, cows, apes and humans.

b. Anti-miRNA

"Anti-RNA" as used herein is a RNA that is capable of blocking the activity of a miRNA or miRNA*, such as by binding to the pri-miRNA, pre-miRNA, miRNA or miRNA* (e.g. antisense or RNA silencing), or by binding to the target binding site. The anti-miRNA may comprise a total of 5-100 or 10-60 nucleotides. The anti-miRNA may also comprise a total of at least 5-40 nucleotides. The sequence of the anti-miRNA may comprise (a) at least 5 nucleotides that are substantially complementary to the 5' of a miRNA and at least 5-12 nucleotides that are substantially identical to the flanking regions of the target site from the 5' end of the miRNA, for the purposes of binding to a miRNA and repressing its activity; or (b) at least 5-12 nucleotides that are substantially identical to the 3' of a miRNA and at least 5 nucleotide that are substantially complementary to the flanking region of the target site from the 3' end of the miRNA, for the purposes of inhibiting the ability of a miRNA to bind to its target. The sequence of the anti-miRNA may comprise the sequence of a anti-miRNA disclosed in U.S. patent application Ser. Nos. 11/384,049, 11/418,870 or 11/429,720, the contents of which are incorporated herein, or variants thereof.

c. Attached

"Attached" or "immobilized" as used herein to refer to a probe and a solid support may mean that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

d. Biological Sample

"Biological sample" as used herein may mean a sample of biological tissue or fluid that comprises nucleic acids. Such samples include, but are not limited to, tissue or fluid isolated from animals. Biological samples may also include sections of tissues such as biopsy and autopsy samples, frozen sections taken for histologic purposes, hair, and skin. Biological samples may also include explants and primary and/or transformed cell cultures derived from animal or patient tissues. Biological samples may also be blood, a blood fraction, plasma, serum, urine, pleural effusion, mucus, ascitic fluid, amniotic fluid, stool, tears, saliva, cerebrospinal fluid, cervical secretions, vaginal secretions, endometrial secretions, gastrointestinal secretions, bronchial secretions, sputum, secretions from ovarian cyst, sperm, secretions from the breast, cell line, or tissue sample. A biological sample may be provided by removing a sample of cells from an animal, but can also be accomplished by using previously isolated cells (e.g., isolated by another person, at another time, and/or for another purpose), or by performing the methods described herein in vivo. Archival tissues, such as those having treatment or outcome history (e.g., formalin fixed, paraffin-embedded (FFPE) tissues), may also be used.

e. Complement

"Complement" or "complementary" as used herein to refer to a nucleic acid may mean Watson-Crick (e.g., A-T/U and C-G) or Hoogsteen base pairing between nucleotides or nucleotide analogs of nucleic acid molecules.

f. Detection

"Detection" may mean detecting the presence of a component in a sample. Detection may also mean detecting the absence of a component. Detection may also mean measuring the level of a component, either quantitatively or qualitatively.

g. Differential Expression

"Differential expression" may mean qualitative or quantitative differences in the temporal and/or cellular gene expression patterns within and among cells and tissue. Thus, a differentially expressed gene may qualitatively have its expression altered, including an activation or inactivation, in, e.g., normal versus disease tissue. Genes may be turned on or turned off in a particular state, relative to another state thus permitting comparison of two or more states. A qualitatively regulated gene may exhibit an expression pattern within a state or cell type which may be detectable by standard techniques. Some genes may be expressed in one state or cell type, but not in both. Alternatively, the difference in expression may be quantitative, e.g., in that expression is modulated, either up-regulated, resulting in an increased amount of transcript, or down-regulated, resulting in a decreased amount of transcript. The degree to which expression differs need only be large enough to quantify via standard characterization techniques such as expression arrays, quantitative reverse transcriptase PCR, northern analysis, real-time PCR, and RNase protection.

h. Gene

"Gene" used herein may be a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

i. Groove Binder/Minor Groove Binder (MGB)

"Groove binder" and/or "minor groove binder" may be used interchangeably and refer to small molecules that fit into the minor groove of double-stranded DNA, typically in a sequence-specific manner. Minor groove binders may be long, flat molecules that can adopt a crescent-like shape and thus, fit snugly into the minor groove of a double helix, often displacing water. Minor groove binding molecules may typically comprise several aromatic rings connected by bonds with torsional freedom such as furan, benzene, or pyrrole rings. Minor groove binders may be antibiotics such as netropsin, distamycin, berenil, pentamidine and other aromatic diamidines, Hoechst 33258, SN 6999, aureolic anti-tumor drugs such as chromomycin and mithramycin, CC-1065, dihydrocyclopyrroloindole tripeptide ($DPI_3$), 1,2-dihydro-(3H)-pyrrolo[3,2-e]indole-7-carboxylate ($CDPI_3$), and related compounds and analogues, including those described in Nucleic Acids in Chemistry and Biology, 2d ed., Blackburn and Gait, eds., Oxford University Press, 1996, and PCT Published Application No. WO 03/078450, the contents of which are incorporated herein by reference. A minor groove binder may be a component of a primer, a probe, a hybridization tag complement, or combinations thereof. Minor groove binders may increase the $T_m$ of the primer or a probe to which they are attached, allowing such primers or probes to effectively hybridize at higher temperatures.

j. Identity

"Identical" or "identity" as used herein in the context of two or more nucleic acids or polypeptide sequences may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

k. Label

"Label" as used herein may mean a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and other entities which can be made detectable. A label may be a fluorophore, such as described in U.S. Pat. No. 6,541,618, the contents of which are incorporated herein by reference. A label may also be a quencher molecule, which when in proximity to another label, may decrease the amount of detectable signal of the other label, such as described in U.S. Pat. No. 6,541,618, the contents of which are incorporated herein by reference. A label may be incorporated into nucleic acids and proteins at any position.

l. miRNA

"miRNA" used herein may mean an RNA sequence capable of inhibiting a mRNA sequence. mRNA may mean include miRNA* or a variant thereof. The miRNA sequence may comprise from 13-33, 18-24 or 21-23 nucleotides. The miRNA may also comprise a total of at least 5-40 nucleotides. The sequence of the miRNA may be the first 13-33 nucleotides of the pre-miRNA. The sequence of the miRNA may also be the last 13-33 nucleotides of the pre-miRNA. The sequence of the miRNA may comprise the sequence of a miRNA disclosed in U.S. patent application Ser. Nos. 11/384,049, 11/418,870 or 11/429,720, the contents of which are incorporated herein, or variants thereof.

m. Nucleic Acid

"Nucleic acid" or "oligonucleotide" or "polynucleotide" used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be synthesized as a single stranded molecule or expressed in a cell (in vitro or in vivo) using a synthetic gene. Nucleic acids may be obtained by chemical synthesis methods or by recombinant methods.

The nucleic acid may also be a RNA such as a mRNA, tRNA, shRNA, siRNA or Piwi-interacting RNA, or a pri-miRNA, pre-miRNA, miRNA, or anti-miRNA, as described in U.S. patent application Ser. No. 11/429,720, 11/384,049, 11/418,870, 11/429,720, International Application Nos. PCT/IB05/02352, and PCT/EB2005/002702, the contents of which are fully incorporated herein by reference.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modified nucleotides also include nucleotides conjugated with cholesterol through, e.g., a hydroxyprolinol linkage as described in Krutzfeldt et al., Nature (Oct. 30, 2005), Soutschek et al., Nature 432:173-178 (2004), and U.S. Patent Publication No. 20050107325, which are incorporated herein by reference. Modified nucleotides and nucleic acids may also include locked nucleic acids (LNA), as described in U.S. Patent No. 20020115080, which is incorporated herein by reference. Additional modified nucleotides and nucleic acids are described in U.S. Patent Publication No. 20050182005, which is incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. Mixtures of naturally occurring nucleic acids and analogs may be made; alternatively, mixtures of different nucleic acid analogs, and mixtures of naturally occurring nucleic acids and analogs may be made.

The nucleic acid may have a length of 10 to 30,000 nucleotides, 10-25,000 nucleotides, 10-20,000 nucleotides, 10-10,000 nucleotides, 10-5,000 nucleotides, 10-2,500 nucleotides, 10-1,000 nucleotides, 10-250 nucleotides, 10-100 nucleotides, and 10-50 nucleotides. The nucleic acid may have a length of at least 10, 11, 11, 12, 13, 14, 15, 16, 17, 18, 19, 20, 21, 22, 23, 24, 25-40, 40-70, 80-125, 125-175, 175-200, or 200-250 nucleotides.

n. Pre-mRNA

"Pre-mRNA" used herein may mean mRNA sequence comprising a miRNA and a miRNA*. The pre-miRNA sequence may comprise from 45-90, 60-80 or 60-70 nucleotides. The sequence of the pre-miRNA may also be that of a pri-miRNA excluding from 0-160 nucleotides from the 5' and 3' ends of the pri-miRNA. The sequence of the pre-miRNA may comprise the sequence of a pre-miRNA disclosed in U.S. patent application Ser. Nos. 11/384,049, 11/418,870 or 11/429,720, the contents of which are incorporated herein, or variants thereof.

o. Pri-mRNA

"Pri-mRNA" used herein may mean mRNA sequence comprising a pre-miRNA, miRNA, and miRNA*. The sequence of the pri-miRNA may comprise variants thereof. The sequence of the pri-miRNA may comprise the sequence of a pri-miRNA disclosed in U.S. patent application Ser. Nos. 11/384,049, 11/418,870 or 11/429,720, the contents of which are incorporated herein, or variants thereof. The pri-miRNA sequence may comprise from 45-30,000, 50-25,000, 100-20,000, 1,000-1,500 or 80-100 nucleotides.

The pri-miRNA may form a hairpin structure. The hairpin may comprise first and second nucleic acid sequences that are substantially complementary. The first and second nucleic acid sequence may be from 37-50 nucleotides. The first and second nucleic acid sequence may be separated by a third sequence of from 8-12 nucleotides. The hairpin structure may have a free energy less than −25 Kcal/mole as calculated by the Vienna algorithm with default parameters, as described in Hofacker et al., Monatshefte f. Chemie 125: 167-188 (1994), the contents of which are incorporated herein. The hairpin may comprise a terminal loop of 4-20, 8-12 or 10 nucleotides. The pri-miRNA may comprise at least 19% adenosine nucleotides, at least 16% cytosine nucleotides, at least 23% thymine nucleotides and at least 19% guanine nucleotides.

p. Stringent Hybridization Conditions

"Stringent hybridization conditions" used herein may mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

q. Substantially Complementary

"Substantially complementary" used herein may mean that a first sequence is at least 50%, 55%, 60%, 65%, 70%, 75%, 80%, 85%, 90%, 95%, 97%, 98% or 99% identical to the complement of a second sequence over a region of 2, 3, 4, 5, 6, 7, 8, 9, 10, 11, 12, 13, 14, 15, 16, 17, 18, 19, 20-40, 40-60, 60-100, or more nucleotides, or that the two sequences hybridize under stringent hybridization conditions.

r. Substantially Identical

"Substantially identical" used herein may mean that a first and second sequence are at least 50%, 55%, 60%, 65%, 70%, 75%, 80%, 85%, 90%, 95%, 97%, 98% or 99% identical over a region of 2, 3, 4, 5, 6, 7, 8, 9, 10, 11, 12, 13, 14, 15, 16, 17, 18, 19, 20-40, 40-60, 60-100, or more nucleotides or amino acids, or with respect to nucleic acids, if the first sequence is substantially complementary to the complement of the second sequence.

s. Target Nucleic Acid

"Target nucleic acid" as used herein may mean a nucleic acid or variant thereof that may be bound by another nucleic acid. A target nucleic acid may be a DNA sequence. The target nucleic acid may be an RNA. The target nucleic acid may comprise a mRNA, tRNA, shRNA, siRNA or Piwi-interacting RNA, or a pri-miRNA, pre-miRNA, miRNA, or anti-miRNA. The target nucleic acid may comprise a target miRNA binding site or a variant thereof. One or more probes may bind the target nucleic acid. The target binding site may be comprise 5-100 or 10-60 nucleotides. The target binding site may comprise a total of 5, 6, 7, 8, 9, 10, 11, 12, 13, 14, 15, 16, 17, 18, 19, 20, 21, 22, 23, 24, 25, 26, 27, 28, 29, 30-40, 40-50, 50-60, 61, 62 or 63 nucleotides. The target site sequence may comprise at least 5 nucleotides of the sequence of a target miRNA binding site disclosed in U.S. patent application Ser. Nos. 11/384,049, 11/418,870 or 11/429,720, the contents of which are incorporated herein.

t. Variant

"Variant" as used herein to refer to a nucleic acid may mean (i) a portion of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

2. Probes

A probe is provided herein. A probe may comprise a nucleic acid. The probe may have a length of from 8 to 500, 10 to 100 or 20 to 60 nucleotides. The probe may also have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe may comprise a nucleic acid of 18-25 nucleotides.

A probe may be capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. A probe may be single stranded or partially single and partially double stranded. The strandedness of the probe is dictated by the structure, composition, and properties of the target sequence. Probes may be directly labeled or indirectly labeled.

a. Linker Sequences

The probe may further comprise a linker. The linker may be 10-60 nucleotides in length. The linker may be 20-27 nucleotides in length. The linker may be of sufficient length to allow the probe to be a total length of 45-60 nucleotides. The linker may not be capable of forming a stable secondary structure, may not be capable of folding on itself, or may not be capable of folding on a non-linker portion of a nucleic acid contained in the probe. The sequence of the linker may not appear in the genome of the animal from which the probe non-linker nucleic acid is derived. The linker may be selected from a sequence in Table 1 (SEQ ID NOS: 20952-21063).

TABLE 1

The linker sequences

| Sequence | SEQ ID NO |
|---|---|
| GCAATGCTAGCTATTGCTTGCTATT | 20952 |
| GCAATGCTAGCTATTGCTTGCTAT | 20953 |
| GCAATGCTAGCTATTGCTTGCTA | 20954 |
| GCAATGCTAGCTATTGCTTGCT | 20955 |
| GCAATGCTAGCTATTGCTTGC | 20956 |
| GCAATGCTAGCTATTGCTTG | 20957 |
| GCAATGCTAGCTATTGCTT | 20958 |
| GCAATGCTAGCTATTGCT | 20959 |
| GCAATGCTAGCTATTGC | 20960 |
| GCAATGCTAGCTATTG | 20961 |
| GCAATGCTAGCTATT | 20962 |
| GCAATGCTAGCTAT | 20963 |
| GCAATGCTAGCTA | 20964 |
| GCAATGCTAGCT | 20965 |
| GCAATGCTAGC | 20966 |
| GCAATGCTAG | 20967 |
| GCAATGCTA | 20968 |
| GCAATGCT | 20969 |
| GCAATGC | 20970 |
| GCAATG | 20971 |
| GCAAT | 20972 |
| TATCCTACTATACGTATCACATAGCGTTCCGTATGTGGCCGGGATAGACCTAGCTTAAGC | 20973 |
| TATCCTACTATACGTATCACATAGCGTTCCGTATGTGGCCGGGATAGACCTAGCTTAAG | 20974 |
| TATCCTACTATACGTATCACATAGCGTTCCGTATGTGGCCGGGATAGACCTAGCTTAA | 20975 |
| TATCCTACTATACGTATCACATAGCGTTCCGTATGTGGCCGGGATAGACCTAGCTTA | 20976 |
| TATCCTACTATACGTATCACATAGCGTTCCGTATGTGGCCGGGATAGACCTAGCTT | 20977 |
| TATCCTACTATACGTATCACATAGCGTTCCGTATGTGGCCGGGATAGACCTAGCT | 20978 |
| TATCCTACTATACGTATCACATAGCGTTCCGTATGTGGCCGGGATAGACCTAGC | 20979 |
| TATCCTACTATACGTATCACATAGCGTTCCGTATGTGGCCGGGATAGACCTAG | 20980 |
| TATCCTACTATACGTATCACATAGCGTTCCGTATGTGGCCGGGATAGACCTA | 20981 |
| TATCCTACTATACGTATCACATAGCGTTCCGTATGTGGCCGGGATAGACCT | 20982 |
| TATCCTACTATACGTATCACATAGCGTTCCGTATGTGGCCGGGATAGACC | 20983 |
| TATCCTACTATACGTATCACATAGCGTTCCGTATGTGGCCGGGATAGAC | 20984 |
| TATCCTACTATACGTATCACATAGCGTTCCGTATGTGGCCGGGATAGA | 20985 |
| TATCCTACTATACGTATCACATAGCGTTCCGTATGTGGCCGGGATAG | 20986 |
| TATCCTACTATACGTATCACATAGCGTTCCGTATGTGGCCGGGATA | 20987 |
| TATCCTACTATACGTATCACATAGCGTTCCGTATGTGGCCGGGAT | 20988 |
| TATCCTACTATACGTATCACATAGCGTTCCGTATGTGGCCGGGA | 20989 |

TABLE 1-continued

The linker sequences

| Sequence | SEQ ID NO |
|---|---|
| TATCCTACTATACGTATCACATAGCGTTCCGTATGTGGCCGGG | 20990 |
| TATCCTACTATACGTATCACATAGCGTTCCGTATGTGGCCGG | 20991 |
| TATCCTACTATACGTATCACATAGCGTTCCGTATGTGGCCG | 20992 |
| TATCCTACTATACGTATCACATAGCGTTCCGTATGTGGCC | 20993 |
| TATCCTACTATACGTATCACATAGCGTTCCGTATGTGGC | 20994 |
| TATCCTACTATACGTATCACATAGCGTTCCGTATGTGG | 20995 |
| TATCCTACTATACGTATCACATAGCGTTCCGTATGTG | 20996 |
| TATCCTACTATACGTATCACATAGCGTTCCGTATGT | 20997 |
| TATCCTACTATACGTATCACATAGCGTTCCGTATG | 20998 |
| TATCCTACTATACGTATCACATAGCGTTCCGTAT | 20999 |
| TATCCTACTATACGTATCACATAGCGTTCCGTA | 21000 |
| TATCCTACTATACGTATCACATAGCGTTCCGT | 21001 |
| TATCCTACTATACGTATCACATAGCGTTCCG | 21002 |
| TATCCTACTATACGTATCACATAGCGTTCC | 21003 |
| TATCCTACTATACGTATCACATAGCGTTC | 21004 |
| TATCCTACTATACGTATCACATAGCGTT | 21005 |
| TATCCTACTATACGTATCACATAGCGT | 21006 |
| TATCCTACTATACGTATCACATAGCG | 21007 |
| TATCCTACTATACGTATCACATAGC | 21008 |
| TATCCTACTATACGTATCACATAG | 21009 |
| TATCCTACTATACGTATCACATA | 21010 |
| TATCCTACTATACGTATCACAT | 21011 |
| TATCCTACTATACGTATCACA | 21012 |
| TATCCTACTATACGTATCAC | 21013 |
| TATCCTACTATACGTATCA | 21014 |
| TATCCTACTATACGTATC | 21015 |
| TATCCTACTATACGTAT | 21016 |
| TATCCTACTATACGTA | 21017 |
| TATCCTACTATACGT | 21018 |
| TATCCTACTATACG | 21019 |
| TATCCTACTATAC | 21020 |
| TATCCTACTAT | 21021 |
| TATCCTACTA | 21022 |
| TATCCTACT | 21023 |
| TATCCTAC | 21024 |
| TATCCTA | 21025 |
| TATCCT | 21026 |

TABLE 1-continued

The linker sequences

| Sequence | SEQ ID NO |
|---|---|
| TATCC | 21027 |
| CGAACGATAACGGATCGTTACGATCGATAACGAACGATAA | 21028 |
| CGAACGATAACGGATCGTTACGATCGATAACGAACGATA | 21029 |
| CGAACGATAACGGATCGTTACGATCGATAACGAACGAT | 21030 |
| CGAACGATAACGGATCGTTACGATCGATAACGAACGA | 21031 |
| CGAACGATAACGGATCGTTACGATCGATAACGAACG | 21032 |
| CGAACGATAACGGATCGTTACGATCGATAACGAAC | 21033 |
| CGAACGATAACGGATCGTTACGATCGATAACGAA | 21034 |
| CGAACGATAACGGATCGTTACGATCGATAACGA | 21035 |
| CGAACGATAACGGATCGTTACGATCGATAACG | 21036 |
| CGAACGATAACGGATCGTTACGATCGATAAC | 21037 |
| CGAACGATAACGGATCGTTACGATCGATAA | 21038 |
| CGAACGATAACGGATCGTTACGATCGATA | 21039 |
| CGAACGATAACGGATCGTTACGATCGAT | 21040 |
| CGAACGATAACGGATCGTTACGATCGA | 21041 |
| CGAACGATAACGGATCGTTACGATCG | 21042 |
| CGAACGATAACGGATCGTTACGATC | 21043 |
| CGAACGATAACGGATCGTTACGAT | 21044 |
| CGAACGATAACGGATCGTTACGA | 21045 |
| CGAACGATAACGGATCGTTACG | 21046 |
| CGAACGATAACGGATCGTTAC | 21047 |
| CGAACGATAACGGATCGTTA | 21048 |
| CGAACGATAACGGATCGTT | 21049 |
| CGAACGATAACGGATCGT | 21050 |
| CGAACGATAACGGATCG | 21051 |
| CGAACGATAACGGATC | 21052 |
| CGAACGATAACGGAT | 21053 |
| CGAACGATAACGGA | 21054 |
| CGAACGATAACGG | 21055 |
| CGAACGATAACG | 21056 |
| CGAACGATAAC | 21057 |
| CGAACGATAA | 21058 |
| CGAACGATA | 21059 |
| CGAACGAT | 21060 |
| CGAACGA | 21061 |
| CGAACG | 21062 |
| CGAAC | 21063 | b. Test Probe
c. Negative Probe

The probe may be a negative probe. The negative probe may comprise a nucleic acid sequence that is not present in the biological sample. The negative probe may be complementary to a miRNA*. The sequence of the negative probe may be selected from a sequence in Table 2 (SEQ ID NOs: 20863-20925).

TABLE 2

The Negative Control Probes

| SEQUNCE | SEQ ID NO |
|---|---|
| TGGAATGTAAAGAAGTATGTA | 20863 |
| AACCCGTAGATCCGAACTTGTG | 20864 |
| TACAGTACTGTGATAACTGAAG | 20865 |
| AGCAGCATTGTACAGGGCTATGA | 20866 |
| TCAAATGCTCAGACTCCTGT | 20867 |
| AAAAGTGCTTACAGTGCAGGTAGC | 20868 |
| TAAAGTGCTGACAGTGCAGAT | 20869 |
| AGCAGCATTGTACAGGGCTATCA | 20870 |
| TACCCTGTAGATCCGAATTTGTG | 20871 |
| TACCCTGTAGAACCGAATTTGT | 20872 |
| TGGAGTGTGACAATGGTGTTTGT | 20873 |
| TTAAGGCACGCGGTGAATGCCA | 20874 |
| TCCCTGAGACCCTTTAACCTGTG | 20875 |
| TCCCTGAGACCCTAACTTGTGA | 20876 |
| CATTATTACTTTTGGTACGCG | 20877 |
| TCGTACCGTGAGTAATAATGC | 20878 |
| TCACAGTGAACCGGTCTCTTTT | 20879 |
| TCACAGTGAACCGGTCTCTTTC | 20880 |
| CTTTTTGCGGTCTGGGCTTGC | 20881 |
| CAGTGCAATGTTAAAGGGCAT | 20882 |
| CAGTGCAATGATGAAAGGGCAT | 20883 |
| TAACAGTCTACAGCCATGGTCG | 20884 |
| TTGGTCCCCTTCAACCAGCTGT | 20885 |
| TTGGTCCCCTTCAACCAGCTA | 20886 |
| TGTGACTGGTTGACCAGAGGG | 20887 |
| TATGGCTTTTTATTCCTATGTGA | 20888 |
| TATGGCTTTTCATTCCTATGTG | 20889 |
| ACTCCATTTGTTTTGATGATGGA | 20890 |
| TATTGCTTAAGAATACGCGTAG | 20891 |
| AGCTGGTGTTGTGAATC | 20892 |
| TCTACAGTGCACGTGTCT | 20893 |
| AGTGGTTTTACCCTATGGTAG | 20894 |
| TAACACTGTCTGGTAAAGATGG | 20895 |

TABLE 2-continued

The Negative Control Probes

| SEQUNCE | SEQ ID NO |
|---|---|
| TGTAGTGTTTCCTACTTTATGGA | 20896 |
| CATAAAGTAGAAAGCACTAC | 20897 |
| TGAGATGAAGCACTGTAGCTCA | 20898 |
| TACAGTATAGATGATGTACTAG | 20899 |
| GTCCAGTTTTCCCAGGAATCCCTT | 20900 |
| TGAGAACTGAATTCCATGGGTT | 20901 |
| TGAGAACTGAATTCCATAGGCT | 20902 |
| GTGTGTGGAAATGCTTCTGC | 20903 |
| TCAGTGCACTACAGAACTTTGT | 20904 |
| TCAGTGCATCACAGAACTTTGT | 20905 |
| TCTGGCTCCGTGTCTTCACTCC | 20906 |
| TCTCCCAACCCTTGTACCAGTG | 20907 |
| ACTAGACTGAAGCTCCTTGAGG | 20908 |
| TCAGTGCATGACAGAACTTGGG | 20909 |
| TTGCATAGTCACAAAAGTGA | 20910 |
| AATCATACACGGTTGACCTATT | 20911 |
| TAGGTTATCCGTGTTGCCTTCG | 20912 |
| TTAATGCTAATCGTGATAGGGG | 20913 |
| TAGCAGCACATAATGGTTTGTG | 20914 |
| TAGCAGCACATCATGGTTTACA | 20915 |
| TAGCAGCACGTAAATATTGGCG | 20916 |
| ACTGCAGTGAAGGCACTTGT | 20917 |
| CAAAGTGCTTACAGTGCAGGTAGT | 20918 |
| AACATTCAACGCTGTCGGTGAGT | 20919 |
| AACATTCATTGCTGTCGGTGGG | 20920 |
| AACATTCAACCTGTCGGTGAGT | 20921 |
| AACATTCATTGTTGTCGGTGGGTT | 20922 |
| TGGTTCTAGACTTGCCAACTA | 20923 |
| TTTGGCAATGGTAGAACTCACA | 20924 |
| TATGGCACTGGTAGAATTCACTG | 20925 | d. Positive Probe

The probe may be a positive probe. The positive probe may be complementary to a small RNA. The small RNA may be present in an animal cell, such as a mammalian cell. The small RNA may be less than 200 nucleotides in length. The small RNA may be a ribosomal RNA. The sequence of the nucleic acid may be selected from a sequence in Table 3 (SEQ ID NOS: 20926-20937).

TABLE 3

The Positive Control Probes

| SEQUNCE | SEQ ID NO |
|---|---|
| TCAGAACGTGACAATCAGCACTAGCTATTGCTTGCTATT | 20926 |
| CAGTGAAGCAATGGCAATACTAGCTATTGCTTGCTATT | 20927 |
| TGCATCAGCGATCTTGGTGGTTAGCTATTGCTTGCTATT | 20928 |
| CTTCACTTACTGTCAGTAGCATAGCTATTGCTTGCTATT | 20929 |
| GAATTTGCGTGTCATCCTTGCGTAGCTATTGCTTGCTATT | 20930 |
| GAACCACCTCAGTAGTGTCTGTAGCTATTGCTTGCTATT | 20931 |
| GGTCAGAGCGCTGCGGTGATGTAGCTATTGCTTGCTATT | 20932 |
| AGACCTTCATGTTCAGTCAGCTAGCTATTGCTTGCTATT | 20933 |
| GCTAGCGCTGCGTTCTTCATCTAGCTATTGCTTGCTATT | 20934 |
| GCTTCCGAGATCAGACGAGATCTAGCTATTGCTTGCTATT | 20935 |
| TCTGTATCGTTCCAATTTAATGCTAGCTATTGCTTGCTATT | 20936 |
| GCGTGTCATCCTTGCGAATGCTAGCTATTGCTTGCTATT | 20937 | e. Spike Probe

The probe may be a spike probe. The spike probe may comprise a sequence that is not complementary to 20-100 consecutive nucleotides (e.g., 60) in a genome. The genome may be an animal genome or viral genome. The animal may be human, mouse or rat. The sequence of the spike probe may be selected from a sequence listed in Table 4 (SEQ ID NOS: 20938-20951).

TABLE 4

The Spikes

| SEQUNCE | SEQ ID NO |
|---|---|
| TATTATGCGCGTAGCGTACCGAATGCTAGCTATTGCTTGCTATT | 20938 |
| CGCGCATAATATCGGTACGCTAATGCTAGCTATTGCTTGCTATT | 20939 |
| CGAATCGCGTATATTATGCGCGATGCTAGCTATTGCTTGCTATT | 20940 |
| TTACGCGTACCTATATCGACCCATGCTAGCTATTGCTTGCTATT | 20941 |
| CGTCGACTATCTATATCGACCCATGCTAGCTATTGCTTGCTATT | 20942 |
| TATCGCGAACTCGCCCTATAACATGCTAGCTATTGCTTGCTATT | 20943 |
| ATATAAGTTCGTATAACTATCGATGCTAGCTATTGCTTGCTATT | 20944 |
| CGATTAGTATACGAACTTATATATGCTAGCTATTGCTTGCTATT | 20945 |
| CGTTTCGTACGTCGTCGATTCGATGCTAGCTATTGCTTGCTATT | 20946 |
| CGAATCGACGACGCGCATAATAATGCTAGCTATTGCTTGCTATT | 20947 |
| TTAGTATCGAATACTAATCGATATGCTAGCTATTGCTTGCTATT | 20948 |
| CGATTAGTATACGAACTTATATATGCTAGCTATTGCTTGCTATT | 20949 |
| ATATAAGTTCGTATAACTATCGATGCTAGCTATTGCTTGCTATT | 20950 |
| TTAGTATCGAATTCGATACTAAATGCTAGCTATTGCTTGCTATT | 20951 |

3. Biochip

A biochip is also provided. The biochip may comprise a solid substrate comprising an attached probe or plurality of probes described herein. The probes may be capable of hybridizing to a target sequence under stringent hybridization conditions. The probes may be attached at spatially defined address on the substrate. More than one probe per target sequence may be used, with either overlapping probes or probes to different sections of a particular target sequence. The probes may be capable of hybridizing to target sequences associated with a single disorder. The biochip may comprise a negative probe, a positive probe, a spike probe, a test probe, or a combination thereof.

The probes may be attached to the biochip in a wide variety of ways, as will be appreciated by those in the art. The probes may either be synthesized first, with subsequent attachment to the biochip, or may be directly synthesized on the biochip.

The solid substrate may be a material that may be modified to contain discrete individual sites appropriate for the attachment or association of the probes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, Teflon J, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. For example, probes may be placed on the inside surface of a tube, for flow-through sample analysis to minimize sample volume. Similarly, the substrate may be flexible, such as a flexible foam, including closed cell foams made of particular plastics.

The biochip and the probe may be derivatized with chemical functional groups for subsequent attachment of the two. For example, the biochip or probe may be derivatized with a chemical functional group including, but not limited to, aldehyde groups, amine groups, amino groups, carboxyl groups, epoxy, oxo groups or thiol groups. Using these functional groups, the probes may be attached using functional groups on the probes either directly or indirectly using a linkers. The probes may be attached to the solid support by either the 5'terminus, 3'terminus, or via an internal nucleotide. The probe may comprise a functional group, which may be a 5'amino modifier C12 or a 3'amino modifier C6.

The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography.

4. Method for Detecting a Target Nucleic Acid

A method is provided herein for detecting a target nucleic acid. FIG. 5 is a schematic representation of the method. The method may comprise using a probe (hereafter, "the probe") to specifically detect and distinguish a target nucleic acid (hereafter, "the target nucleic acid") from a substantially identical nucleic acid (hereafter, "the sibling nucleic acid"), wherein the sibling nucleic acid may differ from the target nucleic acid at a site that may include as few as one nucleotide (hereafter, "the variant site").

The probe, the target nucleic acid, and the sibling nucleic acid may each comprise a first portion and a second portion. The first portions of the target nucleic acid, the sibling nucleic acid, and the probe may all be located on the 5' end of each respective nucleic acid, or they may all be located on the 3' end of each respective nucleic acid. Conversely, the second portion of the target nucleic acid, the sibling nucleic acid, and the probe may all be located on the 3' end of each respective nucleic acid, or they may all be on the 5' end of each respective nucleic acid. The methods provided herein are based upon the strength of hybridization between the two portions of the probe and the corresponding two portions of the target nucleic acid, and between the two portions of the probe and the corresponding two portions of the sibling nucleic acid.

a. Target Nucleic Acid and Sibling Nucleic Acid

The first portion of the target nucleic acid may be substantially identical in sequence to the first portion of the sibling nucleic acid, differing at the variant site by as few as one nucleotide. The second portion of the target nucleic acid may be identical in sequence to the second portion of the sibling nucleic acid.

b. Interaction Between the Probe and the Target Nucleic Acid

The first portion of the probe and the first portion of the target nucleic acid may be complementary. The second portion of the probe and the second portion of the target nucleic acid may also be substantially complementary.

c. Interaction Between the Probe and the Sibling Nucleic Acid

The first portion of the probe and the first portion of the sibling nucleic acid may be substantially complementary. The second portion of the probe and the second portion of the sibling nucleic acid may be substantially complementary.

d. Distinguishing the Target Nucleic Acid from the Sibling Nucleic Acid Using the Probe While not being bound by theory, the substantial complementarity between the second portion of the probe and the second portion of the sibling nucleic acid may sensitize the probe to a mismatch between the first portion of the probe and the first portion of the sibling nucleic acid causing an overall effect of less efficient hybridization between the probe and the sibling nucleic acid. In contrast, the substantial complementarity between the second portion of the probe and the second portion of the target nucleic acid may cause the first portion of the probe to more efficiently bind to the complementary first portion of the target nucleic acid. The substantial complementarity between the first and second portions of the probe and sibling nucleic acid may result in an overall weaker hybridization between the probe and the sibling target nucleic acid compared to the hybridization between the probe and the target nucleic acid. The probe may thus specifically detect the target nucleic acid (of which the first portion is complementary to the first portion of the probe) and distinguish the target nucleic acid from the sibling nucleic acid. A method described herein may allow specific detection of the target nucleic acid in a diverse background of other substantially identical nucleic acids ranging in concentration from low to high.

e. Target Nucleic Acid

A method is provided herein for detecting a target nucleic acid in a sample, wherein the target nucleic acid may comprise a first portion and a second portion. The target nucleic acid may comprise an adaptor sequence. Adaptor sequences are well known in the art to be used for detecting and amplifying nucleic acids, such as in polymerase chain reactions.

f. Sibling Nucleic Acid

A method is provided herein for detecting a target nucleic acid, wherein the target nucleic acid may be distinguished from a sibling nucleic acid. The sibling nucleic acid may comprise a first portion and a second portion. The second portion of the sibling nucleic acid may be identical to the second portion of the target nucleic acid. The first portion of the sibling nucleic acid may be substantially identical to the first portion of the target nucleic acid. The first portion of the sibling nucleic acid may also comprise a variant site.

g. Variant Site

The first portion of the target nucleic acid may comprise a variant site. The first portion of the sibling nucleic acid may also comprise a variant site. The variant site may differ between the target nucleic acid and the sibling nucleic acid. The variant site may also differ among substantially identical sibling nucleic acids. The variant site may comprise by as few as one nucleotide. The variant site of the target nucleic acid may differ from the variant site of the nucleic acid by as few as one nucleotide.

(1) Gene Families

The target nucleic acid and the sibling nucleic acid may be members of the same gene family. The gene family may comprise a plurality of genes. The genes may be evolutionarily related (i.e., share a common ancestral gene). The genes may share common sequence motifs and structures. The genes may also be substantially identical in sequence. The sequences may comprise a variant site, which may differ among the genes of a gene family.

The genes may be RNA genes, which may encode ribozymes, rRNA, tRNAs, or miRNAs. For example, the human genes encoding miRNAs Let-7a and Let-7c differ in sequence by one nucleotide.

The gene family may also be a collection of genes encoding at least one polypeptide domain whose amino acid sequences have at least 25% sequence identity over a comparison window of at least 20 amino acids. Such domains may be related through common ancestry as a result of gene duplication or evolution. Many polypeptide domains are known in the art including, for example, the EGF domain, the immunoglobulin domain, the fibronectin type III domain, the cadherin-like domain, death effector domains (DED).

The gene family may encode polypeptides sharing at least one highly conserved region. Two polypeptides share a "highly conserved region" if the polypeptides have a sequence identity of at least 60% over a comparison window of five amino acids, or if they share a sequence identity of at least 50% over a comparison window of ten amino acids.

(2) Polymorphisms

The variant site may comprise a polymorphism. "Polymorphism" as used herein may mean the occurrence of two or more genetically determined alternative sequences or alleles in a population. The polymorphism may comprise one nucleotide (i.e., comprise a single nucleotide polymorphism, or SNP), which may be an A, C, G, T, or U. The polymorphism may also comprise a small insertion or deletion. The polymorphism may be associated with or cause a disease or condition. The polymorphism may also be associated with the response of an individual to an agent such as a pharmacotherapeutic. The polymorphism may occur in a coding or noncoding region of a gene, or in an intergenic region between genes. The polymorphism may be a mutation. The mutation may be a nonsynonymous (i.e., silent), or synonymous (e.g., missense, asense, or nonsense) mutation. The mutation may also result in a change in the splicing or regulation of a gene.

A polymorphic marker or site is the locus at which divergence occurs. Markers may have at least two alleles, each occurring at frequency of greater than 1%, and may occur at a frequency greater than 10% or 20% of a selected population. A polymorphism may comprise one or more base changes, an insertion, a repeat, or a deletion. A polymorphic locus may be as small as one base pair. Polymorphic markers may include restriction fragment length polymorphisms, variable number of tandem repeats (VNTRs), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wild type form. Diploid organisms may be homozygous or heterozygous for allelic forms. A diallelic polymorphism has two forms. A triallelic polymorphism has three forms. Single nucleotide polymorphisms (SNPs) may be included in polymorphisms.

Single nucleotide polymorphism (SNPs) are positions at which two alternative bases occur at appreciable frequency (>1%) in the human population, and are the most common type of human genetic variation. The site may be preceded by and followed by highly conserved sequences of the allele (e.g., sequences that vary in less than 1/100 or 1/1000 members of the populations). A single nucleotide polymorphism may arise due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms may also arise from a deletion of a nucleotide or an insertion of a nucleotide relative to a reference allele.

h. Probe

A method for detecting a target nucleic acid is provided herein wherein a probe specifically detects a target nucleic acid. The probe may comprise a first and second portion. The first portion of the probe may be complementary to the first portion of a target nucleic aid. The second portion of the probe may be substantially complementary to the second portion of the target nucleic acid. The probe may comprise 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50, 55, 60, 65, 70, 75, 80, 85, 90, 95, or 100 nucleotides that are complementary to the target nucleic acid. The probe may also be substantially complementary to the sibling nucleic acid. The probe may comprise 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50, 55, 60, 65, 70, 75, 80, 85, 90, 95, or 100 nucleotides that are complementary to the sibling nucleic acid.

The probe may have a melting temperature of 68-70° C. The probe may be used in an amplifying reaction. The reaction may be PCR. The PCR reaction may comprise a forward primer, a reverse primer, and the probe. The PCR reaction may comprise the probe and a reverse primer bound to the target nucleic acid in a complex wherein the 5' end of the probe may be located 5, 6, 7, 8, 9, 10 or 11 nucleotides upstream relative to the 3' end of the reverse primer.

The probe may also comprise a label. The probe may also comprise more than 2 nucleic acids. The probe may also comprise a minor groove binder.

(1) Detection Site

The first portion of the probe may comprise a detection site. The detection site may comprise one nucleotide. The detection site may also comprise a plurality of nucleotides. The detection site may be complementary to the variant site of a target nucleic acid. The detection site may also be non-complementary to the variant site of the sibling nucleic. The detection site may be located at either the 5' end or the 3' end of the probe. For example, the detection site may be 2, 3, 4, 5, 6, 7 or 8 bases from the 5' end of the probe, or the detection site may be 2, 3, 4, 5, 6, 7, or 8 bases from the 3' end of the probe. The detection site may be 8-10 nucleotides complementary to the target nucleic acid.

(2) Sensitizing Site

The second portion of the probe may comprise a sensitizing site. The sensitizing site may be noncomplementary to a target nucleic acid. The sensitizing site may also be non-complementary to the sibling nucleic acid. The sensitizing site may be distal to the detection site. The sensitizing site may sensitize the probe to an additional mismatch between the probe and the first portion of the sibling nucleic acid causing an overall effect of less efficient hybridization between the probe and the sibling nucleic acid. In contrast, the sensitizing site of the probe may cause the first portion of the probe to efficiently bind to the complementary first portion of the target nucleic acid for an overall effect of more efficient hybridization between the probe and the target nucleic acid. The sensitizing site may be located at any site position of the probe including the 5' end, the 3' end or anywhere in between the ends of the probe, but distal to the detection site. The sensitizing site may comprise one nucleotide. The sensitizing site may also comprise a plurality of nucleotides. The sensitizing site may comprise 1-20 nucleotides. The sensitizing site may also comprise a poly(A) binding region. The poly(A) binding region may be complementary to the poly(A) of a cDNA.

i. Background Nucleic Acid

Also provided herein is a method of specifically detecting a target nucleic acid and distinguishing the target nucleic acid from a background nucleic acid. The background nucleic acid may comprise a plurality of nucleic acids. The background nucleic acid may comprise a sibling nucleic acid. The background nucleic acid may also comprise a diversity of non-target nucleic acids and non-sibling nucleic acids. The background nucleic acid may be neither identical nor substantially identical to the target nucleic acid.

5. Methods of Making a Target Nucleic Acid

Methods of making a target nucleic acid are also provided. The target nucleic acid may comprise an adaptor sequence that is located in the second portion of the target nucleic acid. The adaptor sequence may be used to generate noncomplementarity between the second portion of a target nucleic acid and the second portion of a probe. The adaptor sequence may comprise a sequence that is non-complementary to the sensitizing site.

The adaptor sequence may comprise 12-30 nucleotides. The adaptor sequence may comprise a synthetic sequence. The adaptor sequence may also comprise a sequence that is nonidentical to any sequence in the genome of the animal from which the target nucleic acid is isolated. The adaptor sequence may be ligated to the target nucleic acid. The adaptor sequence may be added to the target nucleic acid by PCR. The PCR may comprise an adaptor primer comprising a sequence complementary to the adaptor sequence. The adaptor sequence may also comprise a poly(A) sequence.

a. Method of Generating a Target Nucleic Acid from RNA (1) RNA Extraction/Polyadenylation The target nucleic acid may be RNA. Methods for isolating and amplifying the target sequences of RNA include total RNA extraction, a polyadenylation reaction, and a reverse transcription (RT) reaction. The target RNA may be mRNA, tRNA, shRNA, siRNA, Piwi-interacting RNA, pri-miRNA, pre-miRNA, miRNA, or anti-miRNA. The RNA may be polyadenylated. Polyadenylation may be generated by a poly (A) polymerase. Polyadenylation may also be generated by using a poly(A) tailing kit. Polyadenylation may also be by the method of Shi and Chiang (Biotechniques, 2005; 39(4): 519-25), the contents of which are incorporated herein by reference. Polyadenylation may add 8, 9, 10, 11, 12, 13, 14, 15, 16, 17, 18, 19, 20, 30, 40, 50, 60, 70, 80, 90, 100, 110, 120, 130, 140, 150, 160, 170, 180, 190, 200, 210, 220, 230, 240, or 250 adenosines to the target nucleic acid.

(2) Reverse Transcription

Target sequences of a cDNA may be generated by reverse transcription of the target RNA. Methods for generating cDNA may be reverse transcribing polyadenylated RNA or alternatively, RNA with a ligated adaptor sequence. The cDNA may be synthesized according to methods outlined in U.S. patent Ser. No. 11/384,049, the contents of which are incorporated herein by reference.

(a) Reverse Transcription Using Adaptor Sequence Ligated to RNA

The RNA may be ligated to an adapter sequence prior to reverse transcription. A ligation reaction may be performed by T4 RNA ligase to ligate an adaptor sequence at the 3' end of the RNA. Reverse transcription (RT) reaction may then be performed using a primer comprising a sequence that is complementary to the 3' end of the adaptor sequence.

(b) Reverse Transcription Using Polyadenylated Sequence Ligated to RNA

Polyadenylated RNA may be used in a reverse transcription (RT) reaction using a poly(T) primer comprising a 5' adaptor sequence. The poly(T) sequence may comprise 8, 9, 10, 11, 12, 13, or 14 consecutive thymines. The reverse transcription primer may comprise one of the following sequences:

```
5' GCGAGCACAGAATTAATACGACTCACTACCCGTTTTTTTTTTT
VN 3'

5'-GCGAGCACAGAATTAATACGACTCACTACGCGTTTTTTTTTTVN-
3'

5'-GCGAGCACAGAATTAATACGACTCACTATAGGTTTTTTTTTTVN
-3'
where V = a mixture of A, C and G and N = a
mixture of all 4 nucleotides.
```

(3) RT-PCR of RNA

The reverse transcript of the RNA may be amplified by real time PCR, using a specific forward primer comprising at least 15 nucleic acids complementary to the target nucleic acid and a 5' tail sequence; a reverse primer that is complementary to the 3' end of the adaptor sequence; and a probe comprising at least 8 nucleic acids complementary to the target nucleic acid. The probe may be partially complementary to the 5' end of the adaptor sequence.

b. PCR of Target Nucleic Acids

Methods of amplifying target nucleic acids are described herein. The amplification may be by a method comprising PCR. The first cycles of the PCR reaction may have an annealing temp of 56° C., 57° C., 58° C., 59° C., or 60° C. The first cycles may comprise 1-10 cycles. The remaining cycles of the PCR reaction may be 60° C. The remaining cycles may comprise 2-40 cycles. The annealing temperature may cause the PCR to be more sensitive. The PCR may generate longer products that can serve as higher stringency PCR templates.

(1) Forward Primer

The PCR reaction may comprise a forward primer. The forward primer may comprise 15, 16, 17, 18, 19, 20, or 21 nucleotides identical to the target nucleic acid.

The 3' end of the forward primer may be sensitive to differences in sequence between a target nucleic acid and a sibling nucleic acid.

The forward primer may also comprise a 5' overhanging tail. The 5' tail may increase the melting temperature of the forward primer. The sequence of the 5' tail may comprise a sequence that is non-identical to the genome of the animal from which the target nucleic acid is isolated. The sequence of the 5' tail may also be synthetic. The 5' tail may comprise 8, 9, 10, 11, 12, 13, 14, 15, or 16 nucleotides. The 5' overhanging tail may comprise the sequence 5'-ACACTCCAGCTGGG-3'. The 5' overhanging tail may also comprise the sequence 5'-CAGTCATTTGGG-3'. The forward primer may comprise a sequence corresponding to the sequence of a SEQ ID NO in the "FD-P" column of Table 7.

(2) Reverse Primer

The PCR reaction may comprise a reverse primer. The reverse primer may be complementary to a target nucleic acid. The reverse primer may also comprise a sequence complementary to an adaptor sequence. The sequence complementary to an adaptor sequence may comprise 12-24 nucleotides. The reverse primer may comprise the sequence

```
5'-GCGAGCACAGAATTAATACGAC-3'.
```

6. Expression Analysis of Diseases and Conditions

Also provided herein is a method of identifying a target nucleic acid associated with a disease or pathological condition. The target nucleic acid may comprise a variant site. The variant site may be associated with a disease, pathological condition, or trait. The trait may be any identifiable state, such as color, height, size, or predisposition. The method may comprise contacting the target nucleic acid with a probe. The level of the probe binding to the target nucleic acid compared to a control may be indicative of a disease, pathological condition, or trait.

For example, detecting the level (or expression level) of a target nucleic acid compared to a control may provide a high-resolution, high-sensitivity dataset, which may be used in the areas of diagnostics, prognostics, therapeutics, drug development, pharmacogenetics, biosensor development, and other related areas.

An expression profile generated by the current method may be a "fingerprint" of the state of the sample with respect to a number of target nucleic acids. While two states may have any particular target nucleic acid similarly expressed, the evaluation of a number of target nucleic acids simultaneously allows the generation of a gene expression profile that is characteristic of the state of the cell. That is, normal tissue may be distinguished from diseased tissue. By comparing expression profiles of tissue in known different disease states, information regarding which target nucleic acids are associated in each of these states may be obtained. Then, diagnosis may be performed or confirmed to determine whether a tissue sample has the expression profile of normal or disease tissue. This may provide for molecular diagnosis of related conditions.

The expression level of a disease-associated target nucleic acid is information in a number of ways. For example, a differential expression of a disease-associated target nucleic acid compared to a control may be used as a diagnostic that a patient suffers from the disease. Expression levels of a disease-associated target nucleic acid may also be used to monitor the treatment and disease state of a patient. Furthermore, expression levels of a disease-associated target nucleic acid may allow the screening of drug candidates for altering a particular expression profile or suppressing an expression profile associated with disease.

A target nucleic acid may be detected and levels of the target nucleic acid measured by contacting a sample comprising the target nucleic acid with a probe sufficiently complementary to the target nucleic acid and detecting hybridization to the probe above control levels.

The target nucleic acid may be detected by immobilizing the target nucleic acid to be examined on a solid support such as nylon membranes and hybridizing a labeled probe with the sample. The target nucleic acid may be detected by immobilizing a labeled probe to a solid support and hybridizing a sample comprising a labeled target nucleic acid. Following washing to remove the non-specific hybridization, the label may be detected.

The target nucleic acid may be detected in a biological sample according to the methods outlined in U.S. patent Ser. No. 11/384,049, the contents of which are incorporated herein by reference.

The target nucleic acid may also be detected in situ by contacting permeabilized cells or tissue samples with a labeled probe to allow hybridization with the target nucleic acid. Following washing to remove the non-specifically bound probe, the label may be detected.

These assays can be direct hybridization assays or can comprise sandwich assays, which include the use of multiple probes, as is generally outlined in U.S. Pat. Nos. 5,681,702; 5,597,909; 5,545,730; 5,594,117; 5,591,584; 5,571,670; 5,580,731; 5,571,670; 5,591,584; 5,624,802; 5,635,352; 5,594,118; 5,359,100; 5,124,246; and 5,681,697, each of which is hereby incorporated by reference.

A variety of hybridization conditions may be used, including high, moderate and low stringency conditions as outlined above. The assays may be performed under stringency conditions which allow hybridization of the probe only to the target. Stringency can be controlled by altering a step parameter that is a thermodynamic variable, including, but not limited to, temperature, formamide concentration, salt concentration, chaotropic salt concentration pH, or organic solvent concentration.

Hybridization reactions may be accomplished in a variety of ways. Components of the reaction may be added simultaneously, or sequentially, in different orders. In addition, the reaction may include a variety of other reagents. These include salts, buffers, neutral proteins, e.g., albumin, detergents, etc. which may be used to facilitate optimal hybridization and detection, and/or reduce non-specific or background interactions. Reagents that otherwise improve the efficiency of the assay, such as protease inhibitors, nuclease inhibitors and anti-microbial agents may also be used as appropriate, depending on the sample preparation methods and purity of the target.

a. Diagnostic

A method of diagnosis is also provided. The method may comprise detecting a differential expression level of disease-associated target nucleic acid in a biological sample. The sample may be derived from a patient. Diagnosis of a disease state in a patient may allow for prognosis and selection of therapeutic strategy. Further, the developmental stage of cells may be classified by determining temporarily expressed disease-associated target nucleic acids.

In situ hybridization of labeled probes to tissue arrays may be performed. When comparing the fingerprints between an individual and a standard, the skilled artisan may make a diagnosis, a prognosis, or a prediction based on the findings. It is further understood that the genes, which indicate the diagnosis, may differ from those, which indicate the prognosis. In addition, molecular profiling of the condition of the cells may lead to distinctions between responsive or refractory conditions or may be predictive of outcomes. For example, the method of diagnosing may comprise detecting differential levels of cancer-associated target nucleic acids in a biological sample. The source of cancer-associated target nucleic acids may be from a cancer cell characterized by unregulated cell-growth. A cancer cell may include cells arising from breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, and brain cancer.

b. Genotyping

Also provided herein is a method for genotyping using a probe described herein to detect a polymorphism such as a SNP. "Genotyping" used herein may be the determination of the genetic information an individual carries at one or more positions in the genome. For example, genotyping may comprise determining which allele or alleles an individual carries for a single SNP or determining which allele or alleles an individual carries for a plurality of SNPs. A genotype may be the identity of the alleles present in an individual at one or more polymorphic sites.

(1) Human Diseases and Conditions

Genotyping may be for measuring the predisposition of a human for a disease or condition. For example, genotyping may be used as described in U.S. Pat. No. 7,127,355, the contents of which are incorporated herein by reference. Genotyping may also be used to predict the response of an individual to a pharmacotherapeutic or other treatment.

(2) Viral RNA

Genotyping may also be for detecting the presence of a mutation in a viral genome such as HIV, Hepatitis B Virus, or Human papilloma virus. Examples of such genotyping may be found in U.S. Pat. Nos. 6,797,464 and 6,653,081, and U.S. Patent Pub. Nos. 20050112554 and 2005014379, the contents of which are incorporated herein by reference.

(3) Bacterial Pathogenesis

Genotyping may also be for detecting bacterial strains and mutations, such bacterial antibiotic resistance. For example, genotyping may be as described in U.S. Pat. No. 6,913,753, the contents of which are described herein by reference.

7. Drug Screening

A method of screening therapeutics is also provided. The method comprises contacting a pathological cell capable of expressing a disease related nucleic acid with a candidate therapeutic and evaluating the effect of a drug candidate on the expression profile of the disease associated target nucleic acid. Having identified the differentially expressed target nucleic acid, a variety of assays maybe executed. Test compounds may be screened for the ability to modulate gene expression of the disease associated nucleic acid. Modulation includes both an increase and a decrease in gene expression.

The test compound or drug candidate may be any molecule, e.g., protein, oligopeptide, small organic molecule, polysaccharide, polynucleotide, etc., to be tested for the capacity to directly or indirectly alter the disease phenotype or the expression of the disease associated nucleic acid. Drug candidates encompass numerous chemical classes, such as small organic molecules having a molecular weight of more than 100 and less than about 500, 1,000, 1,500, 2,000 or 2,500 daltons. Candidate compounds may comprise functional groups necessary for structural interaction with proteins, particularly hydrogen bonding, and typically include at least an amine, carbonyl, hydroxyl or carboxyl group, preferably at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Combinatorial libraries of potential modulators may be screened for the ability to bind to the disease associated nucleic acid or to modulate the activity thereof. The combinatorial library may be a collection of diverse chemical compounds generated by either chemical synthesis or biological synthesis by combining a number of chemical building blocks such as reagents.

Preparation and screening of combinatorial chemical libraries is well known to those of skill in the art. Such combinatorial chemical libraries include, but are not limited to, peptide libraries encoded peptides, benzodiazepines, diversomers such as hydantoins, benzodiazepines and dipeptide, vinylogous polypeptides, analogous organic syntheses of small compound libraries, oligocarbamates, and/or peptidyl phosphonates, nucleic acid libraries, peptide nucleic acid libraries, antibody libraries, carbohydrate libraries, and small organic molecule libraries.

8. Gene Silencing

A method of reducing expression of a target gene in a cell, tissue or organ is also provided. Expression of the target gene may be reduced by expressing a nucleic acid described herein that comprises a sequence substantially complementary to one or more binding sites of the target mRNA. The nucleic acid may be a miRNA or a variant thereof. The nucleic acid may also be pri-miRNA, pre-miRNA, or a variant thereof, which may be processed to yield a miRNA. The expressed miRNA may hybridize to a substantially complementary binding site on the target mRNA, which may lead to activation of RISC-mediated gene silencing. An example for a study employing over-expression of miRNA is Yekta et al 2004, Science 304-594, which is incorporated herein by reference. One of ordinary skill in the art will recognize that the nucleic acids described herein may also be used to inhibit expression of target genes or inhibit activity of miRNAs using antisense methods well known in the art, as well as RNAi methods described in U.S. Pat. Nos. 6,506,559 and 6,573,099, which are incorporated by reference.

The target of gene silencing may be a protein that causes the silencing of a second protein. By repressing expression of the target gene, expression of the second protein may be increased. Examples for efficient suppression of miRNA expression are the studies by Esau et al 2004 JBC 275-52361; and Cheng et al 2005 Nucleic Acids Res. 33-1290, which is incorporated by reference.

9. Gene Enhancement

A method of increasing expression of a target nucleic acid in a cell, tissue or organ is also provided. Expression of the target nucleic acid may be increased by expressing a nucleic acid described herein that comprises a sequence substantially complementary to a pri-miRNA, pre-miRNA, miRNA or a variant thereof. The nucleic acid may be an anti-miRNA. The anti-miRNA may hybridize with a pri-miRNA, pre-miRNA or miRNA, thereby reducing its gene repression activity. Expression of the target nucleic acid may also be increased by expressing a nucleic acid that is substantially complementary to a portion of the binding site in the target gene, such that binding of the nucleic acid to the binding site may prevent miRNA binding.

10. Therapeutic

A method of modulating a disease or disorder associated with developmental dysfunctions is also provided. The disease or disorder may be cancer, such as prostate or liver cancer. In general, the nucleic acid molecules described herein may be used as a modulator of the expression of genes which are at least partially complementary to said nucleic acid. Further, miRNA molecules may act as target for therapeutic screening procedures, e.g. inhibition or activation of miRNA molecules might modulate a cellular differentiation process, e.g. proliferation or apoptosis. Furthermore, existing miRNA molecules may be used as starting materials for the manufacture of sequence-modified miRNA molecules, in order to modify the target-specificity thereof, e.g. an oncogene, a multidrug-resistance gene or another therapeutic target gene. Further, miRNA molecules can be modified, in order that they are processed and then generated as double-stranded siRNAs which are again directed against therapeutically relevant targets. Furthermore, miRNA molecules may be used for tissue reprogramming procedures, e.g. a differentiated cell line might be transformed by expression of miRNA molecules into a different cell type or a stem cell.

11. LUMINEX® Method of Detection

The method of detecting target nucleic acids or miRNAs includes a number of steps discussed herein. Total RNA is extracted from tissue. The short RNAs fraction is enriched using a YM 100 column. The small RNA fraction may be labeled utilizing different methods (e.g., biotinylation). In parallel, miRNA antisense DNA or locked nucleic acid (LNA) probes with an amine-modification may be coupled to carboxylated color-coded LUMINEX® microspheres (beads) using EDC to make coupled bead mixtures, with each mixture containing as many as 100 different miRNA probes, each probe coupled to a bead with a different specific spectral signature or color. Beads may be prepared as a set of 100 distinct kinds that can be differentially detected by the LUMINEX® analyzer. The labeled miRNAs may then hybridized to mixtures of probe-bound color beads. The hybridized miRNA-coupled bead mixture may be treated with streptavidin-R-phycoerythrin dye. The reaction may be analyzed using the LUMINEX® analyzer. Lasers excite the internal dyes that identify each microsphere particle, as well as the reporter dye that is bound to the miRNA. The median intensity of the dye on each bead may be proportional to expression of the specific RNA in the tissue.

MiRNAs or probes or target nucleic acids may be labeled as follows:

12. Direct labeling a. Chemical Labeling

Examples include ULS technology, using part of a PerkinElmer Micromax kit for biotinylation of miRNA. This method labels miRNAs with biotins along their lengths, and was found to be reproducible and robust.

b. Kreatech Chemical Labeling Kit

This method labels miRNA or probes or target nucleic acids with biotin with a similar technology as PerkinElmer, but was shown to be somewhat less sensitive.

c. Enzymatic End Labeling

Examples include ligation of dinucleotides with a biotin entity (pCU-bio).

13. Signal Amplification a. TSA

Tyramide signal amplification (TSA) amplifies the number of biotins in site, starting from one biotin to which a Streptavidin-horse radish peroxidase (HRP) conjugate is bound. The Tyramide biotin substrate is processed by the HRP to produce a non soluble biotin that is precipitated in site, creating a cluster of biotins on the appropriate microsphere.

b. Genisphere

The method utilizes a 3DNA system of branched DNA that has a large number of bound biotin molecules, and is useful for detecting miRNAs when only low amounts of starting material are available.

14. Transcription a. Direct Transcript

This method generates transcripts labeled with biotin for linear amplification of the RNA. This method may generated transcripted labeled with biotin from target nucleic acids.

b. SenseAmp Plus

This method uses amplification of miRNA using a Genisphere kit. Multiple aspects are described herein, illustrated by the following non-limiting examples.

15. Possible Applications

Small RNA proofing using the LUMINEX® technology is a fast and reliable technology and may be applied in high throughput manner to many samples at once. This system is highly sensitive and specific, thus may be applied to a large range of validations and profiling of miRNA or target nucleic acids for basic biological research, diagnostics and therapeutics. The high reproducibility of the technology makes it highly reliable.

The methods provided herein may be used for validation of newly predicted miRNA in the cell. It may also be used for validation and expression profiling of other short RNAs. It may also be used for validation of expression level of transfected siRNA (inhibitory RNA) expression in cells in therapeutic or research applications. It may also be used for expression proofing of miRNA in cells, tissues and body fluids for: discovery of miRNA differentiation in cancer and normal cells, early detection of cancer cells in body fluids and biopsies, prognosis of cancer stage, prediction of potential survival and response to treatments, determining tissue origin of metastasis carcinoma, for assigning appropriate anti-cancerous treatment, or for screening for potential therapeutic compounds. It may also be used for profiling miRNA in embryonic samples for the study of tissue development and differentiation.

16. Kits

A kit is also provided and may comprise a nucleic acid described herein together with any or all of the following: assay reagents, buffers, probes and/or primers, and sterile saline or another pharmaceutically acceptable emulsion and suspension base. In addition, the kits may include instructional materials containing directions (e.g., protocols) for the practice of the methods described herein.

For example, the kit may be a kit for the amplification, detection, identification or quantification of a target nucleic acid sequence. The kit may comprise a poly(T) primer, a forward primer, a reverse primer, and a probe.

EXAMPLES

Example 1

Methods of Generating a Target Nucleic Acid

A method for generating a target nucleic acid from miRNA is described below. Total RNA was isolated and extracted from cultured CHO cells. An adaptor sequence was generated using polyadenylation or an adaptor sequence was ligated to an adapter sequence prior to reverse transcription. A ligation reaction was then performed by T4 RNA ligase to ligate an adaptor sequence at the 3' end of the RNA.

Reverse transcription (RT) reaction was performed using a primer comprising a sequence that is complementary to the 3' end of the adaptor sequence. The reverse transcription primer (oligodT primer) was chosen from one of the following sequences:

```
                                          (SEQ ID NO 20836)
5'-GCGAGCACAGAATTAATACGACTCACTACCCGTTTTTTTTTTTVN-
3'

(SEQ ID NO 20837)
5'-GCGAGCACAGAATTAATACGACTCACTATCGGTTTTTTTTTTTVN-
3'

(SEQ ID NO 20853)
5'-GCGAGCACAGAATTAATACGACTCACTACCCGTTTTTTTTTTVN-3'

(SEQ ID NO 20854)
5'-GCGAGCACAGAATTAATACGACTCACTATCCGTTTTTTTTTTTVN-
3'

(SEQ ID NO 20855)
5'-GCGAGCACAGAATTAATACGACTCACTATCCCTTTTTTTTTTTVN-
3'

(SEQ ID NO 20856)
5'-GCGAGCACAGAATTAATACGACTCACTATCCGTTTTTATTTTTVN-
3'

(SEQ ID NO 20857)
5'-GCGAGCACAGAATTAATACGACTCACTATAGGTTTTTTTTTTTVN-
3'

(SEQ ID NO 20858)
5'-GCGAGCACAGAATTAATACGACTCACTATCCGATTTTTTTTTTVN-
3'
``` where V=a mixture of A, C and G and N=a mixture of all 4 nucleotides. The reverse transcript of the RNA was amplified by real time PCR reaction, using a specific forward primer that is complementary to the target nucleic acid and a 5' tail sequence. The forward primers was chosen from the sequences of 5' CAGTCATTTGGG 3' (SEQ ID NO 20839) or the corresponding to the sequence of a SEQ ID NO in the "FD-P" column of Table 7.

A reverse primer was also chosen that is complementary to the 5' end of the adaptor sequence. The reverse primer was 5'-GCGAGCACAGAATTAATACGAC-3' (SEQ ID NO 20859). The probe was partially complementary to the 3' end of the adaptor sequence.

PCR was then performed. The first cycles of the PCR reaction had an annealing temp of 58° C. The first cycles are 5 cycles. The remaining cycles of the PCR reaction was 60° C. The remaining cycles was 35 cycles. A target nucleic acid was generated from the methods describe above with the sequence 5'-TGAGGTAGTAGGTTGTATAGTT-3' (SEQ ID No: 20840)

Example 2

Probes for Detecting a Target Nucleic Acid

Probes for detecting a target nucleic acid are described herein. The probe to a polyadenylated cDNA was generated with the sequence 5'-CCGTTTTTTTTTTTT-3' (SEQ ID No: 20845). This sequence was then followed by a sequence complementary to target binding region to ensure the probe was partially complementary to the 3' end of the adaptor sequence of the target nucleic acid. The synthetic target binding region had three variations, with each variation shifted by one nucleotide relative to the target nucleic acid.

The three variations of probes were used that were capable of binding to a target nucleic acid comprising the sequence 5'-TGAGGTAGTAGGTTGTATAGTT-3' (SEQ ID No: 20840) comprised the following sequences:

```
Probe_v1
5'-CCGTTTTTTTTTTTTAACTATAC-3'    (SEQ ID No: 20846)

Probe_v2
5'-CCGTTTTTTTTTTTTACTATACA-3'    (SEQ ID No: 20847)

Probe_v3
5'-CCGTTTTTTTTTTTCTATACAA-3'     (SEQ ID No: 20848)
```

The sequence of the target binding region cannot have a 3' terminal 'A.' For example, the three variations of probes capable of binding to a target nucleic acid comprising the sequence 5'-TGATTGGTACGTCTGTGGGTAGA-3' (SEQ ID No: 20849) comprise the following sequences:

```
Probe_v1
5'-CCGTTTTTTTTTTTTCTACCCAC-3'    (SEQ ID No: 20850)

Probe_v2
5'-CCGTTTTTTTTTTTTACCCACAG-3'    (SEQ ID No: 20851)

Probe_v3
5'-CCGTTTTTTTTTTTCCCACAGA-3'     (SEQ ID No: 20852)
```

The probes also could be designed with sequence corresponding to a sequence of a SEQ ID NO in the "Probe1," "Probe2," or "Probe3" columns of Table 7.

Example 3

Detecting a Single Nucleotide Difference: Let-7a Versus Let-7d

Members of the human Let-7 family of miRNAs that only differ by one nucleotide were detected using the method described in Example 1. The sequences of two members of this family were as follows:

```
                                         (SEQ ID NO: 20840)
hsa-Let-7a   5'-UGAGGUAGUAGGUUGUAUAGUU-3'

(SEQ ID NO: 20841)
hsa-Let-7c   5'-UGAGGUAGUAGGUUGUAUGGUU-3'

(SEQ ID NO: 20842)
hsa-Let-7d   5'-AGAGGUAGUAGGUUGCAUAGU-3'
```

A minor groove binder (MGB) probe with (i) a 5'-CCG sequence that had no mismatch to the adaptor sequence of the reverse transcription primer as described above (i.e., 0 mismatch), and (ii) that was perfectly-matched to Let-7a at its 3' end was used in real time PCR (FIG. 3). Quantification of the 0 mismatch probe during real time PCR revealed that Let-7a miRNA was not distinguishable from Let-7c. This was demonstrated by the similar cycle thresholds ($C_T$) observed for Let-7a and Let-7c, which were 23.43 and 23.73, respectively, at a concentration of 3.50E-05 ng/µl (Table 7).

However, using a Let-7a-specific MGB probe with one mismatch to the adaptor sequence (FIG. 4) enabled the distinction between Let-7a and Let-7c via real time PCR, as shown by the difference in their corresponding $C_T$ (Table 7). The $C_T$ for Let-7a and Let-7c as detected by the one mismatch Let-7a-specific probe were 28.3 and not detected (ND) after 40 cycles, respectively, at a concentration of 3.50E-05 ng/µl.

The high specificity remained even when very similar miRNAs were mixed (Let-7a, Let-7c and Let-7d). As shown in Table 8A, the detected $C_T$ in the mixture was almost identical to the one detected for each of the miRNAs separately.

The above-described method was also successfully tested using a Let-7a-specific MGB probe with two 5' mismatches to the adaptor sequence. As shown in Table 7, use of the two mismatch Let-7a-specific probe enabled differential detection of Let-7a and Let-7c at a concentration of 3.50E-04 ng/µl, but increased the $C_T$ compared to the one mismatch Let-7a-specific probe.

TABLE 5

Detection of the Let-7 family members by a Let-7a probe

| | | $C_T$ | | |
|---|---|---|---|---|
| RNA | Conc. (ng/µl) | 2 mismatch | 1 mismatch | 0 mismatch |
| Let-7a | 3.50E−04 | 25.15 | 23.87 | 19.58 |
| | 3.50E−05 | 29.35 | 28.27 | 23.43 |
| | 3.50E−06 | 32.65 | 31.60 | 26.77 |
| Let-7c | 3.50E−04 | 33.81 | 31.89 | 19.92 |
| | 3.50E−05 | ND | ND | 23.73 |
| | 3.50E−06 | ND | ND | 27.02 |
| Let-7d | 3.50E−04 | 30.50 | 29.63 | 27.03 |
| | 3.50E−05 | 35.02 | 34.16 | 30.08 |
| | 3.50E−06 | 37.91 | 37.17 | 33.22 |

Table 6A also shows that a Let-7c-specific probe be with one mismatch compared to the adaptor sequence, detects Let-7c with a $C_T$ lower than that for Let-7a or Let-7d, therefore demonstrating an ability to distinguish between Let-7c and its other family members. Likewise, a 1 mismatch Let-7d-specific probe detected Let-7d at a lower $C_T$ compared to Let-7a or Let-7c.

TABLE 6a

A Detection of the Let-7 family members by Let-7 family probes

| RNA | Fwd primer: Let-7a MGB probe: Let-7a | | Fwd primer: Let-7d MGB probe: Let-7d | | Fwd primer: Let-7c MGB probe: Let-7c | |
|---|---|---|---|---|---|---|
| | Conc. (ng/µl) | $C_T$ 1 mismatch | RNA Conc. (ng/µl) | $C_T$ 1 mismatch | RNA Conc. (ng/µl) | $C_T$ 1 mismatch |
| Let-7a | 3.5E−04 | 25.42 | Let-7a 3.5E−04 | 32.48 | Let-7a 3.5E−04 | 38.65 |
| | 3.5E−05 | 29 | 3.5E−05 | 35.9 | 3.5E−05 | ND |
| | 3.5E−06 | 32.57 | 3.5E−06 | 38.59 | 3.5E−06 | ND |
| Let-7c | 3.5E−04 | 36.08 | Let-7c 3.5E−04 | ND | Let-7c 3.5E−04 | 25.17 |
| | 3.5E−05 | ND | 3.5E−05 | ND | 3.5E−05 | 31.11 |
| | 3.5E−06 | ND | 3.5E−06 | ND | 3.5E−06 | 32.81 |
| Let-7d | 3.5E−04 | 31.99 | Let-7d 3.5E−04 | 20.76 | Let-7d 3.5E−04 | ND |
| | 3.5E−05 | 35.88 | 3.5E−05 | 24.54 | 3.5E−05 | ND |
| | 3.5E−06 | ND | 3.5E−06 | 27.83 | 3.5E−06 | ND |
| Mix: Let7 a + c + d | 3.5E−04 | 25.49 | Mix: 3.5E−04 | 20.72 | Mix: 3.5E−04 | 25.18 |
| | 3.5E−05 | 28.85 | Let7 3.5E−05 | 24.29 | Let7 3.5E−05 | 31.18 |
| | 3.5E−06 | 33.52 | a + c + d 3.5E−06 | 27.84 | a + c + d 3.5E−06 | 32.67 |

The above-described method was also successfully tested using oligodT primers comprising a mismatch to the cDNA adaptor sequence at different positions as indicated in Table 6B (SEQ ID NOS 20853-20856).

The results described in Table 5 and Table 6A-B demonstrate that real time PCR using a probe or oligodT primers as described herein is capable of differentially detecting target nucleic acids that differ in sequence by a few as one nucleotide.

EXAMPLE 20

Detecting a Single Nucleotide Difference: miR-99a Versus miR-100

The single nucieotide difference between the miRNAs miR-99a and miR-100 was also detected using real time PCR using a method similar to that described in Examples 1 and 2. The sequences of the miRNAs were as follows:

TABLE 6B

Detection of the Let-7 family members by using oligidT primers comprising a mismatch at different positions

| | synthetic miRNA target | | | | | | | | |
|---|---|---|---|---|---|---|---|---|---|
| | let-7a | | | let-7c | | | let-7d | | |
| | 3.5E-04 | 3.5E-05 | 3.5E-06 | 3.5E-04 | 3.5E-05 | 3.5E-06 | 3.5E-04 | 3.5E-05 | 3.5E-06 |
| Adaptor: GCGAGCACAGAATTAATACGACTCACTATCGGTTTTTTTTTTTVN SEQ ID NO. 20837 | | | | | | | | | |
| let-7a | 26.1 | 29.44 | 33.64 | ND | ND | ND | 30.42 | 34.27 | 38.4 |
| let-7c | 47.38 | ND | ND | 26.86 | 32.58 | 36.72 | ND | ND | ND |
| let-7d | 32.04 | 35.94 | 39.49 | ND | ND | ND | 20.72 | 24.5 | 28.06 |
| Adaptor: GCGAGCACAGAATTAATACGACTCACTATCGGTTTTTTTTTTTVN SEQ ID NO. 20837 | | | | | | | | | |
| let-7a | 25.42 | 29 | 32.57 | 36.08 | ND | ND | 31.99 | 35.88 | 41.13 |
| let-7c | 38.65 | ND | ND | 25.17 | 31.11 | 32.81 | 45.8 | ND | ND |
| let-7d | 32.48 | 35.9 | 38.59 | ND | ND | ND | 20.76 | 24.54 | 27.83 |
| Adaptor: GCGAGCACAGAATTAATACGACTCACTATCCCTTTTTTTTTTTVN SEQ ID NO. 20855 | | | | | | | | | |
| let-7a | 26.6 | 30.49 | 34.85 | ND | ND | 43.17 | 30.37 | 34.86 | 39.22 |
| let-7c | ND | ND | ND | 26.66 | 32.48 | 34.65 | ND | ND | ND |
| let-7d | 32.01 | 35.87 | 39.67 | ND | ND | ND | 21.01 | 24.84 | 27.77 |
| Adaptor: GCGAGCACAGAATTAATACGACTCACTATCCGTTTTTATTTTTTVN SEQ ID NO. 20856 | | | | | | | | | |
| let-7a | 29.72 | 36.16 | 38.86 | ND | ND | ND | ND | ND | ND |
| let-7c | ND | ND | ND | 32.01 | ND | ND | ND | ND | ND |
| let-7d | 33.08 | 39 | 41.68 | ND | ND | ND | 22.47 | 26.19 | 29.08 |
| Adaptor: GCGAGCACAGAATTAATACGACTCACTATCCGATTTTTTTTTTVN SEQ ID NO. 20858 | | | | | | | | | |
| let-7a | 24.54 | 29.43 | 33.08 | ND | ND | ND | 31.67 | 34.87 | 37.23 |
| let-7c | ND | ND | ND | 26.13 | 33.13 | 35.55 | ND | ND | ND |
| let-7d | 31.01 | 35.21 | 37.93 | ND | ND | ND | 21.34 | 24.3 | 27.53 | miR-99a:  5'-AACCCGUAGAUCCGAUCUUGUG-3'  (SEQ ID NO: 20843)

miR-100:  5'-AACCCGUAGAUCCGAACUUGUG-3'  (SEQ ID NO: 20844)

As shown in Table 9, a probe with 1 mismatch to the cDNA adaptor sequence, but no mismatch compared to miR-99a recognized miR-99 at a $C_T$~9 cycles lower compared to miR-100, at the same RNA concentration.

Conversely, a probe with 1 mismatch to the cDNA adaptor sequence, but no mismatch to miR-100 recognized miR-100 at a $C_T$ which was about 5 cycles lower than the $C_T$ detected for miR-99. The high specificity of the method of the present invention remains even when these very similar miRNAs were mixed together (Table 7).

TABLE 7

Detection of hsa-miR-99a and hsa-miR-100

| RNA | Fwd primer: hsa-miR-99 MGB probe: miR-99 | | RNA | Fwd primer: hsa-miR-100 MGB probe: miR-100 | |
|---|---|---|---|---|---|
| | Amount (fmole) | $C_T$ | | Amount (fmole) | $C_T$ |
| miR-99a | 1.00E−02 | 26.42 | miR-99a | 1.00E−02 | 30.85 |
| | 2.50E−04 | 28.05 | | 2.50E−04 | 32.03 |
| | 6.25E−05 | 30.27 | | 6.25E−05 | 34.05 |
| | 1.56E−05 | 32.26 | | 1.56E−05 | 35.99 |
| miR-100 | 1.00E−02 | 35.49 | miR-100 | 1.00E−02 | 24.78 |
| | 2.50E−04 | 37.46 | | 2.50E−04 | 26.99 |
| | 6.25E−05 | 39.33 | | 6.25E−05 | 29.27 |
| | 1.56E−05 | 40.97 | | 1.56E−05 | 31.89 |
| Mix: | 1.00E−02 | 27.13 | Mix: | 1.00E−02 | 27.82 |
| miR-99 + | 2.50E−04 | 29.2 | miR-99 + | 2.50E−04 | 29.78 |
| miR-100 | 6.25E−05 | 31.57 | miR-100 | 6.25E−05 | 31.88 |
| | 1.56E−05 | 34.09 | | 1.56E−05 | 34.26 |

Example 5

Sensitivity for Detecting a Target Nucleic Acid

The sensitivity of real time PCR was also tested. hsa-miR-122a, which is a liver specific miRNA, was amplified from different RNA sources (brain, liver and Hela cells, or mixtures thereof) by real time reverse transcription-PCR, according to the method described in Examples 1 and 2 using a miR-122a-specific probe. The initial RNA amount per reverse transcription reaction was 0.5 ng of total RNA. The amount of the brain total RNA was increased, while the amount of liver total RNA was decreased (according to the ratios listed in Table 8).

As shown in Table 8, liver-specific miRNA expression was detected. No signal was detected from a RNA source other than liver (Brain, HeLa), but was detected from liver RNA. Additionally, when the amount of liver RNA was decreased by half, the $C_T$ increased by 1, until the number of relevant molecules was low (less than ~20 molecules). Furthermore, even when as little as 0.03125% of an RNA pool was from liver, miR-122a was detected in a background of 99.96875% irrelevant RNA. Such sensitivity has not been achieved by other known methods.

TABLE 8

Detection of miR-122a in RNA from different sources

| RNA source | Average $C_T$ | STDEV | $\Delta C_T$ |
|---|---|---|---|
| Brain | | | |
| HeLa | | | |
| Liver | | | |
| HeLa 96%, Liver 4% | 32.63 | 0.22 | 0.78 |
| HeLa 98%, Liver 2% | 33.41 | 0.14 | 1.00 |
| HeLa 99%, Liver 1% | 34.41 | 0.35 | 1.38 |
| HeLa 99.5%, Liver 0.5% | 35.79 | 0.60 | 0.83 |
| HeLa 99.75%, Liver 0.25% | 36.62 | 0.82 | 0.98 |
| HeLa 99.875%, Liver 0.125% | 37.60 | 0.72 | 0.87 |
| HeLa 99.9375%, Liver 0.0625% | 38.47 | 0.96 | 1.48 |
| HeLa 99.96875%, Liver 0.03125% | 39.95 | | |
| Brain | ND | ND | |
| Liver | 27.38 | 0.17 | |
| HeLa | ND | ND | |

Example 6

Detection of Synthetic miR 124a in a Diverse RNA Background

The sensitivity of the method described in Examples 1 and 2 was tested by detecting a particular target nucleotide sequence when low concentrations of the target are present within a high background concentration of nucleic acids. Reduced amounts of synthetic miR-124a were added to 0.05 ng of total background RNA from HeLa cells for a final concentration ranging from $2.35 \times 10^{-6}$ fmol to $1.16 \times 10^{-9}$ fmol of miR-124a target nucleotide sequences. Each concentration was performed in 5 replicates. The average $C_T$ and standard deviation were calculated. Table 9 demonstrates that the background RNA from the HeLa cells provided a signal of 47.61 $C_T$. The $C_T$ was increased by ~1 when the amount of synthetic 124a-RNA was decreased by half in the higher concentrations. The minimal amount of synthetic 124a-RNA that gave a signal above the background signal is $1.86 \times 10^{-8}$ fmol.

TABLE 9

Detection of synthetic miR-124a in a diverse RNA background

| RNA: miR-124a | Average | STDEV | $\Delta Ct$ |
|---|---|---|---|
| 2.38E−06 fmol | 35.18 | 0.43 | 1.06 |
| 1.19E−06 fmol | 36.24 | 0.36 | 1.00 |
| 5.95E−07 fmol | 37.24 | 0.75 | 1.59 |
| 2.98E−07 fmol | 38.83 | 1.03 | 3.58 |
| 1.49E−07 fmol | 42.42 | 3.35 | 1.41 |
| 7.44E−08 fmol | 43.82 | 5.04 | −0.11 |
| 3.72E−08 fmol | 43.72 | 4.57 | 2.78 |
| 1.86E−08 fmol | 46.50 | 3.38 | 1.76 |
| 9.30E−09 fmol | 48.26 | 1.41 | 0.07 |
| 4.65E−09 fmol | 48.33 | 2.35 | 1.27 |
| 2.32E−09 fmol | 49.60 | 0.55 | −1.55 |
| 1.16E−09 fmol | 48.05 | 2.69 | |
| HeLa 0.05 ng | 47.61 | 2.93 | |
| Brain 0.05 ng | 25.34 | 0.12 | |
| No cDNA | ND | | |

Example 7

Detection of Different miRNA Target Sequences in Human Serum

The method described in Examples 1 and 2 was then applied to detecting many miRNA target sequences in the human serum. Total RNA was extracted from serum samples of three individuals by using LS buffer (Promega) in combination with the Mirvana kit (Ambion). Volumes of 300 µl of serum were obtained from subject number 5 and 7, and 150 µl of serum was obtained from subject number 6 for RNA purification. A total of 10% of the purified RNA was used for each PCR and hybridization reaction according to the methods described above. Probes specific for the miR target sequences are shown in Table 12 below. Table 10 demonstrates that different microRNAs such as miR-21, hsa-miR-142-3p and Let-7d could specifically be detected in a serum sample. Table 10 indicates that various miRNA target sequences can be extracted, isolated and detected from biological fluids such as human serum.

TABLE 10

Detection of different microRNA target sequences in human serum

| Fwd primer and MGB probe | Sample no. 5 $C_T$ | Sample no. 6 $C_T$ | Sample no. 7 $C_T$ |
|---|---|---|---|
| hsa-miR-21 | 33.03 | 31.28 | 29.55 |
| hsa-miR-142-3p | 35.3 | 39.27 | 37.16 |
| Let-7a | ND | 39.22 | 36.63 |
| Let-7c | ND | ND | ND |
| Let7-d | 33.89 | 34.71 | 34.01 |
| hsa-miR-99a | ND | ND | ND |
| hsa-miR-100 | ND | ND | ND |
| hsa-miR-125a | ND | ND | ND |
| hsa-miR-125b | 36.72 | 36.3 | 39.37 |
| hsa-miR-122a | 38.6 | 35.8 | 35.99 |
| hsa-miR-124a | ND | ND | ND |

Example 8

Detection of Different miRNA Target Sequences in Formalin Fixed, Paraffin-Embedded (FFPE) Tissues RNA was isolated from formalin fixed, paraffin-embedded (FFPE) tissues originated from bladder, prostate and liver with colon metastasis.

1 ml Xylene (Biolab) was added to 1-2 mg tissue, incubated at 57° C. for 5 min and centrifuged for 2 min at 10,000 g. The supernatant was removed, and 1 ml Ethanol (100%) (Biolab) was added. Following centrifugation for 10 min at 10,000 g, the supernatant was discarded and the washing procedure was repeated. Following air drying for 10-15 min, 500 µl Buffer B (NaCl 10 mM, Tris pH 7.6, 500 mM, EDTA 20 mM, SDS 1%) and 5 ul proteinase K (50 mg/ml) (Sigma) were added. Following incubation at 45° C. for 16 h, inactivation of the proteinase K at 100° C. for 7 min was preformed. Following extraction with acid phenol chloroform (1:1) (Sigma) and centrifugation for 10 min at maximum speed at 4° C., the upper phase was transferred to a new tube with the addition of 3 volumes of 100% Ethanol, 0.1 volume of NaOAc (BioLab) and 8 µl glycogen (Ambion) and left over night at −20° C.

Following centrifugation at maximum speed for 40 min at 4° C., washing with 1 ml Ethanol (85%), and drying, the RNA was re-suspended in 45 µl DDW.

The RNA concentration was tested and DNase Turbo (Ambion) was added accordingly (1 µl DNase/10 µg RNA). Following Incubation for 30 min at room temperature and extraction with acid phenol chloroform and precipitation, the RNA was re-suspended in 45 µl DDW. The RNA concentration was tested again and DNase Turbo (Ambion) was added accordingly (1 µl DNase/10 µg RNA). Following incubation for 30 min at room temperature and extraction with acid phenol chloroform and precipitation, the RNA was re-suspended in 20 µl DDW.

A total of 10% of the purified RNA was used for each PCR and hybridization reaction according to the methods described above. Probes specific for the miR target sequences are shown in Table 11 below. Table 13 demonstrates that different microRNAs could specifically be detected in FFPE sample. Table 11 indicates that various microRNA target sequences can be extracted, isolated and detected from FFPE tissues.

TABLE 11

Detection of different microRNA target sequences in (FFPE) tissues

| Fwd primer and MGB probe | $C_T$ Bladder | $C_T$ Bladder | $C_T$ Liver-Colon | $C_T$ Liver-Colon | $C_T$ Bladder | $C_T$ Prostate |
|---|---|---|---|---|---|---|
| Let7d | 35.27 | 35.37 | 38.28 | 38.6 | 37.27 | 35.9 |
| miR-126 | 34.33 | 34.2 | 34.75 | 33.54 | 35.48 | 34.72 |
| miR-24 | 31.22 | 31.12 | 34.35 | 33.24 | 34.34 | 33.03 |
| miR-21 | 33.07 | 31.88 | 31.56 | 30.68 | 29.85 | 31.41 |
| miR-122a | ND | ND | 31.58 | 33.02 | ND | ND |
| miR-494 | ND | ND | ND | ND | ND | ND |
| miR-125a | 36.87 | 37.08 | 37.54 | 36.11 | 38.17 | 37.59 |
| miR-125b | 34.45 | 34.64 | 30.31 | 30.97 | 32.79 | 29.89 |
| miR-145 | 35.03 | 36.19 | 34.13 | 33.2 | 32.68 | 29.81 |
| miR-194 | 39.01 | 40.69 | 33.75 | 33.5 | 42.9 | 44.2 |
| miR-205 | 29.22 | 29.13 | ND | ND | 33.38 | 32.05 |
| miR-124a | ND | ND | ND | ND | | ND |

Example 9

Detection of Different miRNA Target Sequences in Amniotic Fluids 20 ml of Amniotic fluid (non miconial) was collected during caesarean surgery, into 2×15 ml tubes. Cells were recovered by centrifugation at 1000 g for 10 minutes at 4° C. Supernatant was collected and aliquoted to eppendorf tubes at volumes of 400 µl and frozen at −80° C. Cell pellet was re-suspended with PBS and re-centrifuged at the same conditions. Then pellet was re-suspended in 0.5 ml buffer A (taken from EZ-RNA II kit by Biological Industries), transferred to an eppendorf tube and stored at −80° C.

RNA from Amniotic cell fraction was extracted using EZ-RNA II kit (Biological Industries, Israel) according to the manufacturer's protocol.

RNA in the amniotic fluid supernatant is extracted as described below:

100 µl of sample was incubated at 56° C. for 1 h in 0.8 ml of pre-heated extraction solution (NaCl, 0.1M; Tris Hcl pH8, 10 mM; DTT, 40 mM; EDTA pH8, 10 mM; SDS 70 mM; Proteinase K, 0.65 mg/ml). Spikes were added as control.

90 µl of 3M NaOAc and 1 ml of acid phenol:chloroform were added. Incubation at 4° C. until two phases were separated (at least 20 min). Centrifugation was preformed at 16,000 g for 20 min at RT. The aqueous phase (~1 ml) was transferred to a new tube. 8 µl glycogen and 3 vol. ETOH were added and precipitated ON at −20° C. Centrifugation was preformed for 40 min at max speed at 4° C.

The pellet was washed with 85% ETOH, dried at 65° C. and re-suspended in 43 µl DDW. 2 µl Turbo DNase (Ambion) and 5 µl Buffer were added, and incubation was preformed for 1 h at 37° C.

Following extraction with acid phenol:chloroform, the pellet was re-suspend in 20 µl DDW.

RNA isolated from 100 μl of amniotic fluid was used for each PCR and hybridization reaction according to the methods described in Examples 1 and 2.

Table 12 demonstrates that different microRNAs could specifically be detected in amniotic fluid samples obtained from 6 individuals. Table 12 indicates for the first time that various microRNA target sequences can be extracted, isolated and detected from amniotic fluid samples.

TABLE 12

Detection of different microRNA target sequences in amniotic fluids

| $C_T$ 1 | 2 | 3 | 4 | 5 | 6 | miR name |
|---|---|---|---|---|---|---|
| 35.16 | 37.78 | 34.01 | 35.67 | 33.79 | 33.71 | Let7d |
| 34.8 | 44.23 | 35.78 | 38.97 | 38.05 | 36.42 | miR-126 |
| 32.63 | 33.99 | 30.28 | 31.89 | 31.52 | 30.62 | miR-24 |
| 30.52 | 33.01 | 29.64 | 30.15 | 30.2 | 28.97 | miR-21 |
| 31.73 | 34.56 | 32.41 | 32.64 | 31.92 | 31.91 | miR-16 |
| 35.47 | 40.9 | 36.79 | 42.42 | 38.92 | 38.6 | miR-451 |

Example 10

Detection of Different miRNA Target Sequences in Human Urine

The protocol used for miRNA extraction from urine (500 μl) is the same as described in Example 9. Table 13 demonstrates that different microRNAs could specifically be detected in human urine sample. Table 13 indicates for the first time that various microRNA target sequences can be extracted, isolated and detected from human urine.

TABLE 13

Detection of different microRNA target sequences in human urine

| miR name | $C_T$ |
|---|---|
| miR-103 | 39.2798 |
| miR-22 | 37.341 |
| miR-320 | 38.038 |
| miR-192 | 39.793 |
| miR-200c | 39.0157 |
| miR-92 | 36.7871 |
| miR-21 | 34.3883 |
| miR-375 | 38.0334 |
| miR-93 | 39.6563 |
| U6 snRNA | 36.9035 |

Example 11

Detection of Different miRNA Target Sequences in Saliva, Pleural and Breast Secretions The protocol used for miRNA extraction from saliva, pleural and breast secretions is the same as described in Example 9 with minor modifications. To improve the purity of saliva RNA extracted the incubation with proteinase K was extended for 3 h and RNA was precipitated at −80° C. overnight.

Tables 14A-B demonstrate that different microRNAs could specifically be detected in human saliva, pleural and breast secretions. Tables 14A-B indicate for the first time that various microRNA target sequences can be extracted, isolated and detected from human saliva pleural and breast secretions.

TABLE 14a

Detection of different microRNA target sequences in human saliva

| target | cDNA, 5 ng/ul | cDNA 1 ng/ul |
|---|---|---|
| miR-205 | undetected | undetected |
| miR-21 | 31.64 | 33.86 |
| miR-223 | 27.29 | 29.10 |
| miR-491 | 35.16 | 37.22 |
| miR-494 | undetected | undetected |
| U6 | 24.89 | 27.10 |

TABLE 14B

Detection of different microRNA target sequences in human pleural and breast secretions

| | Breast | | | Pleural | | |
|---|---|---|---|---|---|---|
| target | 2.5 | 0.25 | Δ 0.25 – 2.5 | 2.5 | 0.25 | Δ 0.25 – 2.5 |
| let7d | 37.6 | 40.05 | 2.45 | 33 | 36.88 | 3.88 |
| mir-126 | ND | ND | ### | 34.26 | 37.4 | 3.14 |
| hsa-miR-24 | ND | ND | ### | 30.74 | 34.49 | 3.75 |
| mir-21 | 34.22 | 37.47 | 3.25 | 27.18 | 30.82 | 3.64 |
| hsa-miR-16 | 41 | ND | ### | 30.8 | 34.41 | 3.61 |
| hsa-miR-451 | ND | ND | ### | 33 | 37.53 | 4.53 |

Example 12

Using ECLIPSE® Probes for Detecting a Target Nucleic Acid

MGB ECLIPSE® probes carry a minor binder moiety that allows the use of short probes for very high specificity. These are short linear probes that have a minor groove binder and a fluorophore (or quencher) on the 5' end and a quencher (or fluorophore) on the 3' end, which is the opposite orientation of the MGB molecule used in Example 3 (TaqMan MGB probes). The minor groove binder may prevent the exonuclease activity of the Taq polymerase from cleaving the probe.

The ECLIPSE® MGB molecule was used in a quantitative real time PCR reaction according to the same conditions which were used with the previous MGB probes. The sequences of the Oligo dT PCR primers and probes are presented below.

```
                              (SEQ ID NO. 20860)
Probe Let7A21:     CCGTTTTTTTTTTAACTATAC
```

```
                              (SEQ ID NO. 20861)
Probe Let7C21:     CCGTTTTTTTTTTAACCATAC
```

The RT-primer sequence that was used for the ECLIPSE® reaction:

```
                                        (SEQ ID NO. 20862)
RT10:  GCGAGCACAGAATTAATACGACTCACTATCGGTTTTTTTTTTVN
```

Using a Let-7a or Let-7c-specific ECLIPSE® MGB probes with one mismatch to the adaptor sequence enabled the distinction between Let-7a and Let-7c via real time PCR, as shown by the difference in their corresponding $C_T$ (Table 17).

TABLE 15

Detection of the Let-7 family members by ECLIPSE +200 MGB probe

| RNA sample name | Probe &primer Let7A | Probe &primer Let7C |
|---|---|---|
| Let7A RNA | 27.38 | 35.49 |
| Let7C RNA | 31.27 | 30.63 |
| Let7A + C RNA | 26.88 | 31.99 |
| Let7A RNA | 31.4 | 40.04 |
| Let7C RNA | 33.43 | 34.89 |
| Let7A + C RNA | 31.25 | 37.1 |
| Let7A RNA | 35.97 | 43.46 |
| Let7C RNA | 40.15 | 41.41 |
| Let7A + C RNA | 34.09 | 39.8 |

Example 13

Prediction of mRNAs

We surveyed the entire human genome for potential miRNA coding genes using computational approaches similar to those described in U.S. Patent Application Nos. 60/522,459, 10/709,577 and 10/709,572, the contents of which are incorporated herein by reference, for predicting miRNAs. Briefly, non-protein coding regions of the entire human genome were scanned for hairpin structures. The predicted hairpins and potential miRNAs were scored by thermodynamic stability, as well as structural and contextual features. The algorithm was calibrated by using miRNAs in the Sanger Database which had been validated. Table 1 of U.S. patent application Ser. No. 11/429,720, the contents of which are incorporated herein, lists the SEQ ID NO for each predicted hairpin ("HID") from the computational screen. Table 1 of U.S. patent application Ser. No. 11/429,720 also lists the genomic location for each hairpin ("Hairpin Location"). The format for the genomic location is a concatenation of <chr_id><strand><start position>. For example, 19+135460000 refers chromosome 19, +strand, start position 135460000. Chromosomes 23-25 refer to chromosome X, chromosome Y and mitochondrial DNA, respectively. The chromosomal location is based on the hg17 assembly of the human genome by UCSC (genome.ucsc.edu), which is based on NCBI Build 35 version 1 (35.1) and was produced by the International Human Genome, Sequencing Consortium.

Table 1 of U.S. patent application Ser. No. 11/429,720 also lists whether the hairpin is conserved in evolution ("C"). The hairpins were identified as conserved ("Y") or nonconserved ("N") by using phastCons data. The phastCons data is a measure of evolutionary conservation for each nucleotide in the human genome against the genomes of chimp, mouse, rat, dog, chicken, frog, and zebrafish, based on a phylo-HMM using best-in-genome pair wise alignment for each species based on BlastZ, followed by multiZ alignment of the 8 genomes (Siepel et al, J. Comput. Biol 11, 413-428, 2004 and Schwartz et al., Genome Res. 13, 103-107, 2003). A hairpin is listed as conserved if the average phastCons conservation score over the 7 species in any 15 nucleotide sequence within the hairpin stem is at least 0.9 (Berezikov, E. et al. Phylogenetic Shadowing and Computational Identification of Human microRNA Genes. Cell 120, 21-24, 2005). Table 1 of U.S. patent application Ser. No. 11/429,720 also lists the genomic type for each hairpin ("T") as either intergenic ("G"), intron ("I") or exon ("E"). Table 1 of U.S. patent application Ser. No. 11/429,720 also lists the SEQ ID NO ("MID") for each predicted miRNA and miRNA*. Table 1 of U.S. patent application Ser. No. 11/429,720 also lists the prediction score grade for each hairpin ("P") on a scale of 0-1 (1 the hairpin is the most reliable), as described in Hofacker et al., Monatshefte f. Chemie 125: 167-188, 1994. If the grade is zero or null, they are transformed to the lower value of PalGrade that its p-value is <0.05. Table 1 of U.S. patent application Ser. No. 11/429,720 also lists the p-value ("Pval") calculated out of background hairpins for the values of each P scores. As shown in Table 1 of U.S. patent application Ser. No. 11/429,720, there are few instances where the Pval is >0.05. In each of these cases, the hairpins are highly conserved or they have been validated (F=Y). Table 1 of U.S. patent application Ser. No. 11/429,720 also lists whether the miRNAs were validated by expression analysis ("E"); this column was intentionally left blank. Table 1 of U.S. patent application Ser. No. 11/429,720 also lists whether the miRNAs were validated by sequencing ("S") (Y=Yes, N=No). If there was a difference in sequences between the predicted and sequenced miRNAs, the sequenced sequence is predicted. It should be noted that failure to sequence or detect expression of a miRNA does not necessarily mean that a miRNA does not exist. Such undetected miRNAs may be expressed in tissues other than those tested. In addition, such undetected miRNAs may be expressed in the test tissues, but at a difference stage or under different condition than those of the experimental cells. Table 1 of U.S. patent application Ser. No. 11/429,720 also lists whether the miRNAs were shown to be differentially expressed ("D") (Y=Yes, N=No) in at least one disease, as detailed in Table 2 of U.S. patent application Ser. No. 11/429,720, the contents of which are incorporated herein. Table 1 of U.S. patent application Ser. No. 11/429,720 also lists whether the miRNAs were present ("F") (Y=Yes, N=No) in Sanger DB Release 8 (February 2005) (nar.oupjournals.org/) as being detected in humans or mice or predicted in humans. As discussed above, the miRNAs listed in the Sanger database are a component of the prediction algorithm and a control for the output. Table 1 of U.S. patent application Ser. No. 11/429,720 also lists a genetic location cluster ("LC") for those hairpins that are within 5,000 nucleotides of each other. Each miRNA that has the same LC share the same genetic cluster. Table 1 of U.S. patent application Ser. No. 11/429,720 also lists a seed cluster ("SC") to group miRNAs by their seed of 2-7 by an exact match. Each miRNA that has the same SC have the same seed. For a discussion of seed lengths of 5-6 nucleotides being sufficient for miRNA activity, see Lewis et al., Cell, 120; 15-20 (2005).

Example 14

Prediction of Target Genes

The predicted miRNAs from the computational screening of Example 13 were then used to predict target genes and their binding sites using two computational approaches similar to those described in U.S. Patent Application Nos. 60/522,459, 10/709,577 and 10/709,572, the contents of which are incorporated herein by reference, for predicting miRNAs.

Table 4 of U.S. patent application Ser. No. 11/429,720, the contents of which are incorporated herein by reference, lists the predicted target gene for each miRNA (MID) and its hairpin (HID) from the computational screen. The names of the target genes were taken from NCBI Reference Sequence release 16 (http://www.ncbi.nlm.nih.gov; Pruitt et al., Nucleic Acids Res, 33(1):D501-D504, 2005; Pruitt et al., Trends Genet., 16(1):44-47, 2000; and Tatusova et al., Bioinformatics, 15(7-8):536-43, 1999). Target genes were identified by having a perfect complementary match of a 7 nucleotide miRNA seed (positions 2-8) that have an "A" after the seed on the UTR and/or an exact match in the nucleotide before the seed (total=8 nucleotides). For a discussion on identifying target genes, see Lewis et al., Cell, 120: 15-20, (2005). For a discussion of the seed being sufficient for binding of a miRNA to a UTR, see Lim Lau et al., (Nature 2005) and Brenneck et al, (PLOS Biol 2005). Binding sites were then predicted using a filtered target genes dataset by including only those target genes that contained a UTR of a least 30 nucleotides. The binding site screen only considered the longest transcript when there were several transcripts per gene. A total of 16,656 transcripts were included in the dataset. Table 4 of U.S. patent application Ser. No. 11/429,720 lists the SEQ ID NO for the predicted binding sites for each target gene as predicted from each miRNA ("MID"). The sequence of the binding site includes the 20 nucleotides 5' and 3' of the binding site. If the binding site encompasses 2 exons, the sequence includes 20 nucleotides 5' and 3' of the binding site, as the ends are situated on the spliced mRNA. Table 5 of U.S. patent application Ser. No. 11/429,720, the contents of which are incorporated herein, shows the relationship between the miRNAs ("MID")/hairpins ("HID") and diseases by their target genes. The names of diseases are taken from OMIM. For a discussion of the rational for connecting the host gene the hairpin is located upon to disease, see Baskerville and Bartel, RNA, 11: 241-247 (2005) and Rodriguez et al., Genome Res., 14: 1902-1910 (2004). Table 5 of U.S. patent application Ser. No. 11/429,720 shows the number of miRNA target genes ("N") that are related to the disease. Table 5 of U.S. patent application Ser. No. 11/429,720 also shows the total number of genes that are related to the disease ("T"), which is taken from the genes that were predicted to have binding sites for miRNAs. Table 5 of U.S. patent application Ser. No. 11/429, 720 also shows the percentage of N out of T ("P") and the p-value of hypergeometric analysis ("Pval"). Table 8 of U.S. patent application Ser. No. 11/429,720, the contents of which are incorporated herein, shows the disease codes for the diseases described in Table 5 of U.S. patent application Ser. No. 11/429,720 and Tables 9-11 of U.S. patent application Ser. No. 11/429,720, the contents of which are incorporated herein. For a reference of hypergeometric analysis, see Schaum's Outline of Elements of Statistics II: Inferential Statistics. Table 9 of U.S. patent application Ser. No. 11/429, 720 shows the relationship between the target sequences ("Gene Name") and disease ("Disease Code"). Table 10 of U.S. patent application Ser. No. 11/429,720 shows the relationship between the miRNAs ("MID")/hairpins ("HID"), known SNPs and diseases. SNP were identified in the sequence of hairpins. For the miRNAs of these hairpins, all their target genes listed in Table 4 of U.S. patent application Ser. No. 11/429,720 were collected. For these genes, we checked whether they are associates to disease(s) according to OMIM. The numeric code of the relevant diseases for each miRNA according to Table 9 of U.S. patent application Ser. No. 11/429,720 are presented in Table 10 of U.S. patent application Ser. No. 11/429,720. The disease codes are taken from Table 8 of U.S. patent application Ser. No. 11/429,720. If a target gene was not related to a disease in Table 9 of U.S. patent application Ser. No. 11/429,720, SNP data is not presented. Each SNP ("SNP_Id") is identified based on NCBI database dbSNP BUILD 124 based on NCBI Human Genome Build 35.1. The genomic location for each SNP ("SNP_location") is also provided in a formation concatenating "<chr_id>:<start position>". For example, "19:135460569" means chr19+strand, start position 135460569. Although the mutations are referred to as SNPs, a number of the mutations cover a few nucleotides (e.g., small insertions, deletions, micro-satellites, etc.) For a discussion on the connection between a SNP and disease, see Swibertus (Blood 1996) and Frittitta (Diabetes 2001). Table 11 of U.S. patent application Ser. No. 11/429,720 shows the relationship between miRNAs ("MID"), hairpins ("HID"), SNP identification number ("SNP_Id"), SNP location ("SNP_location"), genes and diseases. SNP identification and location are defined as described for Table 10 of U.S. patent application Ser. No. 11/429,720. The SNPs listed are only those that are located in a miRNA target gene known to be associated with a disease in the OMIM database. "Gene" indicates the name of the gene in which the SNP is located.

Example 15

Differential Expression of miRNAs

1. Sequencing

To validate the hairpins ("HID"), a number of miRNAs were evaluated by sequencing methods similar to those described in. U.S. Patent Application Nos. 60/522,459, 10/709,577 and 10/709,572, the contents of which are incorporated herein by reference. Table 3 of U.S. patent application Ser. No. 11/429,720, the contents of which are incorporated herein, shows the hairpins ("HID") that were validated by sequencing a miRNA ("MID") in the indicated tissue ("Tissue"). Numeric codes for the tissues are shown in Table 6 of U.S. patent application Ser. No. 11/429,720, the contents of which are incorporated herein.

2. Differential Expression

To confirm the hairpins and miRNAs predicted in Example 13, we detected expression in various tissues (versus controls) using the high-throughput microarrays similar to those described in U.S. Patent Application Nos. 60/522,459, 10/709,577 and 10/709,572, the contents of which are incorporated herein by reference. Microarray images were analyzed using Feature Extraction Software (Version 7.1.1, Agilent). Differential expression of the miRNAs was then analyzed in various disease tissues using similar methods described above. Table 2 of U.S. patent application Ser. No. 11/429,720 shows the ratio of disease related expression ("R") compared to normal tissues for the indicated diseases. Disease codes for the disease are shown in Table 7 of U.S. patent application Ser. No. 11/429,720. Table 2 of U.S. patent application Ser. No. 11/429,720 also shows the statistical analysis of the normalized signal ("RPval"). The signal of each probe was set as its median intensity. Signal intensities range from background level of 400 to saturating level of 66,000. 2 channels hybridization was performed and Cy3 signals were compared to Cy5 signals, where fluor reversed chip was preformed (normal vs. disease), probe signal was set to be its average signal. Signals were normalized by first performing a logarithmic transformation (log 2), followed by adapting a polynomic graph of the second degree. Following normalization, a t-test for each miRNA and disease was performed. P values were estimated based on the occurrences of such or greater signal ratios over duplicated experiments. miRNAs with a p value <0.05 are shown in Table 2 of U.S. patent application Ser. No. 11/429,720. The total number of samples ("N") used for each analysis is also shown in Table 2 of U.S. patent application Ser. No. 11/429,720. The differential expression analysis in Table 2 of U.S. patent application Ser. No. 11/429,720 indicates that the expression of a number of the miRNAs is significantly altered in disease tissue.

Example 16

Biochip

1. Probe Printing

Dried microRNA nucleic acid probes with the sequences listed in Table 7 (SEQ ID NOs 1-4167), were dissolved in 3× sodium chloride-sodium citrate buffer (SSC)+0.001% sodium dodecyl sulfate (SDS) or 2×SSC+0.0035% SDS to a final nucleic acid concentration of 20 µM or 10 µM. The probes were then spotted (i.e., printed) on Schott Nexterion® Slide E coated microarray slides using a Genomic Solutions® BioRobotics MicroGrid II according the MicroGrid manufacturer's directions. After spotting the probes, the biochips were processed according to the microarray slide manufacturer's directions. Briefly, the biochips were rehydrated in a humidity chamber with 0.5×SSC at 42° C., immediately dried for 3 sec on a 130° C. heating block, submerged in blocking buffer (1M Tris pH9, 50 mM ethanolamine, 0.1% SDS), and incubated for 20 min at 50° C. with frequent mixing. The biochips were then rinsed twice for 1 min in nuclease-free water. Finally the biochips were dried via centrifugation.

2. Preparing the Biological Sample

Total RNA from fresh tissues, cell lines, formalin-fixed paraffin-embedded RNA, and fractionated RNA enriched for small RNA molecules (after using a column/gel that separates the RNA according to size) was labeled with a fluorescent dye that enabled detection of RNAs hybridized to the biochip. RNA was labeled with a single fluorophore per molecule, and labeling was uniform across different small RNA molecules. The fluorophore was enzymatically attached by RNA ligase to the 3' end of the microRNAs in the sample. The following reagents were then mixed: RNA up to 3.5 µL, Spikes 1 µL, 10× ligation buffer (NEB) 1 µL, or RNA ligase buffer (Amersham) p-CU-Cy3/Cy5* 1 µL, DMSO 1.5 µL, RNAsine 1 µL, T4 RNA ligase (NEB) 1 µL, or RNA ligase (Amersham), DDW up to the final total volume (10 µL). *5'phosphate-rCrU-3-Cy3; 5'phosphate-rCr-U-3-Cy5 (r=ribonucleic acid nucleotide) The above mixture was incubated on a heating block for 1 hr at 4° C. followed by 1 hr at 37° C., or at 0° C. for 2-16 hr, or at 16° C. for 2-16 hr (for low RNA amount).

3. Hybridizing the Biochip

Briefly, labeled RNA was hybridized to the biochip as follows. 3×miRNA Hybridization Buffer from Ambion® was preheated to 70° C. for at least 5 min. A clean coverslip was placed over a printed biochip. The hybridization buffer was mixed with labeled RNAs (RNA-Cy3 labeled and RNA-Cy5 labeled) to achieve a final concentration of 1× buffer and this mixture (30 ul) was then placed on the biochip to cover the probes. Alternatively, a final concentration of 1× buffer and this mixture (110 ul) was placed on Agilent gasket slide with Agilent chamber base. The biochip was heated to 95° C. for 3 min, and then cooled to room temperature by centrifugation for 1 min at room temperature at maximum speed. Finally, the biochip was allowed to hybridize to the labeled RNA mixture for 12-16 hr at 42° C. or 48 hr (for low RNA amount) on water bath or Agilent oven. After hybridization, the biochip was washed for approximately 30 sec at room temperature, with Buffer A (1×SSC, 0.2% SDS), washed twice for 30 sec at room temperature with Buffer B (0.1×SSC), and then dried by centrifugation.

4. Scanning and Analyzing the Biochip

The biochip was scanned using an Agilent Microarray Scanner Bundle G2565BA, which enabled resolution of 10 µm or 5 µm at 100% power or 100% followed by 10%. The data were analyzed using SpotReader or Feature extraction software.

Example 17

High-Throughput Coupling of DNA Probes to LUMINEX® Microspheres

5. Preparing the Coupled LUMINEX® Beads

Carboxylated LUMINEX® microspheres (LUMINEX® xMap technology; Cat# L100-C (101-200)-01), or beads, are coupled to DNA probes that are amino-modified using EDC (1-ethyl-3-(3-dimethylaminopropyl) carbodiimide-HCl; Pierce. Product#77149). DNA probes, which are reverse complements of the target miRNAs, from the mirVana miRNA probe set (Ambion; Cat#1564) are used. The probes are 42-46 nucleotides (nt) long, of which 18-24 nt target a specific miRNA.

Coupling reactions are performed in 1.5 ml tubes and washed using a 96-well filter plate that is resistant to detergents (Multiscreen Solvinert; Millipore; Cat# MSRLN0410). A "coupling table," which specifies how each DNA probe should be coupled to one type of bead that has a unique spectral signature, is prepared. Each probe in a coupled bead mixture can thus be uniquely identified by its signature. Probes are resuspended in DDW to a final concentration of 0.1 mM.

Beads are resuspended by vortexing and sonicating for 20 seconds. 200 µl ($2.5 \times 10^6$ beads) is taken for each reaction. The beads are centrifuged for 2 minutes at maximum speed. The supernatant is removed and the beads are resuspended in 25 µl MES buffer (0.1M, pH 4.5), and vortexed and sonicated again.

1 µl of probe solution is added to the beads and the suspension is mixed by vortexing. 1.5 µl of freshly suspended EDC (10 mg/ml in DDW, pre-warmed to room temperature) is added to each reaction mix and the mixture is vortexed. The reaction is then incubated at room temperature in the dark for 30 minutes. 1.5 µl of fresh EDC is added again and vortexed, followed by another 30 minute incubation. Solvinert filter plates are pre-wetted with 100 µl water. The coupled reaction is then transferred from the tubes to the filter plate and a vacuum applied. 150 µl of 0.02% Tween-20 is added to coupling reaction and vacuumed twice. Two subsequent washes with 150 µl of 0.1% SDS are then performed. The coupled beads are resuspended in 50 µl of TE and thoroughly mixed. Finally, the coupled bead mixtures are transferred to 1.5 ml tubes and kept at 4° C.

Coupled bead mixtures are mixed in equal volumes into sets of 100 in which each of 100 probes is coupled with a different bead type with a unique spectral signature (i.e., 100 different types of beads). Coupled bead mixture sets are checked for the proportion of each couple via LUMINEX®. The mix is diluted in 1.5×TMAC hybridization buffer to final concentration of 1500 beads per reaction (33 µl) from each couple.

6. RNA Extraction and Quality Control

RNA is isolated from paraffin embedded or frozen tissue or from body fluids (e.g. blood, urine, sputum etc.). The extraction process is optimized to insure recovery of the short length RNAs as well. At the final stage RNA is diluted in RNase-free sterile distilled deionized water (DDW).

RNA quality is estimated by measuring the RNA concentration in a Nanoprop spectrophotometer (Nanoprop Technologies ND-1000). Residual salts and organic solvents, and residual proteins are evaluated by measuring 260/230 and 260/280 nm wavelength ratios, respectively. Further quality evaluation and degradation is done by agarose (1.2%) and urea-denaturized acrylamide (13%) gels.

7. Small RNA Fraction Enrichment

5 μg of RNA is diluted in 50-150 μl DDW. The RNA is applied onto YM100 column. The column is centrifuged for 25 minutes at 14,000×G, 4° C. (Microcon YM100 filter device; Millipore; Amicon; Cat #42413). The flow-through is then precipitated with 8 μl (50 mg/ml) Glycogen, 10% volume of 3M NaOAc pH 5.2 and 3-4 volumes of 100% cold EtOH, for 1 hr at 80° C. Next, the tubes are centrifuged for 40 minutes at maximal speed, 4° C. The supernatant is discarded and the pellet is washed with 85% cold EtOH. The pellet is dried and re-suspended in DDW. Between 5 and 10% recovery is expected.

8. Chemical Labeling of miRNA Using ULS Technology

Enriched small RNA isolated from 5 μg of total RNA are biotinylated using a MicroMax labeling and detection kit (Perkin-Elmer; Cat# MP5545). "Naked" spikes (control RNA molecules with non-human sequences, 22 nt long) are added as controls for the labeling procedure (5-20 fmol per reaction). 0.5 μl of ASAP biotin reagent and 2.5 μl of ASAP labeling buffer are added. DDW is added to a final volume of 10 μl.

Reactions are well-mixed and incubated in a thermal controller (PCR machine) for 30 minutes at 85° C. and then cooled to 4° C. for 5 minutes. KREApure reaction clean-up columns are pre-warmed to room temperature for 20 minutes. Columns are pre-spun for 1 minute at maximal speed in 2 ml microtubes and placed into fresh 1.5 ml tubes. The labeling reaction is then applied to the top of the column and spun again for 1 minute at maximal speed. Flow-through is collected and may be used for hybridization or stored at −20° C.

9. RNA Hybridization

Each hybridization reaction contains: MicroMax-labeled miRNAs; 1-5 fmol of pre-biotinylated spikes (control RNA molecules with non-human sequence, 22 nt long with a 5' biotin) as hybridization controls; and a mix of LUMINEX® microspheres coupled to miRNA probe nucleic acids (i.e., a mix of coupled beads).

RNA is first diluted with TE (Tris-EDTA buffer pH 8.0; Sigma T-9285) to a final volume of 17 μl. Then a mix of coupled beads is re-suspended by vortexing and sonicating for 20 seconds. 33 μl of mix is added to RNA using 1500 coupled beads per reaction. A tube containing buffer and coupled beads alone (i.e., no RNA) is used as background. Reactions are then mixed and denatured for 5 minutes at 85° C. and subsequently hybridized overnight at 50° C. Hybridization temperatures may be increased up to 55° C. to increase specificity, but it may lower the overall signal.

10. Measurement Via LUMINEX®

Hybridization reactions are transferred to a multiscreen 96-well filter plate (Millipore; Cat# MABVN1210). Vacuum is applied and 75 μl of 20 μg/ml streptavidin-R-phycoerythrin (PhycoLink; Prozyme; Cat# PJ315) diluted in X1 TMAC Hybridization Buffer is added to each well. The suspension is mixed thoroughly and transferred to a 96-well plate (Thermowell 96-well plate, Polycarbonate; Costar 6511).

The plate is placed in a LUMINEX® xMAP reader preheated to 50° C. for 10 minutes and then analyzed by the machine. A dual laser detects bead identity and the quantity of bound material. The LUMINEX® is set to the following specifications: Sample volume: 50 μl; Sample timeout: 100 seconds; Double discrimination gate: 7,500-20,000.

Example 18

High-Throughput Coupling of LNA Probes to LUMINEX® Microspheres

Experiments are performed as in sections 1-6 of Example 17 above, but instead of using the mirVana miRNA probe set, an Exiqon LNA miRNA probe set is used. When LNA probes are used, hybridization to coupled bead mixtures is done at a temperature between 65° C. and 75° C.

Example 19

Sensitivity of DNA Coupled-Bead Probes

To evaluate the sensitivity of detection, "naked" spikes (control RNA molecules with non-human sequences, 22 nt long) at increasing concentrations were added to miRNA biotin labeling reactions performed as described above in Example 17 (Section 4).

Example 20

Sensitivity

Figure 6:
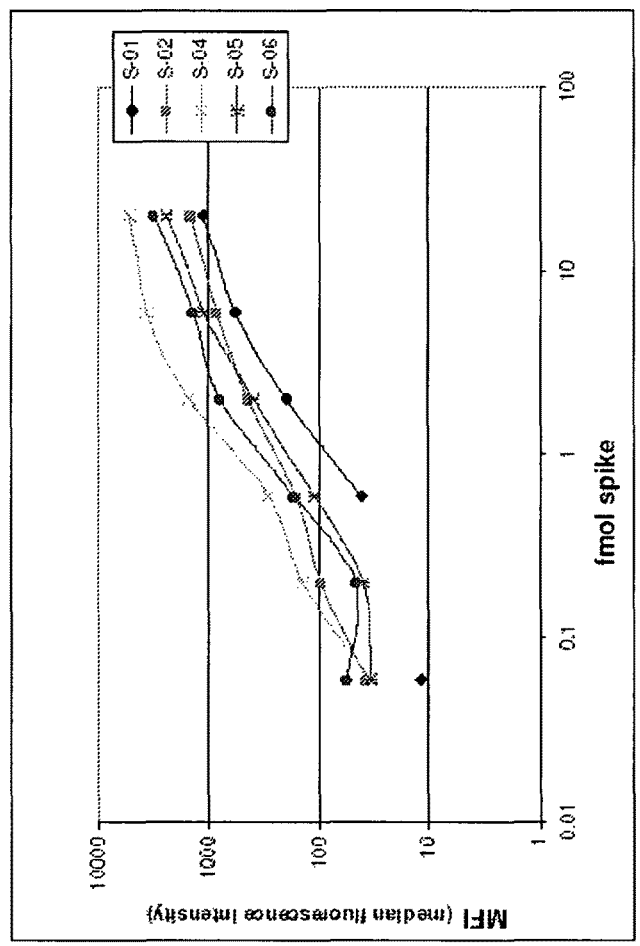
FIG. 6 demonstrates the sensitivity of the LUMINEX® assay as was measured using 5 different Spikes at increasing concentration. Labeling was done using the ULS technology and Ambion probe set was used for bead coupling. The system was found to be sensitive up to 0.06 fmol miRNA and is linear at 2 orders of magnitude. Results are presented on a logarithmic scale.

Spikes at increasing concentration were added to miRNA labeling reaction. An Ambion probe set was used in this experiment. The system was sensitive up to 0.06 fmol miRNA and was linear at 2 orders of magnitude. Results are presented on a logarithmic scale. See FIG. 6.

Figure 7:
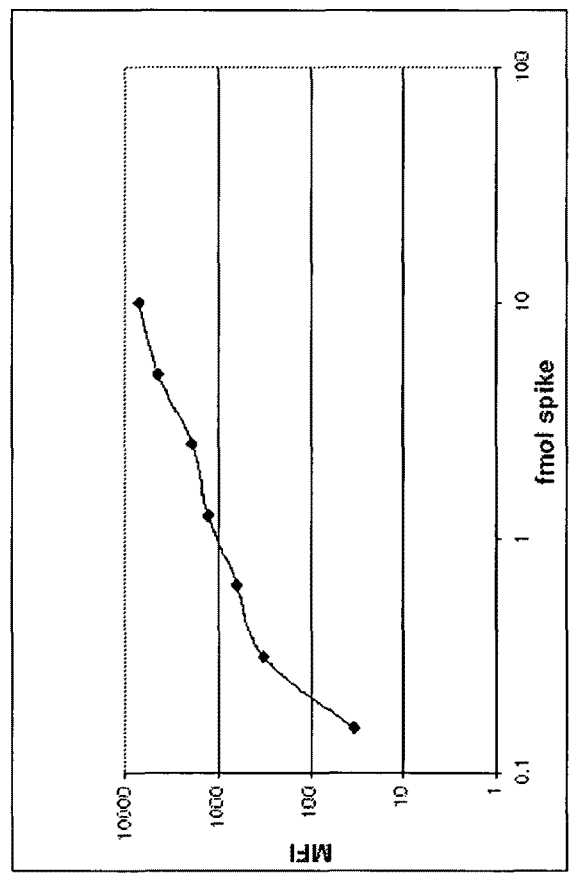
FIG. 7 demonstrates the sensitivity of the assay as was measured using a biotinilated spike at different concentration. Exiqon LNA probe set was used for bead coupling. The system was found to be sensitive up to 0.1 fmol miRNA and is linear in all the examined range, up to 10 fmol. Results are presented on a logarithmic scale.

Biotinylated spike at different concentration was added to miRNA hybridization reaction. Exiqon LNA probe set was used in this experiment. The system was sensitive up to 0.1 fmol miRNA and was linear in all the examined range, up to 10 fmol. Results are presented on a logarithmic scale. See FIG. 7.

Example 21

Specificity

Figure 8:
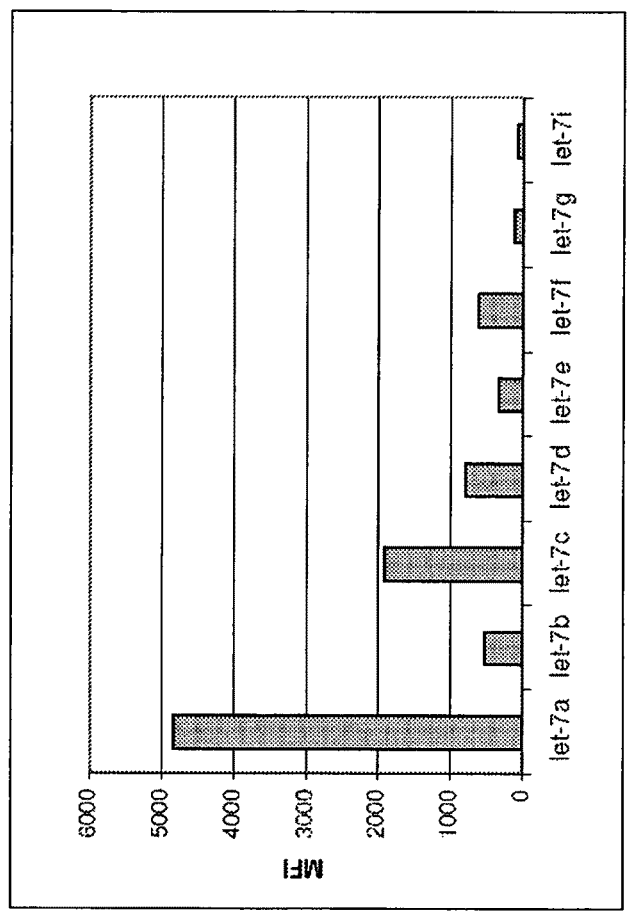
FIG. 8 demonstrates the specificity as was tested using let-7a synthetic miRNA, which was labeled and hybridized with a mixture of bead coupled to different Let-7 family members. The specificity of the system is proportional and correlative to the similarity between the sequences, the number of mismatches, their position in the sequence and the nature of the mismatch (which nt is changed).

Let-7a synthetic miRNA was labeled and hybridized with mix of bead coupled to different Let-7 family members. The specificity of the system was proportional and correlative to the similarity between the sequences, the number of mismatches, their position in the sequence and the nature of the mismatch (i.e., which specific nt was changed). See FIG. 8.

Figure 9:
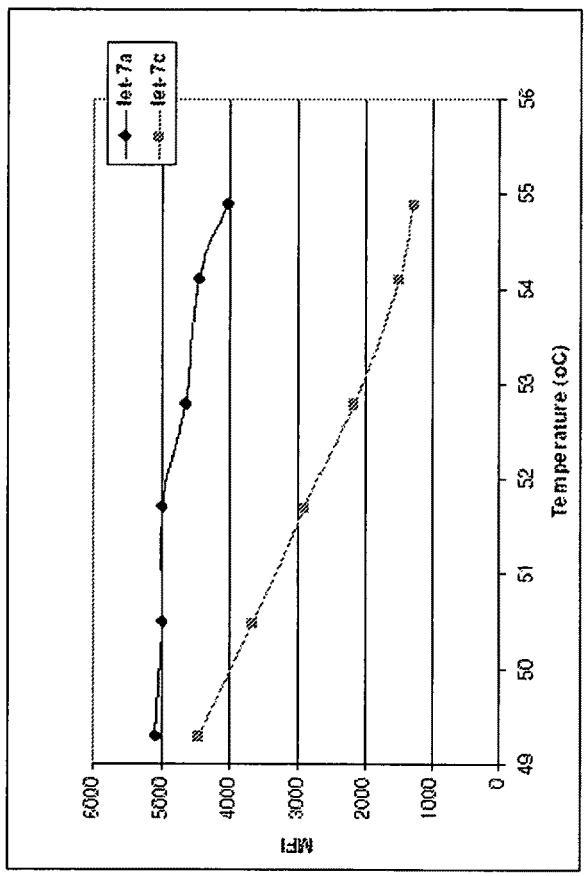
FIG. 9 shows the same specificity test as in FIG. 8 as was performed with increasing hybridization temperatures. Non specific let-7c binding is decreased dramatically with the increase in hybridization temperature, while the specific signal is just slightly affected.

The same experiment was performed with increasing hybridization temperatures. As may be seen in FIG. 9, as hybridization temperature increased, nonspecific let-7c binding decreased dramatically, while the specific signal was just slightly affected.

Example 22

Reproducibility

Figure 10:
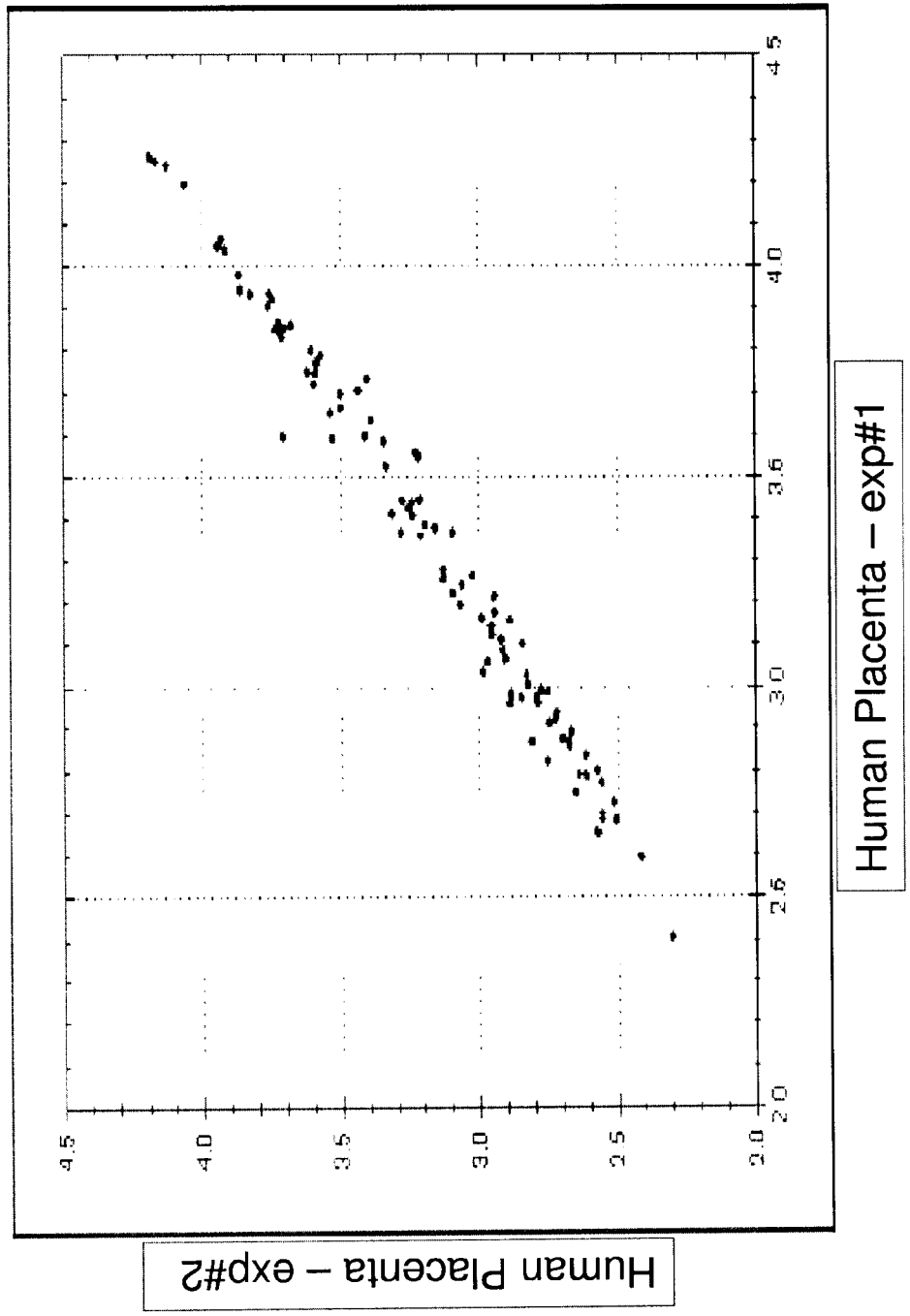
FIG. 10 demonstrates the reproducibility of the labeling and the hybridization. Human placenta RNA was labeled and hybridized in two separate experiments.

Human Placenta was labeled and hybridized as described in Examples 17-19. Reproducibility of two separate experiments is presented in FIG. 10.

Example 23

Tissue Specific miRNA Identification

Brain and placenta RNA from fresh tissue were labeled and hybridized to couple mix. The expression profile of 100 miRNA set is presented FIGS. 11 and 12. miRNAs specific to brain or placenta, as previously described in the literature, were detected and are denoted on the figure. Results are presented on logarithmic scale.

Figure 11:
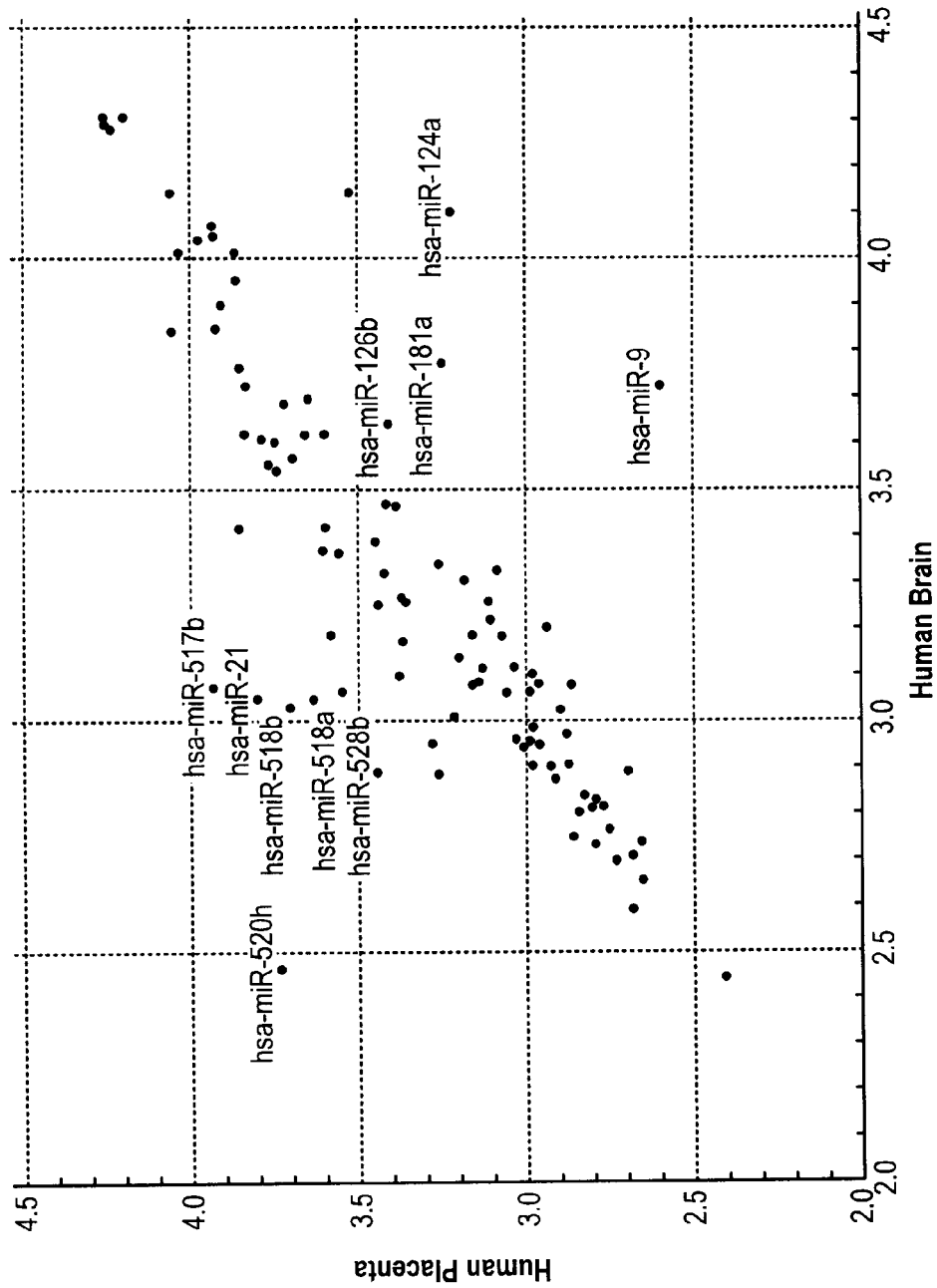
FIG. 11 demonstrates the expression profile of 100 miRNA set. Human brain and placenta RNA from fresh tissue were labeled and hybridized to couple beads having LNA modified probes. miRNAs specific to brain or placenta were detect and are denoted on the figure. Results are presented on logarithmic scale.

FIG. 11 represents binding to LNA modified probes.

Figure 12:
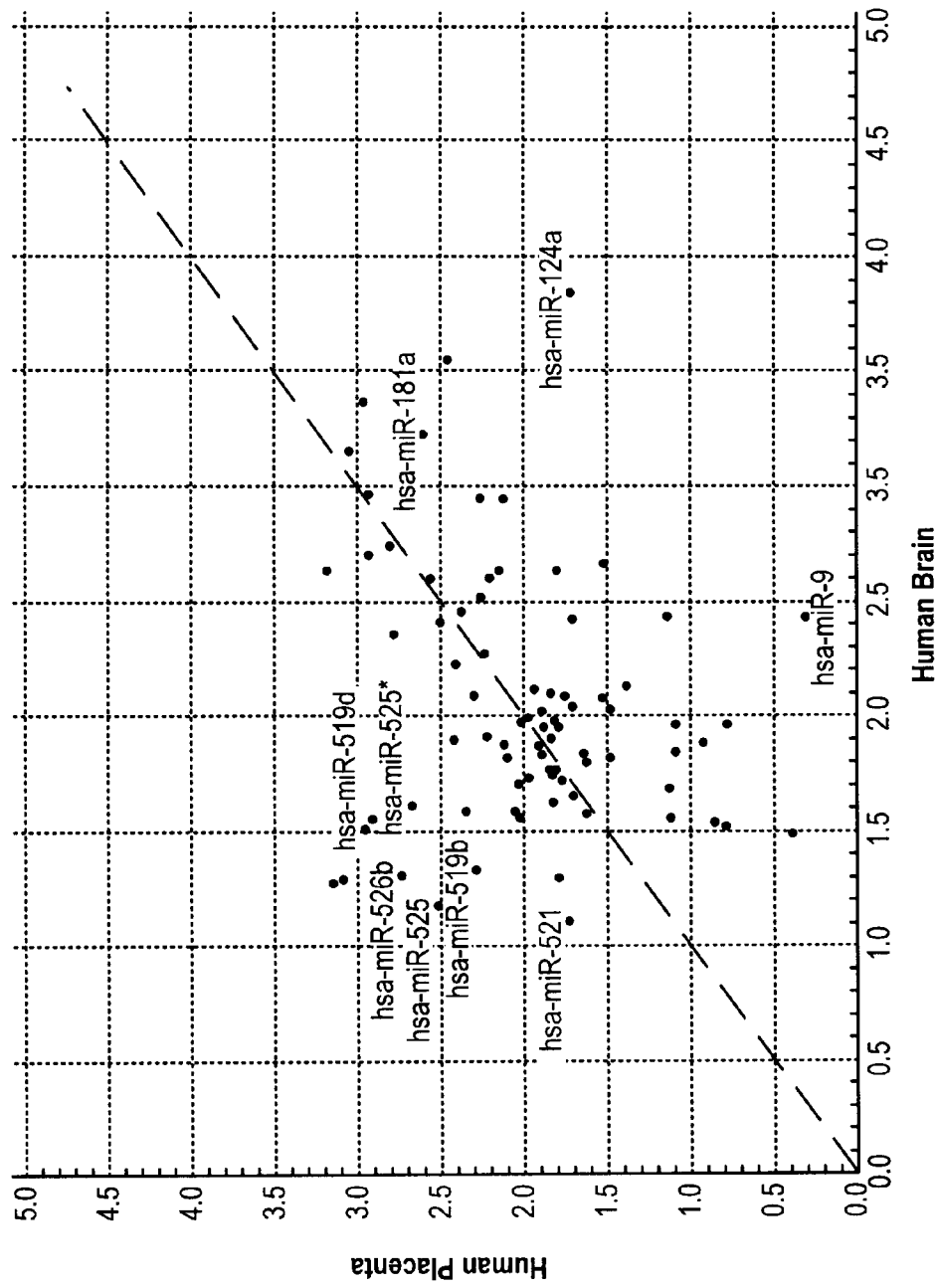
FIG. 12 demonstrates the expression profile of 100 miRNA set. Human brain and placenta RNA from fresh tissue were labeled and hybridized to couple beads having non-modified probes from the Ambion probe set. miRNAs specific to brain or placenta were detect and are denoted on the figure. Results are presented on logarithmic scale.

FIG. 12 represents the binding to non-modified DNA probes from the Ambion probe set.

Example 24

Cancer Tissue miRNA Expression Profiling

Figure 13A:
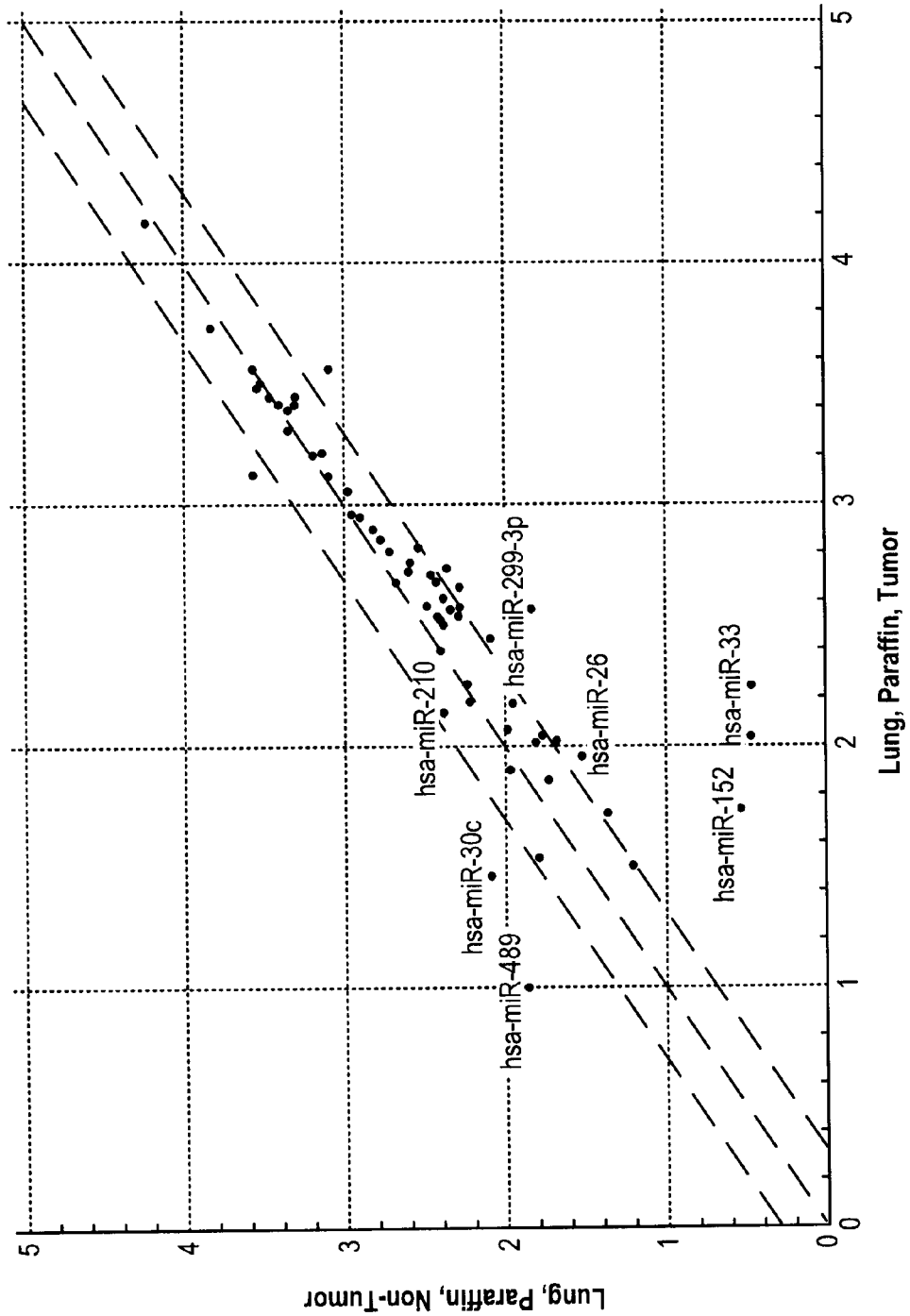
FIGS. 13A-13B demonstrate miRNAs differential expression. The RNA was extracted from formalin fixed paraffin embedded lung (FIG. 13A) and bladder (FIG. 13B) normal and tumor tissues. miRNA expression profile was performed as described. Some miRNAs with differential expression are marked on the graph. Results are presented on logarithmic scale.
Figure 13B:
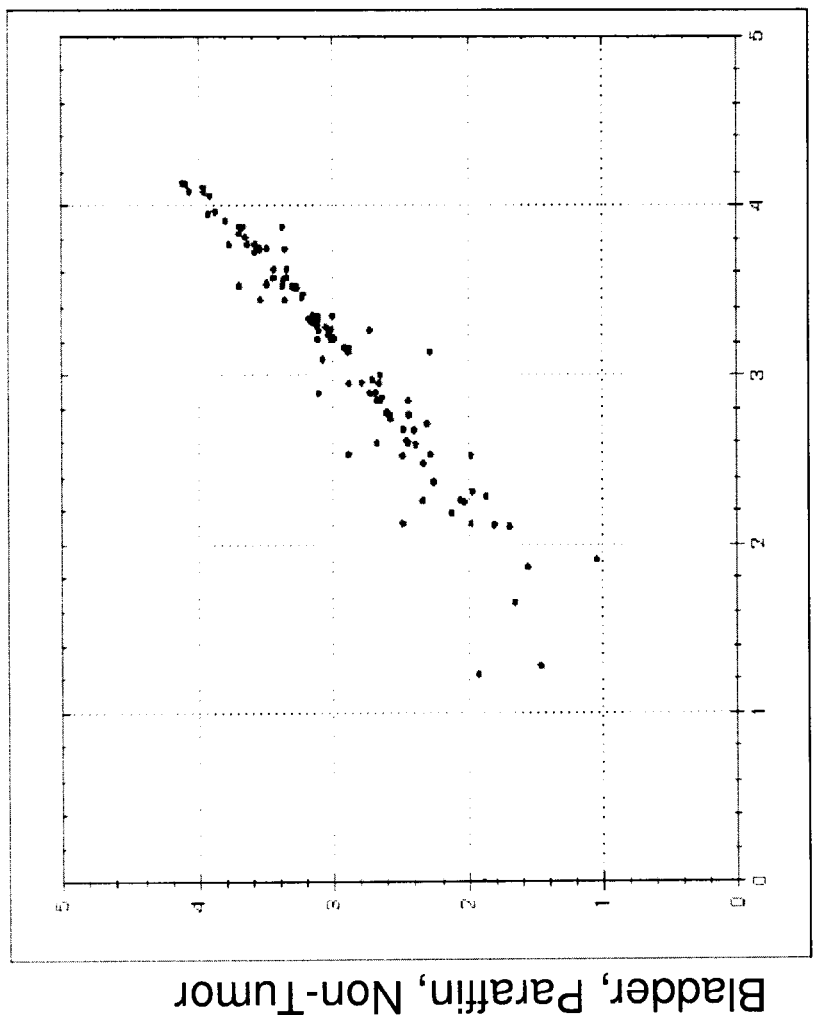

RNA was extracted from formalin fixed paraffin embedded lung and bladder tissues, normal and tumor. miRNA expression profile was performed as described. miRNAs with differential expression are marked on FIGS. 13a-b. The results are presented on logarithmic scale.

Example 25

Detailed Protocols of Other Labeling Methods

1. Direct Labeling
   a. Kreatech Chemical Labeling

The labeling may be performed by ULS Small RNA labeling Kit by Kreatech.

The labeling procedure is similar to what is described above (for PerkinElmer).

An optimal ratio of 1 μl reagent per 50 ng small RNA should be maintained. Preferably, at least 12.5 μg of small RNA should be used in a reaction volume of 10 μl. 1 μl of X10 buffer is added.

b. p-CU-Bio Libations

Enzymatic end labeling of dinucleotide with a biotin entity. Different ligation systems may be used.

(1) Protocol 1: NEB Ligase

| | |
|---|---|
| RNA | 5 μl |
| 3 × Ligation Buffer | 3 μl |
| p-CU-BIO | 1.5 μl |
| DTT 0.1M | 1.5 μl |
| ATP 30 mM | 0.5 μl |
| T4 RNA Ligase (NEB) | 1.5 μl |
| DDW | 2 μl |
| Total Volume | 15 μl |

Incubation for 2 hr at 30° C., following by inactivation for 3 min at 80° C. and O.N. precipitation: Increase volume to 150 μl, add 8 μl glycogen, 15 μl NaOAc, 550 μl 100% EtOH.

Resuspend in 5 μl DDW. Before LUMINEX® add 12 μl TE (final volume 17 μl).

Example 26

Signal Amplification Methods

1. Protocol for TSA (Tyramide Signal Amplification)
   Before Starting:
   1. Re-suspend bioinyl-Tyramide in 0.3 ml DMSO—stock solution (stable at 4° C. for six months).
   2. Dilute stock solution 1:50 using X1 amplification buffer (working solution).
   3. Prepare TNT wash buffer: 0.1M Tris-HCl (pH 7.5), 0.15M NaCl, 0.05% Tween-20.
   4. Prepare TNB blocking buffer: 0.1M Tris-HCl (pH=7.5), 0.15M NaCl, 0.5% blocking reagent.
      Stir and heat (not exceeding 60° C.) for complete dissolution.
      Filter solution, aliquot and store at 4° C.

Procedure:
1. Microspheres coupling, miRNA chemical labeling and hybridization are performed as described above.
2. Wash hybridization reaction by spinning down the sample
3. Resuspend in 100 ul blocking buffer TNB
4. Incubate 30 minutes at RT
5. Spin
6. Resuspend with 100 ul SA-HRP, diluted 1:100 in TNB.
7. Incubate 30 minutes at RT.
8. Load onto Millipore filter plates.
9. Wash ×3 with TNT buffer (apply vacuum and resuspend X3)
10. Add 100 μl of biotinyl-Tyramide working solution (dilute stock solution 1:50 using X1 amplification buffer-working solution).
11. Mix by pipetting up and down.
12. Incubate for 10 minutes at RT
13. Wash with TNT ×3 (as in 10).
14. Add SA-PE 75 ul of 20 ug/ml in TMAC.
15. Incubate 10 minutes at 50° C.
16. Read in LUMINEX®.

Figure 14:
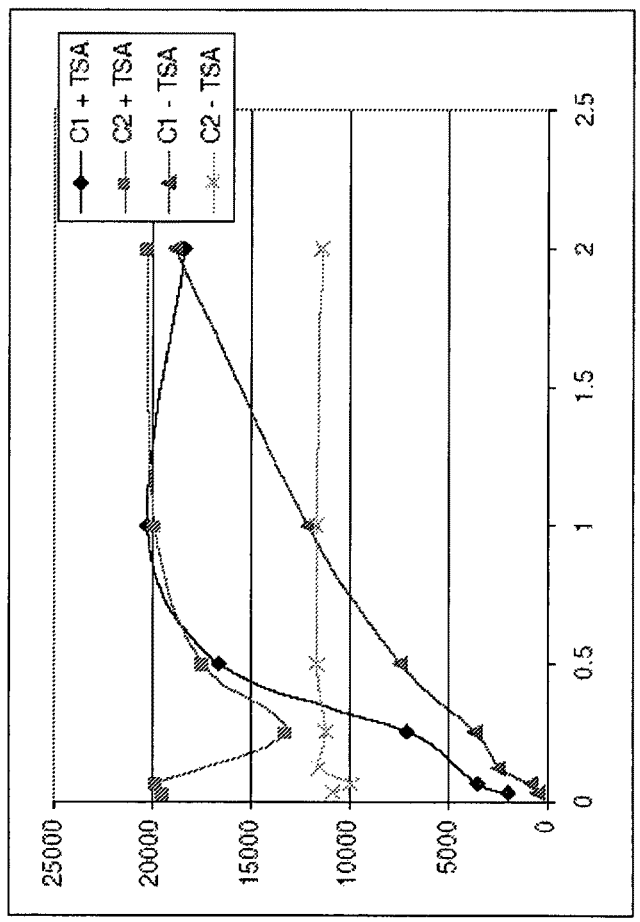
FIG. 14 demonstrates the Tyramide signal amplification (TSA) reaction as was performed onto 2 biotinilated spikes, one of which with increasing concentration (C1) and the other at a constant concentration (C2). The results of both signal; with and without TSA are presented.

FIG. 14 shows how the TSA reaction amplifies of biotinylated spikes

2. Signal Amplification by Genisphere

Protocol for the use of Genisphere signal amplification kit onto the LUMINEX® platform. (Protocol as provided by Genisphere)

1. Enrich miRNA fraction by placing total RNA onto YM-100 column.
   a. Poly (A) Tailing of microRNA:
2. 
   a. Add naked spikes to enriched fraction of miRNA.
   b. Adjust the volume of enriched microRNA and spikes to 15.5 μl with Nuclease Free Water (Vial 10). Depending on the array quality, 50 ng to 500 ng of enriched microRNA will be required to produce quality data.
   c. Dilute the ATP (Vial 4) in 1 mM Tris pH 8.0 according to the following formula:

$$\text{ATP dilution factor} = \frac{5000}{ng \text{ of micro } RNA}$$

3. Add the following components to the 15.5 μl microRNA, for a volume of 25 μl:
   a. 5 μl 5×miRNA Reaction Buffer (Vial 2)
   b. 2.5 μl MnCl2 (Vial 3)
   c. 1 μl diluted ATP (Vial 4 dilution from step 2)
   d. 1 μl PAP Enzyme (Vial 5)
4. Mix gently and microfuge.
5. Incubate in a 37° C. heat block for 15 minutes.
   b. Ligation of "cplCap03" Capture Sequence to the Tailed microRNA
6. Briefly microfuge the 25 μl of tailed microRNA.
7. Add the following components at room temperature for a volume of 36 μl:
   a. 6 μl 6×"cplCap03" Ligation Mix (Vial 9)
   b. 2 μl T4 DNA Ligase (Vial 8)
   c. 3 μl Nuclease Free Water (Vial 10)
8. Mix gently and microfuge.
9. Incubate at room temperature (20-28° C.) for 30 minutes.
10. Stop the reaction by adding 4 μl of 0.5M EDTA pH 8. Briefly vortex and microfuge.

11. Add 60 μl of 1×TE Buffer for a final volume of 100 μl. Briefly vortex and microfuge. This is the Tagged microRNA.
   c. Purification of Tagged microRNA
12. Purify the 100 μl of Tagged microRNA using the MinElute PCR Purification Kit (Qiagen cat. no. 28006) as follows:
   a. Add 500 μl Buffer PB to the 100 μl sample and vortex. Briefly microfuge.
   b. Apply the mixture to the MinElute column and centrifuge for 1 minute at 10-14,000×g (~13,000 rpm) in a conventional tabletop microcentrifuge
   c. Discard the flow-through. Place the MinElute column into the same collection tube
   d. Add 750 μl Buffer PE to the MinElute column and centrifuge for 1 minute.
   e. Discard the flow-through. Place the MinElute column back into the same collection tube
   f. Centrifuge for 2 minutes to remove residual PE buffer
   g. Place the MinElute column into a clean, labeled, 1.5 mL microfuge tube
   h. Add 10 μl Buffer EB to the center of the column membrane. Incubate at room temperature for 2 minutes. Centrifuge for 2 minutes. Discard column and save the 10 μl eluate. This is the Tagged microRNA.
   d. LUMINEX® Bead Binding and Detection Assay Using Tagged LMW RNA
1. Select the appropriate coupled LUMINEX® bead sets (mix).
2. Vortex the coupled beads by vortexing for 10-20 secs.
3. Prepare a working LUMINEX® bead mixture by diluting the coupled LUMINEX® bead stocks to 1500 LUMINEX® beads (per each bead type) per run in 1.5×TMAC (4.5M TMAC) with or without formamide. (Note: 33 uL total of working LUMINEX® bead mixture is required for each reaction.) 10-30% Formamide may be added to the TMAC solution to increase the stringency of the hybridization. Vortex the beads in the TMAC buffer.
4. Add 33 μL of the LUMINEX® bead mixture (from step 3 above) to a nuclease free 0.2 ml strip PCR tube with cap (ISC Bioexpress Cat # T-3034-1).
5. To each tube add 17 uL of tagged LMW RNA's (from the protocol above) diluted in 1×TE pH 8.0 including the appropriate bio-spikes. Add the equivalent of 20-150 ng of LMW RNA (as measured prior to tagging procedure). Incubate for 16 hours at 50° C. (65° C. if probes are LNA) with shaking at 300 RPM.
6. Transfer the entire reaction from each tube to the wells of a pre-wetted (with 1×PBS) Multiscreen-BV filter plate (Millipore cat# MABVN1210).
7. Wash the beads (in the filter plate) once with 1×TMAC (pre-warmed to 50° C.) using a vacuum manifold.
8. Add 50 μL of biotinylated Cap03 dendrimer diluted to 1.0 ng/uL in Genisphere's Binding Buffer 1. Incubate at 37° C. for 2 hours with shaking at 300 RPM.
9. Wash the beads once with 1×TMAC pre-warmed to 50° C.
10. Add 50 uL of SA-PE (ProZyme) diluted to 20 ng/uL in 1×PBS. Incubate for 30 minutes at 37° C. with shaking at 300 RPM.
11. Wash the beads 1× with 1×PBS.
12. Add 75 μL of 1×PBS to each well and transfer the contents of the well to a separate microtiter plate.
13. Analyze on the LUMINEX® 100 calibrated at the low RPI calibration.

Optional:
Anti-PE Biotin (Dendrimer) Reagent
We used this dendrimer reagent for further improving the sensitivity of the miRNA LUMINEX® assays, which has resulted in the successful use of as little as 1-3 ng of LMW RNA (equivalent to 50-150 ng total RNA) per multiplex bead assay (6-12 plexes) in our hands. The additional steps for the use of the anti-PE dendrimer reagents are rather simple, and are added to the end of the current miRNA LUMINEX® protocol (following Step II of the current protocol):

Step 12. Dilute the anti-PE biotin dendrimer in Binding Buffer I by adding 5.5 uL of the anti-PE biotin (dendrimer) reagent to 49.5 uL of Binding Buffer I for every bead reaction (microtiter well) desired.

Add 50 uL of the diluted anti-PE biotin dendrimer to each bead reaction in the filter microtiter plate, and incubate at RT for 60 minutes with shaking at 300 RPM.

Step 13. Wash the beads 1× with 1×PBS.
Step 14. Dilute the 50×SA-PE with 1×PBS. Add 50 uL of diluted SA-PE per well, vortex the plate for 5 seconds. Incubate for 30 minutes at 37° C. with shaking at 300 RPM.
Step 15. Wash the beads 1× with 1×PBS.
Step 16. Add 150 uL of 1×PBS to each well. Pipet the beads up and down to mix 5-6 times, then transfer the contents of the well to a separate microtiter plate.
Step 17. Analyze on the LUMINEX® instrument.

Example 27

Transcription Methods

1. Direct Transcript
If this possibility is to be used a sense probe set of the miRNA should be coupled to the microspheres.
Direct transcript labeling method includes the ligation of a RNA; DNA hybride adaptor and the transcription using biotinilated nucleotides.
   1. Prepare the following reaction mixture:

|  | Volume | From stock | Comments |
|---|---|---|---|
| RNA | 5 μl | 1 ug/ul | RNA is after YM-100 |
| Spike 1 - S-01-RNA-S | 2 μl |  | 100 fmol |
| Spike 2 - S-02-RNA-S | mix of both |  | 25 fmol (or create a mix with appropriate fmol of both spikes in 2 ul). |
| 10 × Ligation Buffer | 2.5 μl |  | From NEB |
| Adaptor | 2 μl | 100 p/ul | Box-3-8 19578175 3ada-DT-avrII |
| DMSO | 3.7 μl |  |  |
| RNasine (HPR-1) | 1 μl | 40 U/ul |  |
| T4 RNA Ligase | 1.5 μl |  | Amersham |
| DDW | 8.3 μl |  |  |
| Total Vol | 25 μl |  |  |

2. Incubate at 40 min at 37° C.
   3. Stop reaction by addition of 0.5-2 volumes (12.5 ul) of loading mix (SB Urea) and than run on two phase Acrylamide Urea gel (i.e. 6% top, 13% bottom).
   4. Run on 200 volt 80 mA ~55 min. Cut the slice out of the gel according to RNA markers, between the free adaptor and small RNA.
   5. Elute the RNA by midi GeBAflex-into 0.8 ml DDW (cut off 3500) 120 volt 40 min, and than reverse the polarity of the electric current for 120 seconds.

6. Precipitate the RNA by adding 8 μl glycogen (5 mg/ml) to 400 μl RNA, 1/10 volume NaoAc and 3-4 volume cold ethanol 100%. Keep O/N at −20° C.
7. Spin at max speed for 40 min, and wash with 85% ethanol. Resuspend in 3 μl. (If two tubes are used, resuspend one for 3 minutes at 65° C. and transfer to the second, wash first tube with 2 ul and pool).
8. Add annealing primer—1 ul of probe 19578176 RT-DT-T7 avrII-short from stock 20 p/ul. Perform step wise annealing.

Prepare Transcript Using the T7-MEGAshortscript Kit:
1. Thaw the T7 10× Reaction Buffer, ribonucleotide solutions at room temperature. Keep the T7 Enzyme Mix on ice. Assemble the reaction at room temperature.
2. Prepare reaction mix according to the following:

|  | Volume | From Stock | Comments |
| --- | --- | --- | --- |
| Template | 4 μl | | |
| T7 10X Reaction Buffer | 1 μl | | |
| T7 ATP Solution (75 mM) | 1 μl | | |
| T7 CTP Solution (75 mM) | 1 μl | | |
| T7 UTP Solution (75 mM) | 0.5 μl | | |
| T7 GTP Solution (75 mM) | 1 μl | | |
| UTP Bio | 0.5 μl | | |
| T7 Enzyme Mix | 1 μl | | |
| Total Volume | 10 μl | | |

3. Incubate the reaction at 37° C. O.N.
4. Spin shortly.
5. To remove the DNA template add:
   1 μl of DNase I., mix well, incubate at 37° C. for 15 min.
6. Acid Phenol:chloroform extraction
   Add: 125 μl nuclease-free water, 15 μl 3 M sodium acetate, and 150 μl Acid Phenol:chloroform. Mix thoroughly. Spin at max speed for 10 min.
7. Precipitate the RNA:
   Mix top phase in new tube with 8 μl glycogen (5 mg/ml), 3.6 volume ethanol (550 μl) Keep O/N at −20° C. (or 2 h at −80 C), Centrifuge max 40 min, Wash with 85% ethanol. and resuspend in 25 μl.
8. Concentration:
   Determine concentration.
9. Purify from free nucleotides.
   Load transcripts on G-25 column.
10. Add bio-RNA spike for hybridization control:
    C-lin4-bio-AS-RNA 5f
    C-mir2-bio-AS-RNA 1f For Hybridization with LUMINEX® Mix Couples Use:
1. 5 μg transcripts, or
2. 0.5 μg purified transcripts.

Example 28

Amplification of microRNA Using SenseAmp Plus™—Genisphere

1. Procedure (Starting from Total RNA)
   a. Enrichment and Concentration of microRNA:
   Microcon YM-100 column (Millipore cat. no. 42413) and a conventional tabletop microfuge.
   Dilute the total RNA sample to 100 μl with 10 mM Tris-HCl, pH 8.0.
   Add the 100 μl of diluted total RNA to the sample reservoir. Do not touch the membrane with the pipette tip. Secure the tube cap and centrifuge for 6 minutes at 13,000 g.
   Save the flow-through material (~95 μl). This is your LMW RNA having an average size less than 80-100 bases long.
   Concentration:
   Microcon YM-3 column (Millipore cat. no. 42404) and a conventional tabletop microfuge.
   Add the LMW RNA from step 3 above (~95 μl flow-through of YM-100) to the YM-3 sample reservoir. Do not touch the membrane with the pipette tip. Secure the tube cap and centrifuge for 30 minutes at 13,000 g.
   Check the volume of the flow-through and continue the centrifugation until the flow-through volume is equal to the loaded volume (~95 μl) minus 6-8 μl or no additional liquid is accumulated in the lower reservoir. For example, if 95 μl was loaded on the YM-3 then the flow through measure 87-89 μl.
   Add 10 μl of 10 mM Tris-HCl, pH 8.0 to the sample reservoir and gently mix by tapping the side.
   Carefully place the sample reservoir upside down in a new collection tube. Centrifuge for 3 minutes at 13,000 g to collect the concentrated LMW RNA. Proceed to the Poly (A) Tailing of microRNA section below.
   b. Poly (A) Tailing of microRNA
   Adjust the volume to 18 ml with Nuclease Free Water (Vial 10).
   Dilute the ATP (Vial 14) in 1 mM Tris pH 8.0 according to the following formula:

$$ATP \text{ dilution factor} = \frac{250000}{ng \text{ of Total } RNA \text{ (into the } YM100 \text{ above)}}$$

For example, if starting with 2000 ng miRNA, the ATP dilution factor=250000÷2000 ng=125.
Dilute the ATP 1:125 by adding 1 ml of ATP (Vial 14) to 125 ml of 1 mM Tris pH 8.0.
For samples less than 50 ng of total RNA: dilute the ATP (Vial 14) 1:5000 in 1 mM Tris pH 8.0.
Add the following components to the 18 ml microRNA, for a volume of 25 ml:
2.5 ml 10× Reaction Buffer (Vial 6)
2.5 ml 25 mM MnCl2 (Vial 17)
1 ml diluted ATP (Vial 14 dilution from step 2)
1 ml PAP Enzyme (Vial 16)
Mix gently and microfuge.
Incubate in a 37° C. heat block for 15 minutes.
Reverse Transcription of Tailed microRNA
Briefly microfuge the 25 ml of tailed microRNA and place on ice.
Prepare a 1:10 dilution of SenseAmp dT primer (Vial 1) by adding 1 ml SenseAmp dT primer to 9 ml 0.1×TE. Vortex and briefly microfuge.
On ice, add 2 ml of 1:10 diluted SenseAmp dT primer (Vial 1 dilution from step 2).
Mix gently and microfuge.
Incubate at 65° C. for 10 minutes and immediately transfer to ice for 2 minutes.
Add the following components on ice, for a volume of 50 ml:
10 ml 5× First Strand Buffer (or equivalent buffer supplied with the reverse transcriptase)
5 ml 0.1M DTT (If supplied with the reverse transcriptase; otherwise use nuclease free water)
2.5 ml dNTP mix (Vial 3)
1 ml Superase-in™ RNase inhibitor (Vial 4)
2 ml SuperScript II reverse transcriptase, 200 units (or equivalent reverse transcriptase)
2.5 ml Nuclease Free Water (Vial 10)

Gently mix (do not vortex) and incubate at 42° C. for one hour.

Stop the reaction by adding 8.75 ml of 0.5M NaOH/50 mM EDTA. Briefly vortex and microfuge.

Note: the reaction may turn to a brown color; this is normal. Incubate at 65° C. for 30 minutes to degrade the miRNA.

Note: the reaction may turn from brown to clear; this is normal.

Neutralize the reaction with 12.5 ml of 1M Tris pH 8.0. This is the cDNA. Briefly vortex and microfuge. Bring the sample to 100 ml by adding 28.75 ml 1×TE Buffer.

c. Purification and Concentration of cDNA

Purify the 100 μl of cDNA using a Microcon YM-100 column (Millipore cat. no. 42413) and a conventional tabletop microfuge.

Add the 100 μl cDNA to the sample reservoir. Do not touch the membrane with the pipette tip. Secure the tube cap and centrifuge for 6 minutes at 13,000 g.

Add 200 μl of 1×TE buffer to the sample reservoir without touching the membrane. Gently mix by pipetting up and down 5 times. Secure the tube cap and centrifuge for 6 minutes at 13,000 g.

Carefully separate the sample reservoir from the collection tube. Discard the flow-through. Place the YM-100 column into the same collection tube.

Add 200 μl of 1×TE buffer to the sample reservoir without touching the membrane. Gently mix by pipetting up and down 5 times. Secure the tube cap and centrifuge for 6 minutes at 13,000 g.

Carefully separate the sample reservoir from the collection tube. Discard the collection tube.

Add 5 μl 1 mM Tris pH 8.0 to the sample reservoir without touching the membrane. Gently tap the side of the reservoir to mix.

Carefully place the sample reservoir upside down in a new collection tube. Centrifuge for 3 minutes at 13,000 g.

Note the volume of cDNA collected in the bottom of the tube (5-10 μl). Bring the volume of cDNA to 10 μl with Nuclease Free Water (Vial 10).

Tailing of First Strand cDNA

Heat purified cDNA (10 ml) to 80° C. for 10 minutes. Put on ice immediately for 1-2 minutes. Briefly microfuge and return to ice.

For each reaction, prepare a Master Mix (10 ml) in a separate tube on ice:
2 ml 10× Reaction Buffer (Vial 6)
2 ml Nuclease Free Water (Vial 10)
4 ml 10 mM dTTP (Vial 5)
2 ml TdT Enzyme (Vial 7)

Combine the Master Mix and the cDNA for a volume of 20 ml. Mix gently and microfuge.

Incubate in a 37° C. heat block for 3 minutes. Do not exceed 3 minutes.

Stop the reaction by heating to 80° C. for 10 minutes. Briefly microfuge and cool to room temperature for 1-2 minutes.

d. T7 Promoter Synthesis

Add 2 ml of SenseAmp T7 Template Oligo (Vial 8) to the tailed cDNA for a volume of 22 ml. Briefly vortex and microfuge.

Incubate at 37° C. for 10 minutes to anneal the strands.

To each reaction, add the following components for a volume of 25 ml:
1 ml 10× Reaction Buffer (Vial 6)
1 ml dNTP mix (Vial 3)
1 ml Klenow Enzyme (Vial 9)

Mix gently and microfuge. Incubate at room temperature for 30 minutes.

Stop the reaction by heating to 65° C. for 10 minutes. Place on ice.

Proceed to the In Vitro Transcription reaction using half (12.5 ml) of the promoter-modified cDNA. Save the remaining modified cDNA at −20° C. for future use or for use in a parallel amplification reaction.

e. In Vitro Transcription

Incubate the 12.5 ml of cDNA at 37° C. for 10 minutes to re-anneal the strands.

Thaw the T7 Nucleotide Mix (Vial 11) and 10×T7 Reaction Buffer (Vial 12) at room temperature, and keep at room temperature until use. Thoroughly vortex the 10×T7 Reaction Buffer (Vial 12) to avoid precipitation of certain buffer components.

For each reaction, add the following components to the 12.5 ml of cDNA at room temperature, for a final volume of 25 ml:
8.0 ml T7 Nucleotide Mix (Vial 11)
2.5 ml 10×T7 Reaction Buffer (Vial 12)
2.0 ml T7 Enzyme Mix (Vial 13)

Mix gently and microfuge. Incubate in a themalcycler (with heated lid) at 37° C. for 4-16 hours. Or, place the reaction in a 37° C. heat block for 5 minutes and then transfer to a 37° C. air hybridization oven for 4-16 hours. It is essential to avoid evaporation and condensation of the reaction during this step.

f. Purification of senseRNA

Purify the senseRNA using the RNeasy MinElute Kit (Qiagen cat. no. 74204) following Qiagen's protocol for RNA Cleanup. To elute, add 14 ml Nuclease Free Water, incubate for two minutes, and then spin. The recovered volume should be approximately 12 ml.

g. Quantitation of senseRNA

Determine the concentration of the senseRNA using the RiboGreen RNA Quantitation Kit (Molecular Probes cat. no. R-11490). Use the Ribosomal RNA standard provided with the kit to prepare a standard curve. Use 1 μl of the purified senseRNA to quantitate. Be sure to use an appropriate reference "blank" sample to avoid inaccurate concentration determination.

Example 29

High Throughput Coupling of Probes to Beads—Using EDC

Buffers: MES buffer, 0.1M (pH=4.5), Tween-20, 0.02%, SDS, 0.1%, TE (pH=8.0)

1. Coupling Protocol

Coupling is preformed between carboxylated beads and amine modified probes using EDC.

Coupling is performed in tubes and washed using a 96 multiwell filter plate, resistant for detergents (Solvinert by Millipore).

1. Re-suspended all probes in DDW to a final concentration of 1 mM.
2. Prepare a 1:10 dilution of all probes in DDW (0.1 mM)
3. EDC aliquots powder should reach room temp.
4. Prepare a coupling table of the coupling reactions to performed.
5. Prepare a set of designated tubes.
6. Re-suspend beads by vortex and sonication for about 20 seconds in original tube.
7. Transfer 200 ul from each bead type to the new designated tube (2.5×10$^6$ beads).

8. Spin at max speed for 2 minutes
9. Remove sup and re-suspend in 25 ul MES pH=4.5. Vortex and sonicate for 20 seconds.
10. Add 1 ul of diluted probe to bead. Use pre-made table to get the appropriate bead probe couple.
11. Mix by vortex.
12. Prepare EDC by suspending 10 mg aliquot with 1 ml DDW to create concentration of 10 mg/ml.
13. Add 1.5 ul of EDC to each couple reaction, vortex.
14. Incubate at room temp, in dark 30 minutes.
15. Prepare a new suspended EDC aliquot.
16. Add 1.5 ul of fresh EDC again to each, vortex.
17. Incubate at room temp, in dark 30 minutes.
18. Pre-wet Solvinert filter plates with 100 µl water. (Millipore).
19. Transfer content of couples from tubes to filter plate according to pre-made table.
20. Add 150 µl of 0.02% Tween-20 to the couple's reaction.
21. Place plate onto vacuum apparatus and apply vacuum.
22. Add 150 µl of 0.02% Tween-20 again to the couple's reaction.
23. Apply vacuum again.
24. Add 150 µl of 0.1% SDS, and apply vacuum.
25. Add 150 µl of 0.1% SDS again, and apply vacuum again.
26. Re-suspend coupled beads in 50 µl TE, pH=8.0, mix by pipeting up and down.
27. Transfer couples to a new 96 well plate (no filter), or to new tubes and keep at 4° C.

2. Chemical Labeling of miRNA—MicroMax ASAP (Accurate, Sensitive, and Precise) Labeling Kit
Procedure
1. Small RNA is isolated from 5 µg total RNA by YM-100.
2. Add naked spikes set.
3. Add 0.5 µl ASAP biotin reagent
4. Add 2.5 µl ASAP labeling buffer.
5. Add DDW to final volume of 10 µl
6. Mix by pipetting.
7. Incubate for 30 minutes at 85° C.
8. Cool to 4° C. for 5 minutes (use PCR machine).
9. Purify labeled miRNA using the Kreapure columns:
  a. Let columns reach room temp (20 minutes)
  b. Shake to pull resin to the bottom
  c. Break the bottom and place in 2 ml microtube.
  d. Loosen the cap and pre-spin for 1 minute 14,000 rpm.
  e. Place the column in a fresh microtube
  f. Apply the labeling reaction on top of the raisin bed.
  g. Spin at 14,000 for 1 minute.
  h. Collect the flow through and store at −20° C. or use from hybridization.

3. LUMINEX® Hybridization Protocol
17 ul Labeled Material:

| Labeled RNA | +33ul Mix beads |
| 2ul Bio-Spikes | (in X1.5 TMAC). 1500 beads/reaction |

Complete volume to 17ul with X1 TE

1. Resuspend microspheres by vortex and sonication for approximately 20 seconds.
2. To each sample or background well add 33 µL of Working Microsphere mix. Reaction is preformed in 0.5 ml tubes.
3. To each background well add 17 µL TE, pH 8.
4. To each sample well add examined material that includes labeling and pre-biotinelated spikes, and add TE pH 8.0 to a total volume of 17 µL.
5. Mix reaction wells gently by pipetting up and down several times.
6. Place tubes in PCR-100 machine (Programmable Thermal controller) at 85° C. for 5 minutes to denature any secondary structure in the sample. Incubate the reaction tubes at 50° C. (hybridization temperature) over night.
7. Transfer the samples into 96 well filter plate. Apply vacuum.
8. Prepare fresh reporter mix by diluting streptavidin-R-phycoerythrin sample (PhycoLink-SteptAvidin. Cat# PJ315) to 20 µg/ml in 1×TMAC Hybridization Buffer.
9. Add 75 µl of reporter mix to each well and mix gently by pipetting up and down several times, and transfer to PCR plate. 10. Return the sample plate to hybridization temperature 50° C. in LUMINEX® machine for 10 minutes.
11. Analyze 50 µl at hybridization temperature on the LUMINEX® analyzer according to the system manual.

REFERENCES

1. Chen C, Ridzon D A, Broomer A J, Zhou Z, Lee D H, Nguyen J T, Barbisin M, Xu N L, Mahuvakar V R, Andersen M R, Lao K Q, Livak K J, Guegler K J. Real-time quantification of microRNAs by stem-loop RT-PCR. Nucleic Acids Res. 2005 Nov. 27; 33(20):e179.
2. Fu H J, Zhu J, Yang M, Zhang Z Y, Tie Y, Jiang H, Sun Z X, Zheng X F. A novel method to monitor the expression of microRNAs. Mol. Biotechnol. 2006 March; 32(3): 197-204.
3. Shi R, Chiang V L. Facile means for quantifying microRNA expression by real-time PCR. Biotechniques. 2005 October; 39(4):519-25.
4. Tang F, Hajkova P, Barton S C, Lao K, Surani M A. MicroRNA expression profiling of single whole embryonic stem cells. Nucleic Acids Res. 2006 Jan. 24; 34(2):e9.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09115389B2). An electronic copy of the "Sequence Listing" will also be available from the USPTO upon request and payment of the fee set forth in 37 CFR 1.19(b)(3).

The invention claimed is:

1. A method of specifically detecting, identifying and quantifying a plurality of microRNAs in a biological sample obtained from a subject, wherein said plurality of microRNAs differ from each other by at least one nucleotide, said method comprising:
   (a) providing RNA from said sample, wherein said RNA comprises microRNAs;
   (b) polyadenylating the RNA;
   (c) generating a reverse transcript of the polyadenylated RNA using a linear reverse transcript primer, wherein said primer is not complementary to the microRNAs; and
   (d) amplifying the reverse transcript of step (c) and specifically quantifying the plurality of microRNAs by polymerase chain reaction comprising a forward primer, a reverse primer, and a linear probe.

2. The method of claim 1, wherein the biological sample is selected from the group consisting of: biopsy, tissue sample, blood, serum, urine, amniotic fluid, ascitic fluid, saliva, cervical secretions, vaginal secretions, effusions, endometrial secretions, gastrointestinal secretions, bronchial secretions, sputum, pleural effusion, secretions from the breast, secretions from ovarian cyst, and sperm.

3. The method of claim 1, wherein said probe further comprises a minor groove binder.

4. The method of claim 1, wherein the forward primer comprises a sequence selected from the group consisting of any one of SEQ ID NOS: 4168-8334.

5. The method of claim 1, wherein the probe comprises a sequence selected from the group consisting of any one of SEQ ID NOS: 8335-20835.

6. A method of detecting a target RNA nucleic acid in a biological sample, wherein said target RNA nucleic acid sequence is a microRNA or an siRNA, the method comprising:
   (a) providing the biological sample comprising the target RNA nucleic acid sequence;
   (b) annealing the target RNA nucleic acid sequence with a poly(T) primer comprising a 5' universal adaptor sequence;
   (c) generating a reverse transcript of the polyadenylated RNA with the poly(T) primer of step (b); and
   (d) amplifying the reverse transcript of step (c) by a polymerase chain reaction (PCR) comprising a specific forward primer, a universal reverse primer and a specific probe, to generate an amplicon;
   wherein the forward primer is at least partially identical to the target RNA nucleic acid sequence, the universal reverse primer is at least partially identical to a 5' region of the adaptor sequence of the poly (T) primer and the specific probe comprises at least one mismatch at the 3' end of the constant region of the amplicon.

7. The method of claim 6, wherein said target RNA sequence of step (a) is extended at the 3' end by polyadenylation prior to step (b).

8. The method of claim 1, wherein the probe comprises a label.

9. The method of claim 8, wherein the label comprises a fluorophore.

10. The method of claim 9, wherein the label further comprises a quencher molecule, and wherein the fluorophore is located on the probe distal to the quencher molecule.

* * * * *